(12) United States Patent
You et al.

(10) Patent No.: US 7,959,923 B2
(45) Date of Patent: Jun. 14, 2011

(54) METHOD FOR TREATING CANCER USING ANTI-WNT2 MONOCLONAL ANTIBODIES AND SIRNA

(75) Inventors: Liang You, San Francisco, CA (US); Biao He, South San Francisco, CA (US); Zhidong Xu, San Francisco, CA (US); David M. Jablons, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 241 days.

(21) Appl. No.: 12/363,579

(22) Filed: Jan. 30, 2009

(65) Prior Publication Data
US 2009/0202539 A1    Aug. 13, 2009

Related U.S. Application Data

(62) Division of application No. 11/131,425, filed on May 16, 2005, now abandoned.

(60) Provisional application No. 60/571,323, filed on May 14, 2004.

(51) Int. Cl.
*A61K 39/395* (2006.01)

(52) U.S. Cl. .................................. 424/155.1; 424/133.1

(58) Field of Classification Search ........................ None
See application file for complete search history.

(56) References Cited

U.S. PATENT DOCUMENTS

| | | | |
|---|---|---|---|
| 5,851,984 | A | 12/1998 | Matthews et al. |
| 6,159,462 | A | 12/2000 | Matthews et al. |
| 6,844,422 | B1 | 1/2005 | Niehrs et al. |
| 2002/0049177 | A1 | 4/2002 | Clark et al. |
| 2002/0187502 | A1 | 12/2002 | Waterman et al. |
| 2002/0192216 | A1 | 12/2002 | Lamb et al. |
| 2003/0044408 | A1 | 3/2003 | Levy et al. |
| 2003/0165500 | A1 | 9/2003 | Rhee et al. |
| 2004/0126359 | A1 | 7/2004 | Lamb et al. |
| 2004/0203003 | A1 | 10/2004 | Rhee et al. |
| 2004/0223952 | A1 | 11/2004 | Ten Have-Opbroek |
| 2004/0247593 | A1 | 12/2004 | He |
| 2005/0049195 | A1 | 3/2005 | Zou |
| 2005/0079173 | A1 | 4/2005 | Niehrs |
| 2006/0040883 | A1 | 2/2006 | You et al. |

FOREIGN PATENT DOCUMENTS

| | | |
|---|---|---|
| WO | W09806747 | 2/1998 |
| WO | WO02088081 | 11/2002 |
| WO | 2004032838 | 4/2004 |
| WO | WO2004026908 | 4/2004 |
| WO | WO2004042028 | 5/2004 |

OTHER PUBLICATIONS

Santa Cruz Biotechnology, Inc., Wnt-2 (V-16): sc-5207, http://www.scbt.com/datasheet-5207-wnt-2-v-16-antibody.html.Feb. 1995.
Santa Cruz Biotechnology, Inc., Wnt-2 (H-20): sc-5208, http://www.scbt.com/datasheet-5208-wnt-2-h-20-antibody.html.Feb. 1995.
Santa Cruz Biotechnology, Inc., Wnt-1 (G-19): sc-6280, http://www.scbt.com/datasheet-6280-wnt-1-g-19-antibody.html. Mar. 1998.
Elbashir, et al., Analysis of gene function in somatic mammalian cells using small interfering RNAs., Methods. Feb. 2002;26(2):199-213.
Appel, et al., Elucidation of discontinuous linear determinants in peptides, The Journal of Immunology, vol. 144, Issue 3 976-983, Copyright 1990 by American Association of Immunologists.
Bafico, et al.,Interaction of Frizzled Related Protein (FRP) with Wnt Ligands and the Frizzled Receptor Suggests Alternative Mechanisms for FRP Inhibition of Wnt Signaling, J Biol Chem, vol. 274, Issue 23, 16180-16187, Jun. 4, 1999.
Holcombe, et at., Expression of Wnt ligands and Frizzled receptors in colonic mucosa and in colon carcinoma, Molecular Pathology 2002;55:220-226.
Katoh, Frequent up-regulation of WNT2 in primary gastric cancer and colorectal cancer, Int J Oncol. Nov. 2001;19(5):1003-1007.
Levay-Young, et al., Growth and developmental regulation of wnt-2 (irp) gene in mesenchymal cells of fetal lung, AJP—Lung Cellular and Molecular Physiology, vol. 262, Issue 6 672-L683, (1992).
Li, et al., Second cysteine-rich domain of Dickkopf-2 activates Canonical Wnt signaling pathway via LRP-6 independently of dishevelled, The Journal of biological chemistry, 2002, vol. 277, No. 8, pp. 5977-5981.
Mahato, et al., Modulation of gene expression by antisense and antigene oligodeoxynucleotides and small interfering RNA, Expert Opin Drug Deliv. Jan. 2005;2(1):3-28.
Molecular Biology, Proceedings of the 92nd Annual Meeting of the American Association for Cancer Research; Mar. 24-28, 2001; New Orleans, Lousianna, vol. 42, p. 609.
Sakurai, cDNA Macroarray Analysis of Genes Involved in the Progression of Human Non-small Cell Lung Carcinomas, Journal of Kanazawa Medical University, vol. 26;No. 4;p. 259-269(2001).
Scherer, et al., Approaches for the sequence-specific knockdown of mRNA, 2003, Nature Biotechnology 21(12), pp. 1457-1465.
Wissmann, et al., WIFI, a component of the Wnt pathway, is down-regulated in prostate, breast, lung, and bladder cancer, J. Pathol. 201, 2003, pp. 204-212.
Zhang, et al., Targeted gene silencing by small interfering RNA-based knock-down technology, Curr Pharm Biotechnol. Feb. 2004;5(1):1-7.
Chen, et al., Wnt-1 signaling inhibits apoptosis by activating beta-catenin/T cell factor-mediated transcription, The Journal of cell biology, vol. 152, No. 1. (Jan. 8, 2001), pp. 87-96.
He, et al., Blockade of Wnt-1 signaling induces apoptosis in human colorectal cancer cells containing downstream mutations, Oncogene. Apr. 21, 2005;24(18), pp. 1-5.
Lustig, et al., The Wnt signaling pathway and its role in tumor development, J Cancer Res Clin Oncol. Apr. 2003;129(4):199-221.
Polakis, Paul, Wnt signaling and cancer, Genes Dev. Aug. 1, 2000;14(15):1837-51.

(Continued)

*Primary Examiner* — Sheela J Huff
(74) *Attorney, Agent, or Firm* — Carol L. Francis; Bozicevic, Field & Francis, LLP

(57) ABSTRACT

This invention relates to methods of inhibiting the growth of cells, in particular cancer cells, that overexpress Wnt2. The methods comprise contacting the cell with an agent that binds to Wnt2 mRNA or Wnt2 protein, interferes with Wnt2 signaling or inhibits binding of the Wnt2 protein to another protein, such as a Frizzled receptor.

15 Claims, 26 Drawing Sheets

OTHER PUBLICATIONS

Rhee, et al., Wnt and frizzled receptors as potential targets for immunotherapy in head and neck squamous cell carcinomas, Oncogene. Sep. 26, 2002;21(43):6598-6605.

You, et al., Wnt signaling promotes oncogenic transformation by inhibiting c-Myc—induced apoptosis, J. Cell Biol. 157(3): 429-440, (2002).

You, et al., Inhibition of Wnt-2-mediated signaling induces programmed cell death in non-small-cell lung cancer cells, Oncogene (2004) 23, 6170-6174.

You, et al., An Anti-Wnt-2 Monoclonal Antibody Induces Apoptosis in Malignant Melanoma Cells and Inhibits Tumor Growth, Cancer Research 64, 5385-5389, Aug. 1, 2004.

```
               <----------------------------------------------------------------------
                     F R 1 - IMGT
                 1           5            10            15             20
               D   I   V   L   T   Q   S   P   A   S   L   A   V   S   L   G   Q   R   A   T   I   S
ly23w21kRs    GAC ATT GTG CTG ACA CAG TCT CCT GCT GCT TCC TTA GCT GTA TCT CTG GGG CAG AGG GCC ACC ATC TCA
               ------------------------>   <-------------------       ---------------------
                                             CDR1 - IMGT
                          25                    30              35              40
               Y   R   A   S   K   S   V   S   T   S   G   Y   S   Y   .   .   M   H   W   N   Q   Q
ly23w21kRs    TAC AGG GCC AGC AAA AGT GTC AGT ACA TCT GGC TAT AGT TAT . . . ATG CAC TGG AAC CAA CAG
               --------------->                                                         <-------
                     F R 2 - IMGT                           CDR2 - IMGT
                45              50               55              60              65
               K   P   G   Q   P   P   R   L   L   I   Y   L   V   S   .   .   .   N
ly23w21kRs    AAA CCA GGA CAG CCA CCC AGA CTC CTC ATC TAT CTT GTA TCC . . . . . . AAC
               --------------------   ------------------>
                                                                 F R 3 - IMGT
                    70              75              80              85
               L   E   S   R   S   P   A   R   F   S   G   Q   .   .   W   C   L   V   Y   R
ly23w21kRs    CTA GAA TCT AGG AGG TCA . . . CCT GCC AGG TTC AGT GGT CAG . . . . . TGG TGT CTG GTG TAC AGA
                                                                           ----------->
                                                                               CDR3 - i
```

```
<---------------------- F  R  1  -  I  M  G  T ----------------
  1                5                     10                    15
  D    I    V    L    T    Q    S    P    A    S    L    A    V    S    L    G    Q    R
 GAC  ATT  GTG  CTG  ACA  CAG  TCT  CCT  GCT  TCC  TTA  GCT  GTA  TCT  CTG  GGG  CAG  AGG

----------------------------->                                 CDR1 - IMGT
       20                  25                     30                   35
  A    T    I    S    Y    R    A    S    K    S    V    S    T    S    G    Y    S    Y
 GCC  ACC  ATC  TCA  TAC  AGG  GCC  AGC  AAA  AGT  GTC  AGT  ACA  TCT  GGC  TAT  AGT  TAT

<---------------------- F  R  2  -  I  M  G  T ---------
                   40                    45                   50
          M    H    W    N    Q    Q    K    P    G    Q    P    P    R    L    L    I
 ... ...  ATG  CAC  TGG  AAC  CAA  CAG  AAA  CCA  GGA  CAG  CCA  CCC  AGA  CTC  CTC  ATC

-->                                            <---------------------------
                  CDR2 - IMGT
  55              60                    65                  70
  Y    L    V    S                             N    L    E    S    G    V    P
 TAT  CTT  GTA  TCC  ... ... ... ... ... ... ...  AAC  CTA  GAA  TCT  GGG  GTC  CCT

------------------------------ F  R  3  -  I  M  G  T ---------
       75                  80                     85                  90
  A    R    F    S    G    S    G              S    G    T    D    F    T    L    N
 GCC  AGG  TTC  AGT  GGC  AGT  GGG  ... ...  TCT  GGG  ACA  GAC  TTC  ACC  CTC  AAC

------------------------------------------------------------>              CDR3
                  95                   100                  105
  I    H    P    V    E    E    E    D    A    A    T    Y    Y    C    Q    H    I    R
 ATC  CAT  CCT  GTG  GAG  GAG  GAG  GAT  GCT  GCA  ACC  TAT  TAC  TGT  CAG  CAC  ATT  AGG

- IMGT
       110                 115                    120                 125
  E    L    T    R    S    E    G    G    P    S    W    K    *    N    G    L    M    L
 GAG  CTT  ACA  CGT  TCG  GAG  GGG  GGA  CCA  AGC  TGG  AAA  TAA  AAC  GGG  CTG  ATG  CTG

130
  H    Q    L
 CAC  CAA  CTG  A
```

FIG. 15A

```
<------------------------  F  R  1  -  I  M  G  T  ------------------
 1              5                       10                   15
 E   V   Q   L   Q   Q   S   G   P       E   L   V   K   P   G   A   S
GAG GTC CAG CTG CAG CAG TCT GGA CCT ... GAG CTG GTG AAG CCT GGG GCT TCT

---------------------------------->                   CDR1  -  IMGT
    20                  25                       30                  35
 V   K   M   S   C   K   A   S   G   Y   T   F   T   T   Y   V
GTG AAG ATG TCC TGC AAG GCT TCT GGA TAC ACA TTC ACT ACC TAT GTT ... ...

<-----------------------  F  R  2  -  I  M  G  T  ---------
 _____
         40                  45                  50
     M   H   W   V   K   Q   K   P   G   Q   G   L   E   W   I   G
... ... ATG CAC TGG GTG AAA CAG AAG CCT GGG CAG GGC CTT GAG TGG ATT GGA

-->                                           <----------------------------
 _____ CDR2  -  IMGT _____
55              60                  65                      70
 Y   I   D   P   Y   N   D   G   T           K   Y   N   E   K   F   K
TAC ATT GAT CCT TAC AAT GAT GGT ACT ... ... AAG TAC AAT GAG AAG TTC AAA

------------------------------        F  R  3  -  I  M  G  T  ---------------
    75                  80                  85                      90
     G   K   A   T   L   T   S   D   K   S   S   S   T   A   Y   M   E
... GGC AAG GCC ACA CTG ACT TCA GAC AAA TCC TCC AGC ACA GCC TAC ATG GAG

------------------------------------------------------------->
            95                  100                 105
 L   S   S   L   T   S   E   D   S   A   V   Y   Y   C   T   R   G   N
CTC AGC AGC CTG ACC TCT GAG GAC TCT GCG GTC TAT TAC TGT ACA AGA GGG AAT

CDR3  -  IMGT
         110                 115                 120                 125
 G   N   Y   E   S   Y   Y   A   M   D   Y   W   G   Q   G   T   S   V
GGT AAC TAC GAG AGT TAC TAT GCT ATG GAC TAC TGG GGT CAA GGA ACC TCA GTC

130
 T   V   S   S   A   K   T   T   P   P   S   V   Y
ACC GTC TCC TCA GCC AAA ACG ACA CCC CCA TCT GTC TAT A
```

FIG. 15B

```
<----------------------- F R 1 - I M G T -----------------
  1           5                  10                 15
  D  I  V  M  T  Q  T  P  L  T  L  S  V  T  I  G  Q  P
 GAC ATT GTG ATG ACA CAG ACT CCA CTC ACT TTG TCG GTT ACC ATT GGA CAA CCA

-------------------------------->                            CDR1 - IMGT
     20               25                      30                       35
  A  S  I  S  C  K  S  S  Q  S  L  L  D  S  D  G  K  T
 GCC TCC ATC TCT TGC AAG TCA AGT CAG AGC CTC TTA GAT AGT GAT GGA AAG ACA

<---------------------  F  R  2 - I  M  G  T  ---------
_____                          45                 50
  Y     L  N  W  L  L  Q  R  P  G  Q  S  P  K  R  L  I
 TAT ... TTG AAT TGG CTG TTA CAG AGG CCA GGC CAG TCT CCA AAG CGC CTA ATC

-->                                       <----------------------------
           _____ CDR2 - IMGT _____
 55                  60                    65                         70
  Y  L  V  S                                  K  L  D  S  G  V  P
 TAT CTG GTG TCT ... ... ... ... ... ... ... AAA CTG GAC TCT GGA GTC CCT

------------------------- F R 3 - I M G T --------------
        75               80                  85                       90
        D  R  F  T  G  S  G        S  G  T  D  F  T  L  K
 ... GAC AGG TTC ACT GGC AGT GGA ... ... TCA GGG ACA GAT TTC ACA CTG AAA

------->
              95                  100                 105
   I  S  R  V  E  A  E  D  L  G  V  Y  Y  C  W  Q  G  T
 ATC AGC AGA GTG GAG GCT GAG GAT TTG GGA GTT TAT TAT TGC TGG CAA GGT ACA

CDR3 - IMGT _____
     110               115                 120
  H  F  P  W  T  L  R  W  R  H  Q  A  E  S  I
 CAT TTT CCG TGG ACG TTG CGG TGG AGG CAC CAA GCT GAA TCA ATC G
```

FIG. 16A

```
<------------------------ F R 1 - I M G T ------------------
     1                 5                      10                      15
     Q  V  Q  L  Q  Q  S  G  A     E  L     G  T  W  G  F
    CAG GTC CAG CTG CAG CAG TCT GGA GCT ... GAG CTG ... GGA ACC TGG GGC TTC

------------------------------->                                 CDR1 - IMGT
       20                   25                     30                     35
     S  E  D  V  L  Q  A  S  G  Y  T  F  T  D  Y  V
    AGT GAA GAT GTC CTG CAG GCT TCT GGA TAC ACA TTC ACT GAC TAT GTT ... ...

<------------------- F R 2 - I M G T ---------
              40                   45                   50
           L  S  W  V  K  Q  R  T  G  Q  G  L  E  W  I  G
    ... ... TTA AGC TGG GTG AAG CAG AGA ACT GGA CAG GGC CTT GAG TGG ATT GGA

-->                     CDR2 - IMGT                <----------------------------
    55                    60                    65                     70
     E  I  Y  P  G  Y  G  S  T        Y  Y  N  E  K  F  K
    GAG ATT TAT CCT GGA TAT GGT AGT ACT ... ... TAC TAC AAT GAG AAG TTC AAG

-------------------------- F R 3 - I M G T -------------
           75                   80                    85                     90
         G  K  A  T  L  T  A  D  K  S  S  N  T  A  Y  M  Q
    ... GGC AAG GCC ACA CTG ACT GCT GAC AAA TCC TCC AAC ACA GCC TAC ATG CAG

--------------------------------------------------->
                                                                         CDR3
             95                    100                   105
     L  S  S  L  T  S  E  D  S  A  V  Y  F  C  A  R  W  G
    CTC AGC AGC CTG ACA TCT GAG GAC TCT GCG GTC TAT TTC TGT GCA AGA TGG GGG

- IMGT
         110                  115                   120                    125
     D  S  F  A  Y  W  G  Q  G  T  L  V  T  V  S  A  A  K
    GAT TCT TTT GCT TAC TGG GGC CAA GGG ACT CTG GTC ACT GTC TCT GCA GCC AAA

130
     T  T  P  P  S  V  Y  x
    ACG ACA CCC CCA TCT GTC TAT AXA A
```

FIG. 16B

```
<----------------------  F  R  1  -  I  M  G  T  ----------------
  1              5                    10                  15
  D  I  V  L  T  Q  S  P  A  S  L  A  V  S  L  G  Q  R
 GAC ATT GTG CTG ACA CAG TCT CCT GCT TCC TTA GCT GTA TCT CTG GGG CAG AGG

------------------------------>
                                                          CDR1 - IMGT
     20                   25                    30                  35
  A  T  I  S  Y  R  A  S  K  S  V  S  T  S  G  Y  S  Y
 GCC ACC ATC TCA TAC AGG GCC AGC AAA AGT GTC AGT ACA TCT GGC TAT AGT TAT

<---------------------  F  R  2  -  I  M  G  T  ---------
                   40                   45                 50
        M  H  W  N  Q  Q  K  P  G  Q  P  P  R  L  L  I
 ... ... ATG CAC TGG AAC CAA CAG AAA CCA GGA CAG CCA CCC AGA CTC CTC ATC

--->              CDR2 - IMGT                      <-------------------
 55                   60                    65                   70
  Y  L  V  S                              N  L  E  S  G  V  P
 TAT CTT GTA TCC ... ... ... ... ... ... ... AAC CTA GAA TCT GGG GTC CCT

-------------------------  F  R  3  -  I  M  G  T  -------------
        75                 80                   85                  90
     A  R  F  S  G  S  G        S  G  T  D  F  T  L  N
 ... GCC AGG TTC AGT GGC AGT GGG ... ... TCT GGG ACA GAC TTC ACC CTC AAC

------------------------------------------------------------>
                                                                 CDR3
              95                   100                  105
  I  H  P  V  E  E  E  D  A  A  T  Y  Y  C  Q  H  I  R
 ATC CAT CCT GTG GAG GAG GAG GAT GCT GCA ACC TAT TAC TGT CAG CAC ATT AGG

- IMGT
     110                  115                  120                  125
  E  L  T  R  S  E  G  G  P  S  W  K  *  N  G  L  M  L
 GAG CTT ACA CGT TCG GAG GGG GGA CCA AGC TGG AAA TAA AAC GGG CTG ATG CTG

H  Q  L
 CAC CAA CTA
```

FIG. 17A

```
<------------------------ F  R  1  -  I  M  G  T ---------------
   1              5                  10                 15
   D  I  V  M  T  Q  T  P  L  T  L  S  V  T  I  G  Q  P
  GAC ATT GTG ATG ACA CAG ACT CCA CTC ACT TTG TCG GTT ACC ATT GGA CAA CCA

-------------------------------->                      CDR1 - IMGT
      20                   25                 30                 35
   A  S  F  S  C  K  S  S  Q  R  L  L  Y  S  N  G  K  T
  GCC TCT TTC TCT TGC AAG TCA AGT CAG AGA CTC TTA TAT AGT AAT GGA AAA ACC

<------------------ F  R  2  -  I  M  G  T ---------
               40                   45                 50
   Y       L  N  W  L  L  Q  R  P  G  Q  S  P  K  R  L  I
  TAT ... TTG AAT TGG TTA TTA CAG AGG CCA GGC CAG TCT CCA AAG CGC CTA ATC

-->           CDR2 - IMGT            <-----------------------------
   55                    60                    65                 70
   Y  L  V  S                            K  L  D  S  G  V  P
  TAT CTG GTG TCT ... ... ... ... ... ... ... AAA CTG GAC TCT GGA GTC CCT

------------------------- F  R  3  -  I  M  G  T -------------
            75                 80                 85                 90
         D  R  F  T  G  S  G           S  G  T  D  F  T  L  K
  ... GAC AGG TTC ACT GGC AGT GGA ... ... TCA GGA ACA GAT TTT ACA CTG AAA

------------------------------------------------------>
                                                              CDR3
            95                100                105
   I  S  R  V  E  A  E  D  L  G  V  Y  Y  C  V  Q  G  T
  ATC AGC AGA GTG GAG GCT GAG GAT TTG GGA GTT TAT TAC TGC GTG CAA GGT ACA

- IMGT
       110                115                120
   H  F  P  W  T  L  R  W  R  H  Q  A  E  I  N  R
  CAT TTT CCT TGG ACG TTG CGG TGG AGG CAC CAA GCT GAA ATC AAT CG
```

FIG. 17B

```
<------------------ F  R  1  -  I  M  G  T ----------------
1              5                    10                  15
E  V  Q  L  Q  E  S  G  P       E  L  V  K  P  G  A  S
GAG GTT CAG CTG GAG GAG TCA GGA CCT ... GAG CTG GTA AAG CCT GGG GCT TCT

---------------------------------->                              CDR1 - IMGT
     20                    25                    30                  35
V  K  M  S  C  K  A  S  G  Y  T  F  T  T  Y  V
GTG AAG ATG TCC TGC AAG GCT TCT GGA TAC ACA TTC ACT ACC TAT GTT ... ...

<------------------- F  R  2  -  I  M  G  T --------
-------
        40                    45                    50
     M  H  W  V  K  Q  K  P  G  Q  G  L  E  W  I  G
... ... ATG CAC TGG GTG AAA CAG AAG CCT GGG CAG GGC CTT GAG TGG ATT GGA

-->          CDR2 - IMGT                               <-------------------------
55                     60                    65                    70
Y  I  D  P  Y  N  D  G  T           K  Y  N  E  K  F  K
TAC ATT GAT CCT TAC AAT GAT GGT ACT ... ... AAG TAC AAT GAG AAG TTC AAA

------------------------  F  R  3  -  I  M  G  T -------------
     75                    80                    85                  90
     G  K  A  T  L  T  S  D  K  S  S  S  T  A  Y  M  E
... GGC AAG GCC ACA CTG ACT TCA GAC AAA TCC TCC AGC ACA GCC TAC ATG GAG

---------------------------------------------------->
        95                    100                   105
L  S  S  L  T  S  E  D  S  A  V  Y  Y  C  T  R  G  N
CTC AGC AGC CTG ACC TCT GAG GAC TCT GCG GTC TAT TAC TGT ACA AGA GGG AAT

CDR3 - IMGT
     110                   115                   120                 125
G  N  Y  E  S  Y  Y  A  M  D  Y  W  G  Q  G  T  S  V
GGT AAC TAC GAG AGT TAC TAT GCT ATG GAC TAC TGG GGT CAA GGA ACC TCA GTC

130
T  V  S  S  A
ACC GTC TCC TCA GCC
```

FIG. 17C

```
<---------------------    F   R   1  -  I   M   G   T   ---------------
     1               5                       10                      15
     D   I   V   L   T   Q   S   P   A   S   L   A   V   S   L   G   Q   R
    GAC ATT GTG CTG ACA CAG TCT CCT GCT TCC TTA GCT GTA TCT CTG GGG CAG AGG

-------------------------------->
                                                          CDR1 - IMGT
        20                  25                      30              35
    A   T   I   S   Y   R   A   S   K   S   V   S   T   S   G   Y   S   Y
    GCC ACC ATC TCA TAC AGG GCC AGC AAA AGT GTC AGT ACA TCT GGC TAT AGT TAT

<-------------------    F   R   2  -  I   M   G   T   --------
            40                      45                      50
        M   H   W   N   Q   Q   K   P   G   Q   P   P   R   L   L   I
    ... ... ATG CAC TGG AAC CAA CAG AAA CCA GGA CAG CCA CCC AGA CTC CTC ATC

-->                                           <------------------------------
            CDR2 - IMGT
    55                  60                      65                  70
    Y   L   V   S                                   N   L   E   S   G   V   P
    TAT CTT GTA TCC ... ... ... ... ... ... ... AAC CTA GAA TCT GGG GTC CCT

-----------------------------    F   R   3  -  I   M   G   T   ---------------
        75                  80                      85                  90
    A   R   F   S   G   S   G                   S   G   T   D   F   T   L   N
    ... GCC AGG TTC AGT GGC AGT GGG ... ... TCT GGG ACA GAC TTC ACC CTC AAC

------------------------------------------------------------>
                                                                        CDR3
                95                      100                 105
    I   H   P   V   E   E   E   D   A   A   T   Y   Y   C   Q   H   I   R
    ATC CAT CCT GTG GAG GAG GAG GAT GCT GCA ACC TAT TAC TGT CAG CAC ATT AGG

-  IMGT
        110                 115                 120                 125
    E   L   T   R   S   E   G   G   P   S   W   K   *   N   G   L   M   L
    GAG CTT ACA CGT TCG GAG GGG GGA CCA AGC TGG AAA TAA AAC GGG CTG ATG CTG
```

FIG. 18A

```
<---------------------- F  R  1  -  I  M  G  T  ----------------
  1              5                  10                 15
  D  I  V  M  T  Q  T  P  L  T  L  S  V  T  I  G  Q  P
 GAC ATT GTG ATG ACA CAG ACT CCA CTC ACT TTG TCG GTT ACC ATT GGA CAA CCA

------------------------------>                       CDR1 - IMGT
     20                  25                 30                 35
  A  S  I  S  C  K  S  S  Q  S  L  L  D  S  D  G  K  T
 GCC TCC ATC TCT TGC AAG TCA AGT CAG AGC CTC TTA GAT AGT GAT GGA AAG ACA

<------------------  F  R  2  -  I  M  G  T  -------
                40                 45                 50
  Y     L  N  W  L  L  Q  R  P  G  Q  S  P  K  R  L  I
 TAT ... TTG AAT TGG TTG TTA CAG AGG CCA GGC CAG TCT CCA AAG CGC CTA ATC

-->            CDR2 - IMGT                  <--------------------------

55                   60                 65                 70
  Y  L  V  S                          K  L  D  S  G  V  P
 TAT CTG GTG TCT ... ... ... ... ... ... ... AAA CTG GAC TCT GGA GTC CCT

-------------------------  F  R  3  -  I  M  G  T  -----------
           75                 80                 85                 90
     D  R  F  T  G  S  G        S  G  T  D  F  T  L  K
 ... GAC AGG TTC ACT GGC AGT GGA ... ... TCA GGG ACA GAT TTC ACA CTG AAA

------>
                                                            CDR3
              95                 100                105
  I  S  R  V  E  A  E  D  L  G  V  Y  Y  C  W  Q  G  T
 ATC AGC AGA GTG GAG GCT GAG GAT TTG GGA GTT TAT TAT TGC TGG CAA GGT ACA

- IMGT
    110                115                120
  H  F  P  W  T  F  G  G  G  T  K  L  K  S  T
 CAT TTT CCG TGG ACG TTC GGT GGA GGC ACC AAG CTG AAA TCA ACG
```

FIG. 18B

```
<------------------------    F  R  1  -  I  M  G  T  ----------------
    1              5                      10                      15
    Q   V   Q   L   Q   Q   S   G   A       E   L   V   R   P   G   T   S
    CAG GTC CAG CTG CAG CAG TCT GGA GCT ... GAG CTG GTA AGG CCT GGA ACT TCA
```

```
-------------------------------->                           CDR1 - IMGT
        20                  25                      30                  35
    V   K   V   S   C   K   A   S   G   Y   T   F   T   D   Y   V
    GTG AAG GTG TCC TGC AAG GCT TCT GGA TAC ACA TTC ACT GAC TAT GTT ... ...

<---------------------    F  R  2  -  I  M  G  T  ---------
                40                  45                  50
        L   S   W   V   K   Q   R   T   G   Q   G   L   E   W   I   G
    ... ... TTA AGC TGG GTG AAG CAG AGA ACT GGA CAG GGC CTT GAG TGG ATT GGA

-->                 CDR2 - IMGT                 <--------------------------
55                  60                  65                      70
    E   I   Y   P   G   Y   G   S   T               Y   Y   N   E   K   F   K
    GAG ATT TAT CCT GGA TAT GGT AGT ACT ... ... TAC TAC AAT GAG AAG TTC AAG

-----------------------    F  R  3  -  I  M  G  T  -------------
        75                  80                  85                      90
        G   K   A   T   L   T   A   D   K   S   S   N   T   A   Y   M   Q
    ... GGC AAG GCC ACA CTG ACT GCT GAC AAA TCC TCC AAC ACA GCC TAC ATG CAG

------------------------------------------------------------>
                                                                        CDR3
                95                  100                 105
    L   S   S   L   T   S   E   D   S   A   V   Y   F   C   A   R   W   G
    CTC AGC AGC CTG ACA TCT GAG GAC TCT GCG GTC TAT TTC TGT GCA AGA TGG GGG

- IMGT
    110                 115                 120                 125
    D   S   F   A   Y   W   G   Q   G   T   L   V   T   V   S   A   A   K
    GAT TCT TTT GCT TAC TGG GGC CAA GGG ACT CTG GTC ACT GTC TCT GCA GCC AAA

130
    T   T   P   P   S   V   Y
    ACG ACA CCC CCA TCT GTC TAT A
```

FIG. 18C

METHOD FOR TREATING CANCER USING ANTI-WNT2 MONOCLONAL ANTIBODIES AND SIRNA

CROSS-REFERENCE TO RELATED APPLICATIONS

This application claims benefit of provisional application Ser. No. 60/571,323, filed May 14, 2004, the disclosure of which is incorporated in its entirety herein by reference.

FIELD OF THE INVENTION

This invention relates to methods of inhibiting the growth of cancer cells that overexpress Wnt2 protein. The methods comprise contacting the cell with an agent that binds to Wnt2 mRNA or Wnt2 protein, interferes with Wnt2 signaling, or inhibits binding of the Wnt2 protein to other proteins, such as the Frizzled receptor.

BACKGROUND OF THE INVENTION

Lung Cancer is the leading cause of cancer death in the United States and worldwide, with >170,000 newly diagnosed cases each year in the US and nearly a million cases worldwide (Minna et al. *Cancer Cell.* 1 (1):49-52 (2002)). Despite aggressive approaches made in the therapy of lung cancer in the past decades, the 5-year survival rate for lung cancer remains under 15% (Minna et al. *Cancer Cell.* 1 (1): 49-52 (2002)). Lung cancers are divided into two groups: non-small-cell lung cancer (NSCLC) and small-cell lung cancer (SCLC). NSCLC (75-80% of all cancers) consists of three major types: adenocarcinoma, squamous cell carcinoma, and large cell carcinoma (Minna (2002)). Lung carcinomas and squamous cell carcinomas represent 6-70% of all lung cancers. Surgery, chemotherapy, and radiation have been used with generally unsatisfactory results in advanced disease. Improvement in the efficacy of lung cancer treatment is a major public health goal.

Malignant pleural mesothelioma (MPM) is a highly aggressive and challenging cancer arising primarily from the pleural lining of the lung. Approximately 3,000 patients are diagnosed with MPM in the United States annually and the incidence of this tumor is predicted to increase dramatically over near term, peaking around 2020 (Thatcher, *Lung Cancer* 45 Suppl 1:S1-2 (2004)). Since MPM usually presents at an advanced stage, a curative resection is rarely possible. Radiotherapy has failed to show clinical benefit as a single treatment modality, and the administration of chemotherapy is mostly restricted to the advanced stage with limited efficiency (Kindler, *Lung Cancer* 45 Suppl 1:S125-7 (2004)). Alternative strategies based on pleural injections of recombinant cytokines have similarly proven unsatisfactory (Bard et al. *Lung Cancer* 45 Suppl 1:S129-31 (2004)). Since current interventions offer only limited benefit, and overall survival is low, there is an urgent need to develop new therapeutic agents based on a greater understanding of MPM's underlying molecular mechanisms.

Molecular pathogenesis of lung cancer and MPM includes alterations of expression and function of multiple genes, involving dominant oncogenes and recessive tumor suppressor genes, and abnormalities in cell signaling transduction pathways. A better understanding of molecular mechanisms for lung cancer and MPM pathogenesis should improve the treatment of patients with lung cancer.

The Wingless-type (Wnt) family of secreted glycoproteins is a group of signaling molecules broadly involved in developmental processes and oncogenesis (Polakis, *Genes Dev.* 14:1837-51 (2000); Lustig et al. *J. Cancer Res. Clin. Oncol.* 129:199-221 (2003)). Nineteen human Wnt proteins have thus far been identified. Transduction of Wnt signals is triggered by the binding of Wnt ligands to two distinct families of cell-surface receptors: the frizzled (Fz) receptor family and the LDL-receptor-related protein (LRP) family (Akiyama, *Cytokine Growth Factor Rev.* 11:273-82 (2000)). Intracellularly, Wnt signaling activates disheveled (Dvl) proteins, which inhibit glycogen synthase kinase-3β (GSK-3β) phosphorylation of β-catenin leading to its cytosolic stabilization. Stabilized β-catenin then enters the cell nucleus and associates with LEF/TCF transcription factors. β-catenin-Tcf/Lef induces transcription of important downstream target genes, many of which have been implicated in cancer. In the absence of Wnt signals, free cytosolic β-catenin is incorporated into a complex consisting of Axin, the adenomatous polyposis coli (APC) gene product, and glycogen synthase kinase (GSK)-3β. Conjunctional phosphorylation of Axin, APC, and β-catenin by GSK-3β designates β-catenin for the ubiquitin pathway and degradation by proteasomes (Uthoff et al., *Int J Oncol* 19 (4):803-10 (2001); Matsuzawa et al., *Mol Cell* 7 (5):915-26 2001)).

Disheveled (Dvl) is a positive mediator of Wnt signaling positioned downstream of the frizzled receptors and upstream of β-catenin. GSK-3 phosphorylates several proteins in the Wnt pathway and is instrumental in the downstream regulation of β-catenin. Mutations in the gene APC are an initiating event for both sporadic and hereditary colorectal tumorigenesis. APC mutants are relevant in tumorigenesis, since the aberrant protein is an integral part of the Wnt-signaling cascade. The protein product contains several functional domains acting as binding and degradation sites for β-catenin. Mutations that occur in the amino-terminal segment of β-catenin are usually involved in phosphorylation-dependent, ubiquitin-mediated degradation and, thus, stabilize β-catenin. When stabilized cytoplasmic-catenin accumulates, it translocates to the nucleus interacting with the Tcf/Lef high-mobility group of transcription factors that modulate expression of oncogenes such as c-myc.

It is known that Wnt/β-catenin signaling promotes cell survival in various cell types (Orford et al., *J Cell Biol* 146 (4):855-68 (1999); Cox et al., *Genetics* 155 (4):1725-40 (2000); Reya et al., *Immunity* 13 (1):15-24 (2000); Satoh et al., *Nat_Genet.* 24 (3):245-50 (2000); Shih et al., *Cancer Res* 60 (6):1671-6 (2000); Chen et al., *J Cell Biol* 152 (1):87-96 (2001); Ioannidis et al., *Nat_Immunol* 2 (8):691-7 (2001)). Wnt signaling pathway is also thought to be associated with tumor development and/or progression (Bienz et al., *Cell* 103 (2):311-20 (2000); Cox et al., *Genetics* 155 (4):1725-40 (2000); (Polakis, *Genes Dev* 14 (15):1837-51 (2000); You et al., *J Cell Biol* 157 (3): 429-40 (2002)). Aberrant activation of the Wnt signaling pathway is associated with a variety of human cancers, correlating with the overexpression or amplification of c-Myc (He et al., *Science* 281 (5382):1509-12 (1998); Miller et al., *Oncogene* 18 (55):7860-72 (1999); Bienz et al., *Cell* 103 (2):311-20 (2000); (Polakis, *Genes Dev* 14 (15):1837-51 (2000); Brown, *Breast Cancer Res* 3 (6): 351-5 (2001)). In addition, c-Myc was identified as one of the transcriptional targets of the β-catenin/Tcf in colorectal cancer cells (He et al., *Science* 281 (5382):1509-12 (1998); Miller et al., *Oncogene* 18 (55):7860-72 (1999); You et al., *J Cell Biol* 157 (3): 429-40 (2002)).

In addition to the Wnt ligands, a family of secreted Frizzled-related proteins (sFRPs) has been isolated. sFRPs appear to function as soluble endogenous modulators of Wnt signaling by competing with the membrane-spanning Frizzled receptors for the binding of secreted Wnt ligands (Melkonyan et al., *Proc Natl Acad Sci USA* 94 (25):13636-41 (1997)). sFRPs can either antagonize Wnt function by binding the protein and blocking access to its cell surface signaling receptor, or they can enhance Wnt activity by facilitating the presentation of ligand to the Frizzled receptors (Uthoff et al., *Int J Oncol* 19 (4):803-10 (2001)). sFRPs seem to modulate apoptosis susceptibility, exerting an antagonistic effect on programmed cell death. To date, sFRPs have not yet been linked causatively to cancer. However, sFRPs are reported to be hypermethylated with a high frequency in colorectal cancer cell lines and this hypermethylation is associated with a lack of basal sFRP expression (Suzuki et al., *Nat Genet* 31 (2):141-9 (2002)).

Another protein called Dickkopf (Dkk) is also found to interfere with Wnt signaling and diminish accumulation of cytosolic β-catenin (Moon et al., *Cell* 88 (6):725-8 (1997); Fedi et al., *J Biol Chem* 274 (27):19465-72 (1999)). Dkk-1 antagonizes Wnt-induced signals by binding to a LDL-receptor-related protein 6 (LRP6) adjacent to the Frizzled receptor (Nusse, *Nature* 411 (6835):255-6 (2001)). Overexpression of Dkk-1 is also found to sensitize brain tumor cells to apoptosis (Shou et al., *Oncogene* 21 (6):878-89 (2002)).

The effects of Wnt proteins on cell proliferation and tumor growth seem to depend on Wnt proteins interacting with their cognate cell surface receptors and subsequently inducing downstream signaling. With Wnt proteins being secreted ligands antibodies may be used to interfere with or inhibit Wnt binding to its cell surface receptor and thus affect downstream signaling. Several antibodies against Wnt proteins have been generated. For example, anti-Wnt-1 (G-19) (sc-6280; Santa Cruz Biotechnology, Inc.) and anti Wnt2 (H-20) (sc-5208; Santa Cruz Biotechnology, Inc.) are goat polyclonal antibodies raised against peptides mapping near the N-terminus of human Wnt-1 and Wnt2 proteins, respectively. Wnt2 (V-16) is a goat polyclonal antibody raised against a peptide mapping within an internal region of Wnt2 of human origin (sc-5207; Santa Cruz Biotechnology, Inc.).

However, the use of polyclonal and monoclonal antibodies in humans is severely restricted when the polyclonal monoclonal antibodies are produced in a non-human animal. Repeated injections in humans of a "foreign" antibody, such as a mouse antibody, may lead to harmful hypersensitivity reactions, i.e., human anti-mouse antibody (HAMA) or an anti-idiotypic, response. The HAMA response makes repeated administrations ineffective due to an increased rate of clearance from the patient's serum and/or allergic reactions by the patient.

Attempts have been made to manufacture human-derived monoclonal antibodies using human hybridomas. Unfortunately, yields of monoclonal antibodies from human hybridoma cell lines are relatively low compared to mouse hybridomas. Additionally, human cell lines expressing immunoglobulins are relatively unstable compared to mouse cell lines, and the antibody producing capability of these human cell lines is transient. Thus, while human immunoglobulins are highly desirable, human hybridoma techniques have not yet reached the stage where human monoclonal antibodies with the required antigenic specificities can be easily obtained. Thus, antibodies of non-human origin have been genetically engineered to create chimeric or humanized antibodies. Such genetic engineering results in antibodies with a reduced risk of a HAMA response compared to that expected after injection of a human patient with a mouse antibody. For example, chimeric antibodies can be formed by grafting nor-human variable regions to human constant regions (Khazaeli et al. (1991), *J. Immunotherapy* 15:42-52).

Generally humanized antibodies, are formed by grafting non-human Complementarity Determining Regions (CDRs) onto human Framework Regions (FRs) (See, Jones et al. (1986), *Nature* 321:522-525; and Reichman et al. (1988), *Nature* 332:323-327). Typically, humanized monoclonal antibodies are formed by grafting all six (three light chain and three heavy chain) CDRs form a non-human antibody into Framework Regions (FRs) of a human antibody (e.g., see, U.S. Pat. No. 6,407,213). Alternately, Fv antibodies (See, U.S. Pat. No. 4,642,334) or single chain Fv (SCFV) antibodies (See, U.S. Pat. No. 4,946,778) can be employed to reduce the risk of a HAMA response.

Despite recent advances in the understanding of Wnt2 signaling, the role of this pathway in oncogenesis is unclear. Thus, the prior art fails to provide clear evidence that compounds that modulate the Wnt2 pathway could be useful for example, for the treatment of cancer. The present invention addresses these and other needs.

SUMMARY OF THE INVENTION

This invention provides a method of inhibiting the proliferation of a cell that overexpresses a Wnt2. The method comprises contacting the cell with an amount of an agent that inhibits Wnt2 signaling effective to inhibit proliferation of the cell.

In some embodiments, the cell is a cancer cell. The cancer cell is selected from the group consisting of breast, ovarian, colorectal, gastric, lung, kidney, bladder, prostate, uterine, thyroid, pancreatic, cervical, esophageal, mesothelioma, head and neck, hepatocellular, melanoma, brain, vulval, testicular, sarcoma, intestine, skin, leukemia, and lymphoma cancer cells.

In one embodiment, the agent is a siRNA. In some embodiments, the agent is an anti-Wnt2 antibody, for example, an antibody that specifically binds to the Wnt2 protein, preferably a human Wnt2 protein.

Antibodies of the invention can be polyclonal or monoclonal antibodies. Preferred are anti-Wnt2 monoclonal antibodies. Preferred monoclonal antibodies comprise (i) a $V_L$CDR1 amino acid sequence as shown in SEQ ID NO:56, SEQ ID NO:104 or SEQ ID NO: 125; (ii) a $V_L$CDR2 amino acid sequence as shown in SEQ ID NO:58; (iii) a $V_L$CDR3 amino acid sequence as shown in SEQ ID NO:60, SEQ ID NO:84, SEQ ID NO:107, SEQ ID NO:126 or SEQ ID NO:138; (iv) a $V_H$CDR1 amino acid sequence as shown in SEQ ID NO:63 or SEQ ID NO:87; (v) a $V_H$CDR2 amino acid sequence as shown in SEQ ID NO:65 or SEQ ID NO:89; and (vi) a $V_H$CDR3 amino acid sequence as shown in SEQ ID NO:67, SEQ ID NO:91 or SEQ ID NO:110.

The invention further provides anti-Wnt2 antibodies that specifically bind a polypeptide comprising an amino acid sequence corresponding to amino acid residues 49-63 of human Wnt2 (SEQ ID NO:2). Another anti-Wnt2 antibody specifically binds a polypeptide comprising SSQRQLCHRPDVMR (SEQ ID NO:2).

This invention also provides an anti-Wnt2 antibody that competes for binding a Wnt2 protein with a second anti-Wnt2 antibody that specifically binds a polypeptide comprising an amino acid sequence corresponding to amino acid residues 49-63 of human Wnt2 (SEQ ID NO:2). Another anti-Wnt2 antibody competes for binding a Wnt2 protein with a second anti-Wnt2 antibody that specifically binds a polypeptide comprising SSQRQLCHRPDVMR (SEQ ID NO:2).

The invention further provides a method of inducing apoptosis of a cell that overexpresses a Wnt2. This method comprises contacting the cell with an amount of an agent that inhibits Wnt2 signaling effective to induce apoptosis of the cell. In another aspect a method of inhibiting Wnt2 signaling in a cell is provided. This method comprises contacting the cell that overexpresses a Wnt2 with an amount of an anti-Wnt2 antibody effective to inhibit Wnt2 signaling.

In a preferred embodiment of the present invention, a method of treating a disease associated with Wnt2 signaling is provided. This method comprises administering to a subject in need of such treatment an amount of an agent that inhibits Wnt2 signaling effective to treat the disease. The agent can be an anti-Wnt2 antibody or a siRNA. The disease can be a cancer, preferably a cancer selected from the group consisting of breast, ovarian, colorectal, gastric, lung, kidney, bladder, prostate, uterine, thyroid, pancreatic, cervical, esophageal, mesothelioma, head and neck, hepatocellular, melanoma, brain, vulval, testicular, sarcoma, intestine, skin, leukemia, and lymphoma cancer cells.

In another embodiment of the present invention, a method of treating a cancer that overexpresses Wnt2 is provided. This method comprises administering to a subject an amount of an anti-Wnt2 antibody, as described herein, effective to treat the cancer. Preferably, the anti-Wnt2 antibody is a monoclonal antibody. In a preferred embodiment, the anti-Wnt2 antibody comprises (i) a $V_L$CDR1 amino acid sequence as shown in SEQ ID NO:56, SEQ ID NO:104 or SEQ ID NO:125; (ii) a $V_L$CDR2 amino acid sequence as shown in SEQ ID NO:58; (iii) a $V_L$CDR3 amino acid sequence as shown in SEQ ID NO:60, SEQ ID NO:84, SEQ ID NO:107, SEQ ID NO:126 or SEQ ID NO:138; (iv) a $V_H$CDR1 amino acid sequence as shown in SEQ ID NO:63 or SEQ ID NO:87; (v) a $V_H$CDR2 amino acid sequence as shown in SEQ ID NO:65 or SEQ ID NO:89; and (vi) a $V_H$CDR3 amino acid sequence as shown in SEQ ID NO:67, SEQ ID NO:91 or SEQ ID NO:110.

The invention further provides a monoclonal anti-Wnt2 antibody that specifically binds a polypeptide comprising an amino acid sequence that corresponds to amino acid residues 49-63 of human Wnt2 (SEQ ID NO:2). In a preferred embodiment of the present invention, this monoclonal anti-Wnt2 antibody competes for binding to a Wnt2 protein with a second anti-Wnt2 antibody that specifically binds a polypeptide comprising an amino acid sequence that corresponds to amino acid residues 49-63 of human Wnt2 (SEQ ID NO:2).

This invention further provides nucleic acids encoding anti-Wnt2 antibodies and functional fragments thereof. In a preferred embodiment, a nucleic acid encoding an anti-Wnt2 antibody comprises (i) a nucleic acid encoding a $V_L$CDR1 selected from the group consisting of nucleic acid sequences shown in SEQ ID NO:70, SEQ ID NO:113 and SEQ ID NO:131; (ii) a nucleic acid encoding a $V_L$CDR2 selected from the group consisting of nucleic acid sequences shown in SEQ ID NO:72 and SEQ ID NO:115; (iii) a nucleic acid encoding a $V_L$CDR3 selected from the group consisting of nucleic acid sequences shown in SEQ ID NO:94, SEQ ID NO:117, SEQ ID NO:134 and SEQ ID NO:143; (iv) a nucleic acid encoding a $V_H$CDR1 selected from the group of nucleic acid sequences shown in SEQ ID NO:77 and SEQ ID NO:97; (v) a nucleic acid encoding a $V_H$CDR2 selected from the group of nucleic acid sequences shown in SEQ ID NO:79 and SEQ ID NO:99; and (vi) a nucleic acid encoding a $V_H$CDR3 selected from the group of nucleic acid sequences shown in SEQ ID NO:101 and SEQ ID NO:120.

Further, this invention provides pharmaceutical compositions comprising an anti-Wnt2 antibody or a siRNA and a pharmaceutically acceptable excipient, carrier and/or diluent.

Methods of the present invention can be practiced in vitro and/or in vivo. Methods, antibodies, pharmaceutical compositions and kits of the invention embrace the specifics as described herein.

BRIEF DESCRIPTION OF THE DRAWINGS

FIG. 11B An example of the morphology of the H28 cells after the treatment with Wnt2 antibody. FIG. 11C A summary of the percentage of apoptotic cells as measured by flow cytometry three days after no treatment (white columns), control antibody treatment (light gray columns) or Wnt2 monoclonal antibody at 10 µg/ml (dark gray columns). Results are the means±SD (error bars). FIG. 11D Apoptosis analysis by flow cytometry. H28 and 513 cells were treated with 10.0 µg/ml of control antibody, and 10.0 µg/ml of anti-Wnt2 antibody, respectively, for about 72 hrs. FL1-H represents Annexin V-FITC staining and FL3-H Propiodium Iodide staining (PI).

FIGS. 14A-14C. Amino acid and nucleic acid sequences of Complementarity Determining Regions (CDR) and Framework Regions (FR) of anti-Wnt2 monoclonal antibody 17F7.G7 (subclone A). Sequences for the light chain kappa (peptide SEQ ID NO:54 and polynucleotide SEQ ID NO:153) and the heavy chain $IgG_1$ (peptide SEQ ID NO:154 and polynucleotide SEQ ID NO:75) are shown. The numbering refers to the position of amino acid residues based on alignment with a mouse monoclonal antibody (IMGT, Immunogen Genetics). FR regions are indicated by interrupted lines, CDR regions by solid lines.

FIGS. 15A-15B. Amino acid and nucleic acid sequences of Complementarity Determining Regions (CDR) and Framework Regions (FR) of anti-Wnt2 monoclonal antibody 8B11.D2. A. Sequences for the light chain kappa (peptide SEQ ID NO:82 and 156, and polynucleotide SEQ ID NO:155). B. Sequences for the heavy chain $IgG_1$ (peptide SEQ ID NO:85 and polynucleotide SEQ ID NO:95). Numbering of amino acid residues is as described in FIGS. 14A-14C. FR regions are indicated by interrupted lines, CDR regions by solid lines.

FIGS. 16A-16B. Amino acid and nucleic acid sequences of Complementarity Determining Regions (CDR) and Framework Regions (FR) of anti-Wnt2 monoclonal antibody 17F7.E5. A. Sequences for the light chain kappa (peptide SEQ ID NO: 102 and polynucleotide SEQ ID NO:111). B. Sequences for the heavy chain $IgG_1$ (peptide SEQ ID NO:157 and polynucleotide SEQ ID NO:118). Numbering of amino acid residues is as described in FIGS. 14A-14C. FR regions are indicated by interrupted lines, CDR regions by solid lines.

FIGS. 17A-17C. Amino acid and nucleic acid sequences of Complementarity Determining Regions (CDR) and Framework Regions (FR) of anti-Wnt2 monoclonal antibody 8B11.H6. A. Sequences for the light chain kappa (Chain-1) (peptide SEQ ID NOs:121 and 156, and polynucleotide SEQ ID NO:158). B. Sequences for the light chain kappa (Chain-2) (peptide SEQ ID NO:123 and polynucleotide SEQ ID NO:129). C. Sequences for the heavy chain $IgG_1$ (peptide SEQ ID NO:127 and polynucleotide SEQ ID NO:135). Numbering of amino acid residues is as described in FIGS. 14A-14C. FR regions are indicated by interrupted lines, CDR regions by solid lines.

FIGS. 18A-18C. Amino acid and nucleic acid sequences of Complementarity Determining Regions (CDR) and Framework Regions (FR) of anti-Wnt2 monoclonal antibody 17F7.G7 (subclone B). A. Sequences for the light chain kappa (Chain-1) (peptide SEQ ID NOs: 82 and 160, and polynucleotide SEQ ID NO:159). B. Sequences for the light chain kappa (Chain-2) (peptide SEQ ID NO:137 and polynucleotide SEQ ID NO:141). C. Sequences for the heavy chain IgG₁ (peptide SEQ ID NO: 139 and polynucleotide SEQ ID NO:144). Numbering of amino acid residues is as described in FIGS. 14A-14C. FR regions are indicated by interrupted lines, CDR regions by solid lines.

DEFINITIONS

Figure 1:
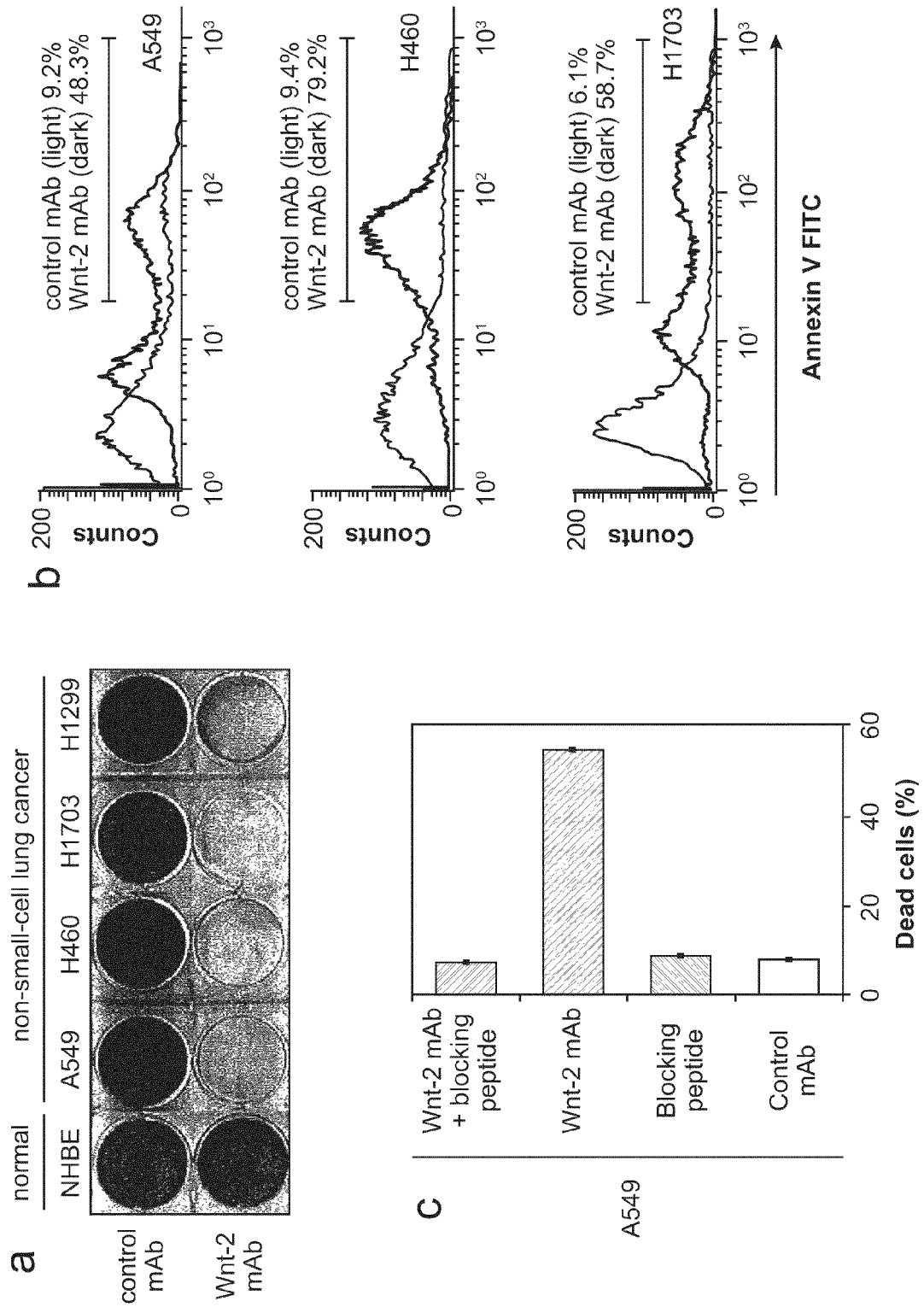
FIG. 1. Anti-Wnt2 monoclonal antibody induces apoptosis in cancer cells. (a) This panel shows 0.5% Crystal Violet staining of NHBE cells and four human NSCLC cell lines (A549, H460, H1703, and H1299) after the anti-Wnt2 antibody treatment. (b) The panel shows these examples of apoptosis analysis by flow cytometry. From top to bottom, A549, H460, and H1703 NSCLC cells were treated with control antibody and anti Wnt2 monoclonal antibody, respectively. (c) Specific cell killing by anti Wnt2 monoclonal antibody in NSCLC cell line A549. The panel shows percentage of dead A549 cells after about 72 h treatment with monoclonal antibody alone and with monoclonal antibody blocked by preincubation with blocking peptide. Controls are blocking peptide alone and control mAb. After incubation, cells were collected for flow cytometry analysis. Results are the means±s.d. (error bars).

The terms "Wnt protein" or "Wnt ligand" refer to a family of mammalian proteins related to the *Drosophila* segment polarity gene, wingless. In humans, the Wnt family of genes typically encode 38 to 43 kDa cysteine rich glycoproteins having hydrophobic signal sequence, and a conserved asparagine-linked oligosaccharide consensus sequence (Shimizu et al., *Cell Growth Differ* 8 (12):1349-58 (1997)). The Wnt family contains at least 19 mammalian members. Exemplary Wnt proteins include Wnt1, Wnt2, Wnt3, Wnt3A, Wnt4, Wnt5A, Wnt5B, Wnt6, Wnt7A, Wnt7B, Wnt8A, Wnt8B, WNT10A, Wnt10B, Wnt11, Wnt12, Wnt13, Wnt14, Wnt15, and Wnt16. A preferred Wnt protein of the invention is Wnt2, preferably a human Wnt2 protein.

The terms "frizzled protein" or "frizzled receptor" refer to a family of mammalian proteins related to the *Drosophila* frizzled genes, which play a role in the development of tissue polarity. The Frizzled family comprises at least 10 mammalian genes. Exemplary human Frizzled receptors include Frizzled1, Frizzled2, Frizzled3, Frizzled4, Frizzled5, Frizzled6, Frizzled7, Frizzled8, Frizzled9 and Frizzled10. The mammalian homologues of the *Drosophila* frizzled protein share a number of common structural motifs. The N-terminus located at the extracellular membrane surface is followed by a signal sequence, a domain of 120 amino acids with an invariant pattern of 10 cysteine residues, and a highly divergent region of 40-100 largely variable hydrophilic amino acids. Putative hydrophobic segments form seven membrane-spanning helices linked by hydrophilic loops, ending with the C terminus located at the intracellular face of the membrane. The cysteine-rich domains (CRDs) and the transmembrane segments are strongly conserved, suggesting a working model in which an extracellular CRD is tethered by a variable linker region to a bundle of seven membrane-spanning helices. Frizzled protein receptors are, therefore, involved in a dynamic model of transmembrane signal transduction analogous to G-protein-coupled receptors with amino-terminal ligand binding domains. For example, Frizzled1, Frizzled2, and Frizzled7 are involved in lung and colorectal cancers, (Sagara et al., *Biochem Biophys Res Commun* 252 (1):117-22 (1998)); Frizzled3 in human cancer cells including lung, cervical and colorectal cancers, (Kirikoshi et al., *Int J Oncol* 19 (4):767-71 (2001)); Frizzled7 in gastric cancer (Kirikoshi et al., *Int J Oncol* 19 (4):767-71 (2001)); Frizzled10 in gastric and colorectal cancer, Kirikoshi et al., *Int J Oncol* 19 (4):767-71 (2001); Terasaki et al., *Int J Mol Med* 9 (2):107-12 (2002).

The terms "Disheveled" or "Dvl" refer to a member of a family of Disheveled proteins, the full-length sequences of which typically possess three conserved domains, a DIX domain, present in the Wnt antagonizing protein Axin; a PDZ domain involved in protein-protein interactions, and a DEP domain found in proteins that regulate Rho GTPases. Dvl proteins include, for example, Dvl-1, Dvl-2, and Dvl-3. Nucleic acid and protein Dvl sequence are known from a variety of species, including mouse and human. Exemplary human Dvl-1, Dvl-2, and Dvl-3 protein sequences are available under reference sequences NP_004412, NP_004413, and NM_004414, respectively.

"Inhibitors" of Wnt signaling and in particular Wnt2 signaling refers to compounds or agents that, e.g., bind to Wnt or Frizzled proteins, or partially or totally block Wnt signaling as measured in known assays for Wnt signaling (e.g., measurement of β-catenin levels, or oncogene expression controlled by Tcf and Lef transcription factors). Inhibitors, include modified versions of Wnt or Frizzled proteins, as well as naturally occurring and synthetic ligands, antagonists, agonists, antibodies, small chemical molecules, and the like. Assays for detecting inhibitors of the invention are described in more detail below.

The phrases "cell that overexpresses Wnt2 protein," "cell that overexpresses Wnt2 mRNA," "cancer cell that overexpresses Wnt2 protein" or "cancer cell that overexpresses Wnt2 mRNA" or grammatical equivalents thereof refer to a cell or cancer cell in which expression of a Wnt2 protein or Wnt2 mRNA is at least about 2 times, usually at least about 5 times the level of expression in a normal cell from the same tissue. Methods for determining the level of expression of a particular gene are well known in the art. Such methods include RT-PCR, use of antibodies against the gene products, and the like.

As used herein, "antibody" includes reference to an immunoglobulin molecule immunologically reactive with a particular antigen, and includes both polyclonal and monoclonal antibodies. The term also includes genetically engineered forms such as chimeric antibodies (e.g., humanized murine antibodies) and heteroconjugate antibodies (e.g., bispecific antibodies). The term "antibody" also includes antigen binding forms of antibodies, including fragments with antigen-binding capability (e.g., Fab', F(ab')₂, Fab, Fv and rIgG. See also, Pierce Catalog and Handbook, 1994-1995 (Pierce Chemical Co., Rockford, Ill.). See also, e.g., Kuby, J., *Immunology*, 3$^{rd}$ Ed., W.H. Freeman & Co., New York (1998). The term also refers to recombinant single chain Fv fragments (scFv). The term antibody also includes bivalent or bispecific molecules, diabodies, triabodies, and tetrabodies. Bivalent and bispecific molecules are described in, e.g., Kostelny et al. (1992) *J Immunol* 148:1547, Pack and Pluckthun (1992) *Biochemistry* 31:1579, Hollinger et al., 1993, supra, Gruber et al. (1994) *J Immunol:* 5368, Zhu et al., (1997) *Protein Sci* 6:781, Hu et al., (1996) *Cancer Res.* 56:3055, Adams et al., (1993) *Cancer Res.* 53:4026, and McCartney et al., (1995) *Protein Eng.* 8:301.

An antibody immunologically reactive with a particular antigen can be generated by recombinant methods such as selection of libraries of recombinant antibodies in phage or similar vectors, see, e.g., Huse et al., *Science* 246:1275-1281 (1989); Ward et al., *Nature* 341:544-546 (1989); and Vaughan et al., *Nature Biotech.* 14:309-314 (1996), or by immunizing an animal with the antigen or with DNA encoding the antigen.

Typically, an immunoglobulin has a heavy and light chain. Each heavy and light chain contains a constant region and a variable region, (the regions are also known as "domains"). Light and heavy chain variable regions contain four "framework" regions interrupted by three hypervariable regions, also called "complementarity-determining regions" or "CDRs." The extent of the framework regions and CDRs have been defined. The sequences of the framework regions of different light or heavy chains are relatively conserved within a species. The framework region of an antibody, that is the combined framework regions of the constituent light and heavy chains, serves to position and align the CDRs in three dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located.

Thus, a $V_H$ CDR3 is located in the variable domain of the heavy chain of the antibody in which it is found, whereas a $V_L$ CDR1 is the CDR1 from the variable domain of the light chain of the antibody in which it is found.

References to "$V_H$" or a "VH" refer to the variable region of an immunoglobulin heavy chain of an antibody, including the heavy chain of an Fv, scFv, dsFv (disulfide-stabilized Fv) or Fab. References to "$V_L$" or a "VL" refer to the variable region of an immunoglobulin light chain, including the light chain of an Fv, scFv, dsFv or Fab.

The phrase "single chain Fv" or "scFv" refers to an antibody in which the variable domains of the heavy chain and of the light chain of a traditional two chain antibody have been joined to form one chain. Typically, a linker peptide is inserted between the two chains to allow for proper folding and creation of an active binding site.

A "chimeric antibody" is an immunoglobulin molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

A "humanized antibody" is an immunoglobulin molecule which contains minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, a humanized antibody will comprise substantially all of at least one, and typically two, variable domains, in which all or substantially all of the CDR regions correspond to those of a non-human immunoglobulin and all or substantially all of the framework (FR) regions are those of a human immunoglobulin consensus sequence. The humanized antibody optimally also will comprise at least a portion of an immunoglobulin constant region (Fc), typically that of a human immunoglobulin (Jones et al., *Nature* 321:522-525 (1986); Riechmann et al., *Nature* 332:323-329 (1988); and Presta, *Curr. Op. Struct. Biol.* 2:593-596 (1992)). Humanization can be essentially performed following the method of Winter and co-workers (Jones et al., *Nature* 321:522-525 (1986); Riechmann et al., *Nature* 332:323-327 (1988); Verhoeyen et al., *Science* 239:1534-1536 (1988)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species.

The term "fully human antibody" refers to an immunoglobulin comprising human variable regions in addition to human framework and constant regions. Such antibodies can be produced using various techniques known in the art. For example in vitro methods involve use of recombinant libraries of human antibody fragments displayed on bacteriophage (e.g., McCafferty et al., 1990, *Nature* 348:552-554; Hoogenboom & Winter, J. Mol. Biol. 227:381 (1991); and Marks et al., *J. Mol. Biol.* 222:581 (1991)), yeast cells (Boder and Wittrup, 1997, *Nat Biotechnol* 15:553-557), or ribosomes (Hanes and Pluckthun, 1997, *Proc Natl Acad Sci USA* 94:4937-4942). Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, e.g., in U.S. Pat. Nos. 6,150,584; 5,545,807; 5,545,806; 5,569,825; 5,625,126; 5,633,425; 5,661,016, and in the following scientific publications: (e.g., Jakobavits, *Adv Drug Deliv Rev.* 31:33-42 (1998), Marks et al., *Bio/Technology* 10:779-783 (1992); Lonberg et al., *Nature* 368:856-859 (1994); Morrison, *Nature* 368:812-13 (1994); Fishwild et al., *Nature Biotechnology* 14:845-51 (1996); Neuberger, *Nature Biotechnology* 14:826 (1996); Lonberg & Huszar, *Intern. Rev. Immunol.* 13:65-93 (1995).

"Epitope" or "antigenic determinant" refers to a site on an antigen to which an antibody binds. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols in Methods in Molecular Biology, Vol. 66, Glenn E. Morris, Ed (1996).

"Biological sample" as used herein is a sample of biological tissue or fluid that contains nucleic acids or polypeptides, e.g., of a Wnt protein, polynucleotide or transcript. Such samples include, but are not limited to, tissue isolated from primates, e.g., humans, or rodents, e.g., mice, and rats. Biological samples may also include sections of tissues such as biopsy and autopsy samples, frozen sections taken for histologic purposes, blood, plasma, serum, sputum, stool, tears, mucus, hair, skin, etc. Biological samples also include explants and primary and/or transformed cell cultures derived from patient tissues. A biological sample is typically obtained from a eukaryotic organism, most preferably a mammal such as a primate e.g., chimpanzee or human; cow; dog; cat; a rodent, e.g., guinea pig, rat, mouse; rabbit; or a bird; reptile; or fish.

"Providing a biological sample" means to obtain a biological sample for use in methods described in this invention. Most often, this will be done by removing a sample of cells from an animal, preferably a human, but can also be accomplished by using previously isolated cells (e.g., isolated by another person, at another time, and/or for another purpose), or by performing the methods of the invention in vivo. Archival tissues, having treatment or outcome history, will be particularly useful.

The "level of Wnt2 mRNA" in a biological sample refers to the amount of mRNA transcribed from a Wnt2 gene that is present in a cell or a biological sample. The mRNA generally encodes a functional Wnt2 protein, although mutations may be present that alter or eliminate the function of the encoded protein. A "level of Wnt2 mRNA" need not be quantified, but can simply be detected, e.g., a subjective, visual detection by a human, with or without comparison to a level from a control sample or a level expected of a control sample.

The "level of Wnt2 protein or polypeptide" in a biological sample refers to the amount of polypeptide translated from Wnt2 mRNA that is present in a cell or biological sample. The polypeptide may or may not have Wnt2 protein function. A "level of Wnt2 protein" need not be quantified, but can simply be detected, e.g., a subjective, visual detection by a human, with or without comparison to a level from a control sample or a level expected of a control sample.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., Altschul et al., *Nucl. Acids Res.* 25:3389-3402 (1977) and Altschul et al., *J. Mol. Biol.* 215:403-410 (1990)). Such sequences are then said to be "substantially identical." This definition also refers to, or may be applied to, the compliment of a test sequence. The definition also includes sequences that have deletions and/or additions, as well as those that have substitutions, as well as naturally occurring, e.g., polymorphic or allelic variants, and man-made variants. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of one of the number of contiguous positions selected from the group consisting typically of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

Preferred examples of algorithms that are suitable for determining percent sequence identity and sequence similarity include the BLAST and BLAST 2.0 algorithms, which are described in Altschul et al., *Nucl. Acids Res.* 25:3389-3402 (1977) and Altschul et al., *J. Mol. Biol.* 215:403-410 (1990). BLAST and BLAST 2.0 are used, with the parameters described herein, to determine percent sequence identity for the nucleic acids and proteins of the invention. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, e.g., for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, $M=5$, $N=-4$ and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, $M=5$, $N=-4$, and a comparison of both strands.

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001. Log values may be large negative numbers, e.g., 5, 10, 20, 30, 40, 40, 70, 90, 110, 150, 170, etc.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, e.g., where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequences.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein or nucleic acid that is the predominant species present in a preparation is substantially purified. In particular, an isolated nucleic acid is separated from some open reading frames that naturally flank the gene and encode proteins other than protein encoded by the gene. The term "purified" in some embodiments denotes that a nucleic acid or protein gives rise to essentially one band in an electrophoretic gel. Preferably, it means that the nucleic acid or protein is at least 85% pure, more preferably at least 95% pure, and most preferably at least 99% pure. "Purify" or "purification" in other embodiments means removing at least one contaminant from the composition to be purified. In this sense, purification does not require that the purified compound be homogenous, e.g., 100% pure.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, e.g., an α carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical or associated, e.g., naturally contiguous, sequences. Because of the degeneracy of the genetic code, a large number of functionally identical nucleic acids encode most proteins. For instance, the codons GCA, GCC, GCG and GCU all encode the amino acid alanine. Thus, at every position where an alanine is specified by a codon, the codon can be altered to another of the corresponding codons described without altering the encoded polypeptide. Such nucleic acid variations are "silent variations," which are one species of conservatively modified variations. Every nucleic acid sequence herein which encodes a polypeptide also describes silent variations of the nucleic acid. One of skill will recognize that in certain contexts each codon in a nucleic acid (except AUG, which is ordinarily the only codon for methionine, and TGG, which is ordinarily the only codon for tryptophan) can be modified to yield a functionally identical molecule. Accordingly, often silent variations of a nucleic acid which encodes a polypeptide is implicit in a described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. Typically, conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

Macromolecular structures such as polypeptide structures can be described in terms of various levels of organization. For a general discussion of this organization, see, e.g., Alberts et al., *Molecular Biology of the Cell* (3rd ed., 1994) and Cantor & Schimmel, Biophysical Chemistry Part I: The Conformation of Biological Macromolecules (1980). "Primary structure" refers to the amino acid sequence of a particular peptide. "Secondary structure" refers to locally ordered, three dimensional structures within a polypeptide. These structures are commonly known as domains. Domains are portions of a polypeptide that often form a compact unit of the polypeptide and are typically 25 to approximately 500 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed, usually by the non-covalent association of independent tertiary units. Anisotropic terms are also known as energy terms.

A "label" or a "detectable moiety" is a composition detectable by spectroscopic, photochemical, biochemical, immunochemical, chemical, or other physical means. For example, useful labels include fluorescent dyes, electron-dense reagents, enzymes (e.g., as commonly used in an ELISA), biotin, digoxigenin, or haptens and proteins or other entities which can be made detectable, e.g., by incorporating a radiolabel into the peptide or used to detect antibodies specifically reactive with the peptide. The radioisotope may be, for example, $^3$H, $^{14}$C, $^{32}$P, $^{35}$S, or $^{125}$I. In some cases, particularly using antibodies against the proteins of the invention, the radioisotopes are used as toxic moieties, as described below. The labels may be incorporated into the nucleic acids, proteins and antibodies at any position. Any method known in the art for conjugating the antibody to the label may be employed, including those methods described by Hunter et al., *Nature*, 144:945 (1962); David et al., *Biochemistry*, 13:1014 (1974); Pain et al., *J. Immunol. Meth.*, 40:219 (1981); and Nygren, J. *Histochem. and Cytochem.*, 30:407 (1982). The lifetime of radiolabeled peptides or radiolabeled antibody compositions may extended by the addition of substances that stabilize the radiolabeled peptide or antibody and protect it from degradation. Any substance or combination of substances that stabilize the radiolabeled peptide or antibody may be used including those substances disclosed in U.S. Pat. No. 5,961,955.

An "effector" or "effector moiety" or "effector component" is a molecule that is bound (or linked, or conjugated), either covalently, through a linker or a chemical bond, or noncovalently, through ionic, van der Waals, electrostatic, or hydrogen bonds, to an antibody. The "effector" can be a variety of molecules including, e.g., detection moieties including radioactive compounds, fluorescent compounds, an enzyme or substrate, tags such as epitope tags, a toxin; activatable moieties, a chemotherapeutic agent; a lipase; an antibiotic; or a radioisotope emitting "hard" e.g., beta radiation.

The term "recombinant" when used with reference to, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, e.g., recombinant cells express genes that are not found within the native (non-recombinant) form of the cell or express native genes that are otherwise abnormally expressed, under expressed or not expressed at all. By the term "recombinant nucleic acid" herein is meant nucleic acid, originally formed in vitro, in general, by the manipulation of nucleic acid, e.g., using polymerases and endonucleases, in a form not normally found in nature. In this manner, operably linkage of different sequences is achieved. Thus an isolated nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention. Similarly, a "recombinant protein" is a protein made using recombinant techniques, i.e., through the expression of a recombinant nucleic acid as depicted above.

The term "heterologous" when used with reference to portions of a nucleic acid indicates that the nucleic acid comprises two or more subsequences that are not normally found in the same relationship to each other in nature. For instance, the nucleic acid is typically recombinantly produced, having two or more sequences, e.g., from unrelated genes arranged to make a new functional nucleic acid, e.g., a promoter from one source and a coding region from another source. Similarly, a heterologous protein will often refer to two or more subsequences that are not found in the same relationship to each other in nature (e.g., a fusion protein).

The phrase "specifically (or selectively) binds" to an antibody or antigen, such as a protein, preferably a Wnt2 protein or "specifically (or selectively) immunoreactive with," when referring to a protein or peptide or antibody, refers to a binding reaction that is determinative of the presence of the protein, in a heterogeneous population of proteins and other biologics. Thus, under designated immunoassay conditions, the specified antibodies bind to a particular protein at least two times the background and more typically more than 10 to 100 times background.

Specific binding to an antibody under such conditions requires an antibody that is selected for its specificity for a particular protein. For example, antibodies raised to a particular protein, polymorphic variants, alleles, orthologs, and conservatively modified variants, or splice variants, or portions thereof, can be selected to obtain only those antibodies that are specifically immunoreactive with Wnt2 proteins and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual (1988) for a description of immunoassay formats and conditions that can be used to determine specific immunoreactivity).

"Tumor cell" refers to precancerous, cancerous, and normal cells in a tumor.

"Cancer cell," "transformed" cell or "transformation" in tissue culture, refers to spontaneous or induced phenotypic changes that do not necessarily involve the uptake of new genetic material. Although transformation can arise from infection with a transforming virus and incorporation of new genomic DNA, or uptake of exogenous DNA, it can also arise spontaneously or following exposure to a carcinogen, thereby mutating an endogenous gene. In the present invention transformation is typically associated with overexpression of Wnt and/or Frizzled proteins. Transformation is associated with other phenotypic changes, such as immortalization of cells, aberrant growth control, nonmorphological changes, and/or malignancy (see, Freshney, *Culture of Animal Cells: A Manual of Basic Technique* (3rd ed. 1994)).

By "small interfering RNA" or "siRNA" is meant an isolated RNA molecule, preferably greater than 10 nucleotides in length, more preferably greater than 15 nucleotides in length, and most preferably 18, 19, 20, 21, 22, 23, 24, 25, 26, 27, 28, 29, or 30 nucleotides in length that has been shown to function as a key intermediate in triggering sequence-specific RNA degradation. A range of 19-25 nucleotides is the most preferred size for siRNAs. siRNAs can also include short hairpin RNAs (shRNA) in which both strands of an siRNA duplex are included within a single RNA molecule. Double-stranded siRNAs generally consist of a sense and anti-sense strand. Single-stranded siRNAs generally consist of only the antisense strand that is complementary to the target gene or mRNA. siRNA includes any form of RNA, preferably dsRNA (proteolytically cleaved products of larger dsRNA, partially purified RNA, essentially pure RNA, synthetic RNA, recombinantly produced RNA) as well as modified RNA that differs from naturally occurring RNA by the addition, deletion, substitution, and/or alteration of one or more nucleotides.

DETAILED DESCRIPTION

The role of Wnt-Fz signaling pathway in oncogenesis has been described to some extent in WO 04/032838. The present invention provides inhibitors of Wnt2 signaling pathway that can induce apoptosis in a number of cancers overexpressing Wnt2. The invention is useful for treatment of a disease associated with Wnt2 signaling, in particular a cancer in which Wnt2 signaling affects cancer cell growth or survival. The invention is particularly useful for treating cancers such as breast cancer, ovarian cancer, colorectal cancer, gastric cancer, lung cancer, kidney cancer, bladder cancer, prostate cancer, uterine cancer, thyroid cancer, pancreatic cancer, cervical cancer, esophageal cancer, mesothelioma, head and neck cancer, hepatocellular carcinoma, melanoma, brain cancer, vulval cancer, testicular cancer, sarcoma, intestine cancer, skin cancer, leukemia, and lymphoma cancer.

Blocking Wnt2 signaling is shown here to lead to downregulation of downstream components of the Wnt-Fz pathway, in particular, Disheveled (Dvl) and β-catenin. This invention also shows that antibody-induced apoptosis occurs through activation of JNK, releasing Smac/Diablo and cytochrome C from mitochondria to the cytosol. Cytochrome C inactivates survivin, an inhibitor of apoptosis, that leads to the activation of caspases. The invention further provides anti-Wnt2 monoclonal antibodies that suppress growth of tumors in vivo.

I. ANTI-WNT2 ANTIBODIES

As noted above, the invention provides methods of inhibiting Wnt2 signaling in cells overexpressing Wnt2, preferably cancer cells. In some embodiments of the invention, antibodies are used to block the binding between Wnt2 ligand and the Frizzled receptor. The antibodies can be raised against either Wnt2 or Frizzled proteins.

A. Generation of Anti Wnt2 Monoclonal Antibodies

Antibodies that may be used in the methods, pharmaceutical compositions and kits of the present invention may be polyclonal anti-Wnt2 antibodies or monoclonal anti-Wnt2 antibodies. Preferably, the antibodies are monoclonal anti-Wnt2 antibodies. Monoclonal antibodies of the invention may be prepared in a variety of ways. A preferred method uses hybridoma methods, such as those described by Köhler & Milstein, *Nature* 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

An immunizing agent may comprise a Wnt2 polypeptide as shown in SEQ ID NOS:1-15 and SEQ ID NOS:30-53. A preferred human Wnt2 peptide sequence for generating an anti Wnt2 monoclonal antibody is SSQRQLCHRHPDVMR (SEQ ID NO:2), a peptide that consists of amino acid residues 49-63 of human Wnt2 as shown in SEQ ID NO:1 or amino acid residues 24-38 of mature human Wnt2, i.e., after cleavage of the signal peptide (amino acid residues 1-25 of SEQ ID NO:1).

Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, Monoclonal Antibodies: Principles and Practice, pp. 59-103 (1986)). Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Several anti-Wnt2 monoclonal antibodies can be generated using the method described herein. In a preferred embodiment of the invention, a Wnt2 monoclonal antibody comprises a (i) a $V_L$CDR1 amino acid sequence as shown in SEQ ID NO:56, SEQ ID NO:104 or SEQ ID NO:125; (ii) a $V_L$CDR2 amino acid sequence as shown in SEQ ID NO:58; (iii) a $V_L$CDR3 amino acid sequence as shown in SEQ ID NO:60, SEQ ID NO:84, SEQ ID NO:107, SEQ ID NO:126 or SEQ ID NO:138; (iv) a $V_H$CDR1 amino acid sequence as shown in SEQ ID NO:63 or SEQ ID NO:87; (v) a $V_H$CDR2 amino acid sequence as shown in SEQ ID NO:65 or SEQ ID NO:89; or (vi) a $V_H$CDR3 amino acid sequence as shown in SEQ ID NO:67, SEQ ID NO:91 or SEQ ID NO:110.

In another preferred embodiment of the invention, a Wnt2 monoclonal antibody comprises a (i) a $V_L$CDR1 amino acid sequence as shown in SEQ ID NO:56, SEQ ID NO:104 or SEQ ID NO:125; (ii) a $V_L$CDR2 amino acid sequence as shown in SEQ ID NO:58; (iii) a $V_L$CDR3 amino acid sequence as shown in SEQ ID NO:60, SEQ ID NO:84, SEQ ID NO:107, SEQ ID NO:126 or SEQ ID NO:138; (iv) a $V_H$CDR1 amino acid sequence as shown in SEQ ID NO:63 or SEQ ID NO:87; (v) a $V_H$CDR2 amino acid sequence as shown in SEQ ID NO:65 or SEQ ID NO:89; and (vi) a $V_H$CDR3 amino acid sequence as shown in SEQ ID NO:67, SEQ ID NO:91 or SEQ ID NO:110.

In yet another preferred embodiment of the present invention, exemplified by anti-Wnt2 monoclonal antibodies 17F7.G7 (subclone B, Chain 1, FIG. 18) and 8B11.H6 (Chain 1, FIG. 17), a monoclonal Wnt2 antibody comprises a (i) a $V_L$CDR1 amino acid sequence as shown in SEQ ID NO:56; (ii) a $V_L$CDR2 amino acid sequence as shown in SEQ ID NO:58; and (iii) a $V_L$CDR3 amino acid sequence as shown in SEQ ID NO:84. As further exemplified by 17F7.G7 (subclone B, Chain 2, FIG. 18), a monoclonal Wnt2 antibody comprises (i) a $V_L$CDR1 amino acid sequence as shown in SEQ ID NO:104; (ii) a $V_L$CDR2 amino acid sequence as shown in SEQ ID NO:58; and (iii) a $V_L$CDR3 amino acid sequence as shown in SEQ ID NO:138. As exemplified by 17F7.G7 (subclone B, FIG. 18), a monoclonal Wnt2 antibody may also comprises (i) a $V_H$CDR1 amino acid sequence as shown in SEQ ID NO:63; (ii) a $V_H$CDR2 amino acid sequence as shown in SEQ ID NO:65; and (iii) a $V_H$CDR3 amino acid sequence as shown in SEQ ID NO:110. As further exemplified by 17F7.G7 (subclone B, FIG. 18), the anti-Wnt2 monoclonal antibody may comprise (i) a $V_L$CDR1 amino acid sequence as shown in SEQ ID NO:56; (ii) a $V_L$CDR2 amino acid sequence as shown in SEQ ID NO:58; (iii) a $V_L$CDR3 amino acid sequence as shown in SEQ ID NO:84; (iv) a $V_H$CDR1 amino acid sequence as shown in SEQ ID NO:63; (v) a $V_H$CDR2 amino acid sequence as shown in SEQ ID NO:65; and (vi) a $V_H$CDR3 amino acid sequence as shown in SEQ ID NO:110. Another anti-Wnt2 monoclonal antibody comprises (i) a $V_L$CDR1 amino acid sequence as shown in SEQ ID NO:104; (ii) a $V_L$CDR2 amino acid sequence as shown in SEQ ID NO:58; (iii) a $V_L$CDR3 amino acid sequence as shown in SEQ ID NO:138; (iv) a $V_H$CDR1 amino acid sequence as shown in SEQ ID NO:63; (v) a $V_H$CDR2 amino acid sequence as shown in SEQ ID NO:65; and (vi) a $V_H$CDR3 amino acid sequence as shown in SEQ ID NO:110.

Another preferred anti-Wnt2 monoclonal antibody, exemplified by anti-Wnt2 monoclonal antibody 17F7.E5 (FIG. 16) comprises a (i) a $V_L$CDR1 amino acid sequence as shown in SEQ ID NO:104; (ii) a $V_L$CDR2 amino acid sequence as shown in SEQ ID NO:58; and (iii) a $V_L$CDR3 amino acid sequence as shown in SEQ ID NO:107. In another embodiment of the present invention, an anti-Wnt2 monoclonal antibody comprises (i) a $V_L$CDR1 amino acid sequence as shown in SEQ ID NO:104; (ii) a $V_L$CDR2 amino acid sequence as shown in SEQ ID NO:58; (iii) a $V_L$CDR3 amino acid sequence as shown in SEQ ID NO:107; (iv) a $V_H$CDR1 amino acid sequence as shown in SEQ ID NO:63; (v) a $V_H$CDR2 amino acid sequence as shown in SEQ ID NO:65; and (vi) a $V_H$CDR3 amino acid sequence as shown in SEQ ID NO:110.

Another preferred anti-Wnt2 monoclonal antibody, exemplified by anti-Wnt2 monoclonal antibody 8B11.D2 (FIG. 15) comprises (i) a $V_L$CDR1 amino acid sequence as shown in SEQ ID NO:56; (ii) a $V_L$CDR2 amino acid sequence as shown in SEQ ID NO:58; and (iii) a $V_L$CDR3 amino acid sequence as shown in SEQ ID NO:84. As exemplified by anti-Wnt2 monoclonal antibodies 8B11.D2 (FIG. 15) and 8B11.H6 (Chain 1, FIG. 17), an anti-Wnt2 monoclonal antibody may also comprise (i) a $V_H$CDR1 amino acid sequence as shown in SEQ ID NO:87; (ii) a $V_H$CDR2 amino acid sequence as shown in SEQ ID NO:89; and (iii) a $V_H$CDR3 amino acid sequence as shown in SEQ ID NO:91. In yet another embodiment of the present invention, an anti-Wnt2 monoclonal antibody comprises (i) a $V_L$CDR1 amino acid sequence as shown in SEQ ID NO:56; (ii) a $V_L$CDR2 amino acid sequence as shown in SEQ ID NO:58; (iii) a $V_L$CDR3 amino acid sequence as shown in SEQ ID NO:84; (iv) a $V_H$CDR1 amino acid sequence as shown in SEQ ID NO:87; (v) a $V_H$CDR2 amino acid sequence as shown in SEQ ID NO:89; and (vi) a $V_H$CDR3 amino acid sequence as shown in SEQ ID NO:91.

In yet another preferred embodiment of the present invention, exemplified by anti-Wnt2 monoclonal antibody 8B11.H6 (Chain 1, FIG. 17), an anti-Wnt2 monoclonal antibody comprises (i) a $V_L$CDR1 amino acid sequence as shown in SEQ ID NO:56; (ii) a $V_L$CDR2 amino acid sequence as shown in SEQ ID NO:58; (iii) a $V_L$CDR3 amino acid sequence as shown in SEQ ID NO:84; (iv) a $V_H$CDR1 amino acid sequence as shown in SEQ ID NO:87; (v) a $V_H$CDR2 amino acid sequence as shown in SEQ ID NO:89; and (vi) a $V_H$CDR3 amino acid sequence as shown in SEQ ID NO:91. Another preferred anti-Wnt2 monoclonal antibody, exemplified by 8B11.H6 (Chain 2, FIG. 17), comprises (i) a $V_L$CDR1 amino acid sequence as shown in SEQ ID NO:125; (ii) a $V_L$CDR2 amino acid sequence as shown in SEQ ID NO:58; and (iii) a $V_L$CDR3 amino acid sequence as shown in SEQ ID NO:126. Another Wnt-2 monoclonal antibody comprises (i) a $V_L$CDR1 amino acid sequence as shown in SEQ ID NO:125; (ii) a $V_L$CDR2 amino acid sequence as shown in SEQ ID NO:58; and (iii) a $V_L$CDR3 amino acid sequence as shown in SEQ ID NO:126; (iv) a $V_H$CDR1 amino acid sequence as shown in SEQ ID NO:87; (v) a $V_H$CDR2 amino acid sequence as shown in SEQ ID NO:89; and (vi) a $V_H$CDR3 amino acid sequence as shown in SEQ ID NO:91.

As disclosed herein, anti-Wnt2 antibodies may be generated using a Wnt2 peptide comprising any of the amino acid sequences of SEQ ID NOS:1-15 and 30-53. A preferred anti-Wnt2 antibody is an antibody that specifically binds to a polypeptide comprising an amino acid sequence corresponding to amino acid residues 49-63 of human Wnt2 (SEQ ID NO:2). The phrase "corresponding to amino acid residues 49-63 of human Wnt2 (SEQ ID NO:2)" refers to an amino acid sequence of a non-human Wnt2 protein or another Wnt protein, wherein the respective amino acid sequence corresponds to amino acid residues 49-63 of human Wnt2 (SEQ ID NO:2). These amino acid sequences may have one or more amino acid differences when compared to amino acid residues 49-63 of human Wnt2 (SEQ ID NO:2). In a preferred embodiment of the present invention, an anti-Wnt2 antibody specifically binds a polypeptide comprising SSQRQLCHRPDVMR (SEQ ID NO:2), and in particular binds to the SSQRQLCHRPDVMR (SEQ ID NO:2) epitope of the polypeptide.

B. Nucleic Acids Encoding Anti-Wnt2 Antibodies

Anti-Wnt2 antibodies of the present invention can be prepared in a variety of ways. In one aspect of the present invention, anti-Wnt2 antibodies are produced recombinantly. In this method, the anti-Wnt2 antibody is encoded by a nucleic acid that is inserted into an expression vector and expressed in a suitable host as known in the art.

In a preferred embodiment of the present invention, the nucleic acid encoding an anti-Wnt2 monoclonal antibody comprises a nucleic acid comprising (i) a nucleic acid encoding a $V_L$CDR1 selected from the group consisting of nucleic acid sequences shown in SEQ ID NO:70, SEQ ID NO:113 and SEQ ID NO:131; (ii) a nucleic acid encoding a $V_L$CDR2 selected from the group consisting of nucleic acid sequences shown in SEQ ID NO:72 and SEQ ID NO:115; (iii) a nucleic acid encoding a $V_L$CDR3 selected from the group of nucleic acid sequences shown in SEQ ID NO:94, SEQ ID NO:117, SEQ ID NO:134 and SEQ ID NO:143; (iv) a nucleic acid encoding a $V_H$CDR1 selected from the group of nucleic acid sequences shown in SEQ ID NO:77 and SEQ ID NO:97; (v) a nucleic acid encoding a $V_H$CDR2 selected from the group of nucleic acid sequences shown in SEQ ID NO:79 and SEQ ID NO:99; and (vi) a nucleic acid encoding a $V_H$CDR3 selected from the group of nucleic acid sequences shown in SEQ ID NO:101 and SEQ ID NO:120.

In yet another preferred embodiment of the present invention, as exemplified by anti-Wnt2 monoclonal antibodies 8B11.D2 and 8B11.H6 (light chain kappa, Chain 1), a nucleic acid encoding an anti-Wnt2 monoclonal antibody comprises a nucleic acid comprising (i) a nucleic acid encoding a $V_L$CDR1 as shown in SEQ ID NO:70; (ii) a nucleic acid encoding a $V_L$CDR2 as shown in SEQ ID NO:72; and (iii) a nucleic acid encoding a $V_L$CDR3 as shown in SEQ ID NO:94. A nucleic acid encoding an anti-Wnt2 monoclonal antibody may also comprise (i) a nucleic acid encoding a $V_H$CDR1 as shown in SEQ ID NO:97; (ii) a nucleic acid encoding a $V_H$CDR2 as shown in SEQ ID NO:99; and (iii) a nucleic acid encoding a $V_H$CDR3 as shown in SEQ ID NO:101. In a preferred embodiment of the present invention, a nucleic acid encoding an anti-Wnt2 monoclonal antibody comprises a nucleic acid comprising (i) a nucleic acid encoding a $V_L$CDR1 as shown in SEQ ID NO:70; (ii) a nucleic acid encoding a $V_L$CDR2 as shown in SEQ ID NO:72; and (iii) a nucleic acid encoding a $V_L$CDR3 as shown in SEQ ID NO:94; (iv) a nucleic acid encoding a $V_H$CDR1 as shown in SEQ ID NO:97; (v) a nucleic acid encoding a $V_H$CDR2 as shown in SEQ ID NO:99; and (vi) a nucleic acid encoding a $V_H$CDR3 as shown in SEQ ID NO:101.

Another preferred nucleic acid encoding an anti-Wnt2 monoclonal antibody as exemplified by anti-Wnt2 monoclonal antibody 8B11.H6 (light chain kappa, Chain 2), a nucleic acid encoding an anti-Wnt2 monoclonal antibody comprises a nucleic acid comprising (i) a nucleic acid encoding a $V_L$CDR1 as shown in SEQ ID NO:131; (ii) a nucleic acid encoding a $V_L$CDR2 as shown in SEQ ID NO:115; and (iii) a nucleic acid encoding a $V_L$CDR3 as shown in SEQ ID NO:134. In a preferred embodiment of the present invention, a nucleic acid encoding an anti-Wnt2 monoclonal antibody comprises a nucleic acid comprising (i) a nucleic acid encoding a $V_L$CDR1 as shown in SEQ ID NO:131; (ii) a nucleic acid encoding a $V_L$CDR2 as shown in SEQ ID NO:115; and (iii) a nucleic acid encoding a $V_L$CDR3 as shown in SEQ ID NO:134; (iv) a nucleic acid encoding a $V_H$CDR1 as shown in SEQ ID NO:97; (v) a nucleic acid encoding a $V_H$CDR2 as shown in SEQ ID NO:99; and (vi) a nucleic acid encoding a $V_H$CDR3 as shown in SEQ ID NO:101.

In yet another preferred embodiment of the present invention, as exemplified by anti-Wnt2 monoclonal antibody 17F7.G7 (subclone B, Chain 1), a nucleic acid encoding an anti-Wnt2 monoclonal antibody comprises a nucleic acid comprising (i) a nucleic acid encoding a $V_L$CDR1 as shown in SEQ ID NO:70; (ii) a nucleic acid encoding a V$_L$CDR2 as shown in SEQ ID NO:72; and (iii) a nucleic acid encoding a V$_L$CDR3 as shown in SEQ ID NO:94. As exemplified by anti-Wnt2 monoclonal antibody 17F7.G7 (subclone B, Chain 2), a nucleic acid encoding an anti-Wnt2 monoclonal antibody comprises a nucleic acid comprising (i) a nucleic acid encoding a V$_L$CDR1 as shown in SEQ ID NO:113; (ii) a nucleic acid encoding a V$_L$CDR2 as shown in SEQ ID NO:115; and (iii) a nucleic acid encoding a V$_L$CDR3 as shown in SEQ ID NO:143. A nucleic acid encoding an anti-Wnt2 monoclonal antibody may also comprise (i) a nucleic acid encoding a V$_H$CDR1 as shown in SEQ ID NO:77; (ii) a nucleic acid encoding a V$_H$CDR2 as shown in SEQ ID NO:79; and (iii) a nucleic acid encoding a V$_H$CDR3 as shown in SEQ ID NO:120. In a preferred embodiment of the present invention, a nucleic acid encoding an anti-Wnt2 monoclonal antibody comprises a nucleic acid comprising (i) a nucleic acid encoding a V$_L$CDR1 as shown in SEQ ID NO:70; (ii) a nucleic acid encoding a V$_L$CDR2 as shown in SEQ ID NO:72; (iii) a nucleic acid encoding a V$_L$CDR3 as shown in SEQ ID NO:94; (iv) a nucleic acid encoding a V$_H$CDR1 as shown in SEQ ID NO:77; (v) a nucleic acid encoding a V$_H$CDR2 as shown in SEQ ID NO:79; and (vi) a nucleic acid encoding a V$_H$CDR3 as shown in SEQ ID NO:120. Another preferred nucleic acid encoding an anti-Wnt2 monoclonal antibody comprises a nucleic acid comprising (i) a nucleic acid encoding a V$_L$CDR1 as shown in SEQ ID NO:113; (ii) a nucleic acid encoding a V$_L$CDR2 as shown in SEQ ID NO:115; and (iii) a nucleic acid encoding a V$_L$CDR3 as shown in SEQ ID NO:143; (iv) a nucleic acid encoding a V$_H$CDR1 as shown in SEQ ID NO:77; (v) a nucleic acid encoding a V$_H$CDR2 as shown in SEQ ID NO:79; and (vi) a nucleic acid encoding a V$_H$CDR3 as shown in SEQ ID NO:120.

In yet another preferred embodiment of the present invention, as exemplified by anti-Wnt2 monoclonal antibody 17F7.E5, a nucleic acid encoding an anti-Wnt2 monoclonal antibody comprises a nucleic acid comprising (i) a nucleic acid encoding a V$_L$CDR1 as shown in SEQ ID NO:113; (ii) a nucleic acid encoding a V$_L$CDR2 as shown in SEQ ID NO: 115; and (iii) a nucleic acid encoding a V$_L$CDR3 as shown in SEQ ID NO:117. A nucleic acid encoding an anti-Wnt2 monoclonal antibody may also comprise (i) a nucleic acid encoding a V$_H$CDR1 as shown in SEQ ID NO:77; (ii) a nucleic acid encoding a V$_H$CDR2 as shown in SEQ ID NO:79; and (iii) a nucleic acid encoding a V$_H$CDR3 as shown in SEQ ID NO:120. In a preferred embodiment of the present invention, a nucleic acid encoding an anti-Wnt2 monoclonal antibody comprises a nucleic acid comprising (i) a nucleic acid encoding a V$_L$CDR1 as shown in SEQ ID NO:113; (ii) a nucleic acid encoding a V$_L$CDR2 as shown in SEQ ID NO:115; (iii) a nucleic acid encoding a V$_L$CDR3 as shown in SEQ ID NO:117; (iv) a nucleic acid encoding a V$_H$CDR1 as shown in SEQ ID NO:77; (v) a nucleic acid encoding a V$_H$CDR2 as shown in SEQ ID NO:79; and (vi) a nucleic acid encoding a V$_H$CDR3 as shown in SEQ ID NO:120.

C. Generation of Recombinant Anti-Wnt2 Antibodies

Using the nucleic acids of the invention, anti Wnt2 monoclonal antibodies can be produced recombinantly. In a preferred embodiment, a chimeric or humanized anti-Wnt2 monoclonal antibody is produced recombinantly. Recombinant DNA technology may be employed wherein a nucleotide sequence that encodes an anti-Wnt2 monoclonal antibody or a fragment thereof, such as one or more CDR sequences, is inserted into an expression vector, transformed or transfected into an appropriate host cell and cultivated under conditions suitable for expression. These procedures are generally known in the art, as described generally in Sambrook et al., *Molecular Cloning, A Laboratory Manual*, Cold Spring Harbor Press, Cold Spring Harbor, N.Y. (1982), which is incorporated herein by reference. "Vector" refers to any type of genetic construct containing a nucleic acid capable of being transcribed in a cell. Vectors used for the amplification of nucleotide sequences (both coding and non-coding) are also encompassed by the definition. In addition to the coding sequence, vectors will generally include restriction enzyme cleavage sites and the other initial, terminal and intermediate DNA sequences that are usually employed in vectors to facilitate their construction and use. The expression vector can be part of a plasmid, virus, or nucleic acid fragment. "Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-o-methyl ribonucleotides and peptide-nucleic acids (PNAs).

Coding sequences for the anti-Wnt2 monoclonal antibodies of the present invention or fragments and CDR sequences thereof may be synthesized by chemical techniques, for example, the phosphotriester method of Matteucci et al. (*J Am Chem. Soc.* 1981, 103:3185). The term "coding sequence", in relation to nucleic acid sequences, refers to a plurality of contiguous sets of three nucleotides, termed codons, each codon corresponding to an amino acid as translated by biochemical factors according to the universal genetic code, the entire sequence coding for an expressed protein, or an antisense strand that inhibits expression of a protein. A "genetic coding sequence" is a coding sequence where the contiguous codons are intermittently interrupted by non-coding intervening sequences, or "introns." During mRNA processing intron sequences are removed, restoring the contiguous codon sequence encoding the protein.

Any modification within a DNA or RNA sequence can be made simply by substituting the appropriate bases for those encoding the desired amino acid sequence. The coding sequence can then be provided with appropriate linkers and ligated into expression vectors commonly available in the art, and the vectors used to transform suitable hosts to produce the immunostimulating peptide or protein. A number of such vectors and suitable host systems are commercially available. For expression, the coding sequence will be provided with operably linked start and stop codons, promoter and terminator regions and usually a replication system to provide an expression vector for expression in the desired cellular host. For example, promoter sequences compatible with bacterial hosts are provided in plasmids containing convenient restriction sites for insertion of the desired coding sequence. The resulting expression vectors are transformed into suitable bacterial hosts. Of course, yeast or mammalian cell hosts may also be used, employing suitable vectors and control sequences as known to the skilled artisan.

D. Chimeric and Humanized Anti-Wnt-2 Antibodies

In some embodiments of the invention the anti-Wnt2 antibodies are chimeric or humanized antibodies. As noted above, humanized forms of antibodies are chimeric immunoglobulins in which residues from a complementary determining region (CDR) of human antibody are replaced by residues from a CDR of a non-human species such as mouse, rat or rabbit having the desired specificity, affinity and capacity. Preferred mouse $V_L$CDR and $V_H$CDR sequences are shown in Table 2.

In a preferred embodiment of the present invention, a chimeric or humanized anti-Wnt2 antibody comprises (i) a $V_L$CDR1 amino acid sequence as shown in SEQ ID NO:56, SEQ ID NO:104 or SEQ ID NO:125; (ii) a $V_L$CDR2 amino acid sequence as shown in SEQ ID NO:58; (iii) a $V_L$CDR3 amino acid sequence as shown in SEQ ID NO:60, SEQ ID NO:84, SEQ ID NO:107, SEQ ID NO:126 or SEQ ID NO:138; (iv) a $V_H$CDR1 amino acid sequence as shown in SEQ ID NO:63, or SEQ ID NO:87; (v) a $V_H$CDR2 amino acid sequence as shown in SEQ ID NO:65 or SEQ ID NO:89; or (vi) a $V_H$CDR3 amino acid sequence as shown in SEQ ID NO:67, SEQ ID NO:91 or SEQ ID NO:110.

In another preferred embodiment of the present invention, a chimeric or humanized anti-Wnt2 antibody comprises (i) a $V_L$CDR1 amino acid sequence as shown in SEQ ID NO:56, SEQ ID NO:104 or SEQ ID NO:125; (ii) a $V_L$CDR2 amino acid sequence as shown in SEQ ID NO:58; (iii) a $V_L$CDR3 amino acid sequence as shown in SEQ ID NO:60, SEQ ID NO:84, SEQ ID NO:107, SEQ ID NO:126 or SEQ ID NO:138; (iv) a $V_H$CDR1 amino acid sequence as shown in SEQ ID NO:63, or SEQ ID NO:87; (v) a $V_H$CDR2 amino acid sequence as shown in SEQ ID NO:65 or SEQ ID NO:89; and (vi) a $V_H$CDR3 amino acid sequence as shown in SEQ ID NO:67, SEQ ID NO:91 or SEQ ID NO:110.

Other preferred embodiments of chimeric or humanized anti-Wnt2 antibody comprise combinations of $V_L$CDRs and $V_H$CDRs as described herein and as exemplified by the anti-Wnt2 monoclonal antibodies 17F7.G7 (subclone B, Chains 1 and 2, FIG. 18), 8B11.H6 (Chains 1 and 2, FIG. 17), 17F7.E5 (FIG. 16), and 8B11.D2 (FIG. 15).

Human antibodies can be produced using various techniques known in the art, including phage display libraries (Hoogenboom & Winter, *J. Mol. Biol.* 227:381 (1991); Marks et al., *J. Mol. Biol.* 222:581 (1991)). The techniques of Cole et al. and Boerner et al. are also available for the preparation of human monoclonal antibodies (Cole et al., *Monoclonal Antibodies and Cancer Therapy*, p. 77 (1985) and Boerner et al., *J. Immunol.* 147 (1):86-95 (1991)). Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, e.g., in U.S. Pat. Nos. 5,545,807; 5,545,806; 5,569,825; 5,625,126; 5,633,425; 5,661,016, and in the following scientific publications: Marks et al., *Bio/Technology* 10:779-783 (1992); Lonberg et al., *Nature* 368:856-859 (1994); Morrison, Nature 368:812-13 (1994); Fishwild et al., *Nature Biotechnology* 14:845-51 (1996); Neuberger, *Nature Biotechnology* 14:826 (1996); Lonberg & Huszar, *Intern. Rev. Immunol.* 13:65-93 (1995).

E. Single Chain Fv Antibodies Binding Wnt2

In some embodiments, the antibody is a single chain Fv (scFv). The $V_H$ and the $V_L$ regions of a scFv antibody comprise a single chain which is folded to create an antigen binding site similar to that found in two chain antibodies. Once folded, noncovalent interactions stabilize the single chain antibody. While the $V_H$ and $V_L$ regions of some antibody embodiments can be directly joined together, one of skill will appreciate that the regions may be separated by a peptide linker consisting of one or more amino acids. Peptide linkers and their use are well-known in the art. See, e.g., Huston et al., *Proc. Nat'l Acad. Sci. USA* 8:5879 (1988); Bird et al., *Science* 242:4236 (1988); Glockshuber et al., *Biochemistry* 29:1362 (1990); U.S. Pat. No. 4,946,778, U.S. Pat. No. 5,132,405 and Stemmer et al., *Biotechniques* 14:256-265 (1993). Generally the peptide linker will have no specific biological activity other than to join the regions or to preserve some minimum distance or other spatial relationship between the $V_H$ and $V_L$. However, the constituent amino acids of the peptide linker may be selected to influence some property of the molecule such as the folding, net charge, or hydrophobicity. Single chain Fv (scFv) antibodies optionally include a peptide linker of no more than 50 amino acids, generally no more than 40 amino acids, preferably no more than 30 amino acids, and more preferably no more than 20 amino acids in length. In some embodiments, the peptide linker is a concatamer of the sequence Gly-Gly-Gly-Gly-Ser, preferably 2, 3, 4, 5, or 6 such sequences. However, it is to be appreciated that some amino acid substitutions within the linker can be made. For example, a valine can be substituted for a glycine.

In a preferred embodiment of the present invention the $V_L$ region of the scFv comprises (i) a $V_L$CDR1 amino acid sequence as shown in SEQ ID NO:56, SEQ ID NO:104 or SEQ ID NO:125; (ii) a $V_L$CDR2 amino acid sequence as shown in SEQ ID NO:58; (iii) a $V_L$CDR3 amino acid sequence as shown in SEQ ID NO:60, SEQ ID NO:84, SEQ ID NO:107, SEQ ID NO:126 or SEQ ID NO:138. The $V_H$ region of the scFv may comprise (i) a $V_H$CDR1 amino acid sequence as shown in SEQ ID NO:63 or SEQ ID NO:87; (ii) a $V_H$CDR2 amino acid sequence as shown in SEQ ID NO:65 or SEQ ID NO:89; or (iii) a $V_H$CDR3 amino acid sequence as shown in SEQ ID NO:67, SEQ ID NO:91 or SEQ ID NO:110.

Methods of making scFv antibodies have been described. See, Huse et al., supra; Ward et al. supra; and Vaughan et al., supra. In brief, mRNA from B-cells from an immunized animal is isolated and cDNA is prepared. The cDNA is amplified using primers specific for the variable regions of heavy and light chains of immunoglobulins. The PCR products are purified and the nucleic acid sequences are joined. If a linker peptide is desired, nucleic acid sequences that encode the peptide are inserted between the heavy and light chain nucleic acid sequences. The nucleic acid which encodes the scFv is inserted into a vector and expressed in the appropriate host cell. The scFv that specifically bind to the desired antigen are typically found by panning of a phage display library. Panning can be performed by any of several methods. Panning can conveniently be performed using cells expressing the desired antigen on their surface or using a solid surface coated with the desired antigen. Conveniently, the surface can be a magnetic bead. The unbound phage are washed off the solid surface and the bound phage are eluted.

Regardless of the method of panning chosen, the physical link between genotype and phenotype provided by phage display makes it possible to test every member of a cDNA library for binding to antigen, even with large libraries of clones.

F. Bispecific and Conjugated Anti-Wnt2 Antibodies

In some embodiments, the antibodies are bispecific antibodies. Bispecific antibodies are monoclonal, preferably human or humanized, antibodies that have binding specificities for at least two different antigens or that have binding specificities for two epitopes on the same antigen. In one embodiment, one of the binding specificities is for the Wnt2 protein, the other one is for another cancer antigen. Alternatively, tetramer-type technology may create multivalent reagents.

In some embodiments, the antibody is conjugated to an effector moiety. The effector moiety can be any number of molecules, including labeling moieties such as radioactive labels or fluorescent labels, or can be a therapeutic moiety. If the effector moiety is a therapeutic moiety, it will typically be a cytotoxic agent. In this method, targeting the cytotoxic agent to cancer cells, results in direct killing of the target cell. This embodiment is typically carried out using antibodies against the Frizzled receptor. Cytotoxic agents are numerous and varied and include, but are not limited to, cytotoxic drugs or toxins or active fragments of such toxins. Suitable toxins and their corresponding fragments include diphtheria A chain, exotoxin A chain, ricin A chain, abrin A chain, curcin, crotin, phenomycin, enomycin, auristatin and the like. Cytotoxic agents also include radiochemicals made by conjugating radioisotopes to antibodies raised against Wnt2 proteins, or binding of a radionuclide to a chelating agent that has been covalently attached to the antibody.

G. Binding Affinity of Antibodies of the Invention

Binding affinity for a target antigen is typically measured or determined by standard antibody-antigen assays, such as Biacore competitive assays, saturation assays, or immunoassays such as ELISA or RIA.

Such assays can be used to determine the dissociation constant of the antibody. The phrase "dissociation constant" refers to the affinity of an antibody for an antigen. Specificity of binding between an antibody and an antigen exists if the dissociation constant ($K_D$=1/K, where K is the affinity constant) of the antibody is <1 µM, preferably <100 nM, and most preferably <0.1 nM. Antibody molecules will typically have a $K_D$ in the lower ranges. $K_D$=[Ab-Ag]/[Ab][Ag] where [Ab] is the concentration at equilibrium of the antibody, [Ag] is the concentration at equilibrium of the antigen and [Ab-Ag] is the concentration at equilibrium of the antibody-antigen complex. Typically, the binding interactions between antigen and antibody include reversible noncovalent associations such as electrostatic attraction, Van der Waals forces and hydrogen bonds.

The antibodies of the invention specifically bind to Wnt2 proteins. By "specifically bind" herein is meant that the antibodies bind to the Wnt2 protein with a $K_D$ of at least about 0.1 mM, more usually at least about 1 µM, preferably at least about 0.1 µM or better, and most preferably, 0.01 µM or better.

H. Competitive Binding of Anti-Wnt2 Monoclonal Antibodies

In some embodiments, an anti-Wnt2 monoclonal antibody is used. A preferred embodiment is an anti-Wnt2 monoclonal antibody that binds the same epitope as a second anti-Wnt2 antibody. The ability of a particular antibody to recognize the same epitope as another antibody is typically determined by the ability of one antibody to competitively inhibit binding of the second antibody to the antigen. Any of a number of competitive binding assays can be used to measure competition between two antibodies to the same antigen. For example, a sandwich ELISA assay can be used for this purpose. This is carried out by using a capture antibody to coat the surface of a well. A subsaturating concentration of tagged-antigen is then added to the capture surface. This protein will be bound to the antibody through a specific antibody:epitope interaction. After washing a second antibody, which has been covalently linked to a detectable moeity (e.g., HRP, with the labeled antibody being defined as the detection antibody) is added to the ELISA. If this antibody recognizes the same epitope as the capture antibody it will be unable to bind to the target protein as that particular epitope will no longer be available for binding. If however this second antibody recognizes a different epitope on the target protein it will be able to bind and this binding can be detected by quantifying the level of activity (and hence antibody bound) using a relevant substrate. The background is defined by using a single antibody as both capture and detection antibody, whereas the maximal signal can be established by capturing with an antigen specific antibody and detecting with an antibody to the tag on the antigen. By using the background and maximal signals as references, antibodies can be assessed in a pair-wise manner to determine epitope specificity.

A first antibody is considered to competitively inhibit binding of a second antibody, if binding of the second antibody to the antigen is reduced by at least 30%, usually at least about 40%, 50%, 60% or 75%, and often by at least about 90%, in the presence of the first antibody using any of the assays described above.

II. ASSAYS FOR DETECTING LEVELS OF WNT2 EXPRESSION

The present invention also provides diagnostic assays for detecting Wnt2. In preferred embodiments, activity of the Wnt2 gene is determined by a measure of gene transcript (e.g. mRNA), by a measure of the quantity of translated protein, or by a measure of gene product activity.

Methods of detecting and/or quantifying the gene transcript (mRNA or cDNA) using nucleic acid hybridization techniques are known to those of skill in the art. For example, one method for evaluating the presence, absence, or quantity of mRNA involves a Northern blot transfer.

The probes can be full length or less than the full length of the nucleic acid sequence encoding the Wnt2 protein. Probes usually are labeled with, for example, radionucleotides or biotin and can be generated by nick translation, random or specific priming as known in the art. Hybridization conditions are also described in the art. These procedures are generally known in the art, as described generally in Sambrook et al., *Molecular Cloning, A Laboratory Manual*, Cold Spring Harbor Press, Cold Spring Harbor, N.Y. (1982). Shorter probes are empirically tested for specificity. Preferably nucleic acid probes are 20 bases or longer in length. Visualization of the hybridized portions allows the qualitative determination of the presence or absence of mRNA.

In another preferred embodiment, a transcript (e.g., mRNA) can be measured using amplification (e.g. PCR) based methods as described above for directly assessing copy number of DNA or mRNA. In a preferred embodiment, transcript level is assessed by using reverse transcription PCR (RT-PCR). Primer pairs useful in such methods are disclosed in SEQ ID NOS:16-29.

The "activity" of the Wnt2 gene can also be detected and/or quantified by detecting or quantifying the expressed polypeptide. The polypeptide can be detected and quantified by any of a number of means well known to those of skill in the art. These may include analytic biochemical methods such as electrophoresis, capillary electrophoresis, high performance liquid chromatography (HPLC), thin layer chromatography (TLC), hyperdiffusion chromatography, and the like. The isolated proteins can also be sequenced according to standard techniques to identify polymorphisms.

The antibodies of the invention can also be used to detect the Wnt2 protein, or cells expressing them, using any of a number of well recognized immunological binding assays (see, e.g., U.S. Pat. Nos. 4,366,241; 4,376,110; 4,517,288; and 4,837,168). For a review of the general immunoassays, see also *Methods in Cell Biology*, Vol. 37, Asai, ed. Academic Press, Inc. New York (1993); *Basic and Clinical Immunology* 7th Edition, Stites & Terr, eds. (1991).

Thus, the present invention provides methods of detecting cells that overexpress Wnt2, in particular cancer cells. Typically, Wnt2 expression is analyzed in a biological sample. In one method, a biopsy is performed on the subject and the collected tissue is tested in vitro. The tissue or cells from the tissue is then contacted, with an anti-Wnt2 antibody of the invention. An immune complex which results indicates the presence of a Wnt2 protein in the biopsied sample. To facilitate such detection, the antibody can be radiolabeled or coupled to an effector molecule which is a detectable label, such as a radiolabel.

In another method, the cell or cancer cell overexpressing Wnt2 is detected in vivo using, for example, typical imaging systems. Then, the localization of the label is determined by any of the known methods for detecting the label. A conventional method for visualizing diagnostic imaging can be used. For example, paramagnetic isotopes can be used for MRI. Internalization of the antibody may be important to extend the life within the organism beyond that provided by extracellular binding, which will be susceptible to clearance by the extracellular enzymatic environment coupled with circulatory clearance.

The methods described above can also be used in prognostic assays or to predict drug response, that is as a pharmacogenomic marker. In particular, the methods can be used to predict a response to therapeutic regimens described herein. For example, such methods can be used to predict a response to therapeutic methods using the anti-Wnt2 antibodies of the invention.

III. METHODS USING ANTI-WNT2 ANTIBODIES AND SIRNA

A. Inhibition of Cell Proliferation

Agents that inhibit Wnt2 signaling, such as the anti-Wnt2 antibodies and siRNAs of the invention may find use in a variety of ways. In a preferred embodiment of this invention a method of inhibiting proliferation of a cell that overexpresses a Wnt2 is provided. The Wnt2 that is overexpressed can be either a Wnt2 protein or a Wnt2 mRNA. This method comprises the step of contacting the cell with an amount of an agent that inhibits Wnt2 signaling effective to inhibit proliferation of the cell. "Proliferation" refers to the growth of a cell, the reproduction or multiplication of a cell or morbid cysts.

In a preferred embodiment of the present invention, this method is practiced in vitro. As further described herein, the methods of the present invention can also be practiced in vivo.

In a preferred embodiment of the present invention, the cell being contacted with the agent is a cancer cell. Agents of the present invention are useful for inhibiting proliferation of a cancer cell selected from the group consisting of breast, ovarian, colorectal, gastric, lung, kidney, bladder, prostate, uterine, thyroid, pancreatic, cervical, esophageal, mesothelioma, head and neck, hepatocellular, melanoma, brain, vulval, testicular, sarcoma, intestine, skin, leukemia, and lymphoma cancer cells. A preferred cancer cell is a breast cancer cell, a melanoma cell, a lung cancer cell, a mesothelioma cell, a thyroid cancer cell, a colon cancer cell or a liver cancer cell.

B. Inducing Apoptosis

Agents that inhibit Wnt2 signaling, such as the anti-Wnt2 antibodies and siRNAs of the invention may find use in a variety of ways. In another preferred embodiment of this invention a method of inducing apoptosis of a cell that overexpresses a Wnt2 is provided. This method comprises the step of contacting the cell with an amount of an agent that inhibits Wnt2 signaling effective to induce apoptosis of the cell. Agents for use in this method, such as anti-Wnt2 antibodies or siRNAs are disclosed herein.

C. Inhibiting Wnt2 Signaling

Agents of the present invention, such as the anti-Wnt2 antibodies and siRNAs of the invention may find use in a variety of ways. In another preferred embodiment of this invention a method of inhibiting Wnt2 signaling in a cell is provided. This method comprises the step of contacting a cell that overexpresses a Wnt2 with an amount of an agent effective to inhibit Wnt2 signaling. Agents for use in this method, such as anti-Wnt2 antibodies or siRNAs are disclosed herein.

D. Treating a Disease

Agents of the present invention, such as the anti-Wnt2 antibodies and siRNAs of the invention may find use in a variety of ways. In a preferred embodiment of this invention a method of treating a disease associated with Wnt2 signaling is provided. This method comprises the step of administering to a subject, preferably to a subject in need of such treatment, an amount of an agent that inhibits Wnt2 signaling effective to treat the disease. Preferably, the subject is a human. Agents for use in this method, such as anti-Wnt2 antibodies or siRNAs are disclosed herein.

In a preferred embodiment the disease is a cancer. Agents of the present invention are useful for treating a cancer selected from the group consisting of breast, ovarian, colorectal, gastric, lung, kidney, bladder, prostate, uterine, thyroid, pancreatic, cervical, esophageal, mesothelioma, head and neck, hepatocellular, melanoma, brain, vulval, testicular, sarcoma, intestine, skin, leukemia, and lymphoma cancer. A preferred cancer is breast cancer, melanoma, lung cancer, mesothelioma, thyroid cancer, colon cancer or liver cancer.

As used herein, the terms "treat", "treating", and "treatment" include: (1) preventing a disease, such as cancer, i.e. causing the clinical symptoms of the disease not to develop in a subject that may be predisposed to the disease but does not yet experience any symptoms of the disease; (2) inhibiting the disease, i.e. arresting or reducing the development of the disease or its clinical symptoms; or (3) relieving the disease, i.e. causing regression of the disease or its clinical symptoms. Preferably, the subject in need of such treatment is a mammal, more preferable a human.

This invention also provides a method of treating a cancer that overexpresses Wnt2. This method comprises the step of administering to a subject in need of such treatment an amount of an agent effective to treat the cancer. Agents for use in this method, such as anti-Wnt2 antibodies or siRNAs are disclosed herein.

E. Detecting Cancer Cells in a Subject

Agents of the present invention, such as the anti-Wnt2 antibodies and siRNAs of the invention may find use in a variety of ways. In a preferred embodiment of this invention a method of detecting a cancer cell in a subject is provided. This method comprises the steps of providing a biological sample from the subject, wherein the biological sample comprises a cell suspected of being a cancer cell and detecting the level of Wnt2 expression in the cell. Optionally, this method comprises comparing the level of Wnt2 expression in the cell with the level of Wnt2 expression in a cell from one or more healthy subjects or with a previously determined reference range for a level of Wnt2 expression. In one embodiment of the invention, detecting the level of Wnt2 expression is carried out by detecting the level of Wnt2 mRNA. In another embodiment of the invention, detecting the level of Wnt2 expression is carried out by detecting the level of Wnt2 protein. Agents for use in this method, such as anti-Wnt2 antibodies or siRNAs are disclosed herein.

Detection of the level of Wnt2 expression may be determined for a variety of reasons. Detecting the level of Wnt2 expression may be (i) part of screening, diagnosis or prognosis of cancer in the subject; (ii) part of determining susceptibility of the subject to cancer; (iii) part of determining the stage or severity of a cancer in the subject; (iv) part of identifying a risk for the subject of developing a cancer; or (v) part of monitoring the effect of an anti-cancer drug or therapy administered to the subject diagnosed with cancer. The anti-cancer drug or therapy administered to the subject may comprise an anti-Wnt2 antibody or a siRNA of this invention.

In a preferred embodiment of this invention a method for identifying in a subject the stage or severity of a cancer, is provided. As shown herein, Wnt2 expression is overexpressed in various cancer cells (e.g., Tables 3-5). As further shown herein, anti Wnt2 antibodies and siRNA induce in a dose-dependent manner apoptosis in those cells. Thus, amounts of Wnt2 are characteristic of various cancer risk states, e.g., high, medium or low. The stage or severity of a cancer may be determined by measuring Wnt2 and then either submitting them to a classification algorithm or comparing them with a reference amount and/or pattern of Wnt2 that is associated with a particular stage or severity of the cancer.

Using the methods of the invention, Wnt2 levels are determined in a biological sample from a subject for whom a risk of developing cancer is to be determined. A Wnt2 level detected in a biological sample from the subject for whom a risk of developing cancer is to be determined that is higher than the Wnt2 level detected in a comparable biological sample from normal or healthy subjects or lower than a predetermined base level, indicates that the subject for whom a risk of developing cancer is to be determined has a risk of developing cancer.

In another preferred embodiment of the present invention, a cancer in a subject is determined as part of screening, diagnosis or prognosis of the cancer in the subject. Using the methods of the invention, Wnt2 levels are determined in a biological sample from a subject to be screened for cancer. A Wnt2 level detected in a biological sample from the subject to be screened for cancer that is higher than the Wnt2 level detected in a comparable biological sample from normal or healthy subjects or higher than a predetermined base level, indicates that the subject screened for cancer has or is likely to have cancer.

As described above, Wnt2 compositions are useful for treatment of cancer wherein Wnt2 expression is overexpressed. However, other drugs, for example, a composition comprising an inhibitor of Wnt2, as described herein, will also be useful for treating a cancer in a patient wherein Wnt2 expression is overexpressed. Thus, in a preferred embodiment of the present invention, a cancer status is determined as part of monitoring the effect of surgery (e.g., removal of tumor), the effect of an anti-cancer drug or a therapy administered to a subject diagnosed with a cancer wherein Wnt2 expression is overexpressed. The effect of surgery or an anti-cancer drug or a therapy administered to a subject with cancer may include reoccurrence of cancer, progression of cancer (worsening) and cancer regression (improvement).

Using the compositions, methods and kits of the present invention, Wnt2 levels are determined in a biological sample from a subject at various times after surgery or at various times of having been given an anti-cancer drug or a therapy. A Wnt2 level detected in a biological sample from a subject at a first time (t1; e.g., before giving an anti-cancer drug or a therapy) that is higher than the Wnt2 level detected in a comparable biological sample from the same subject taken at a second time (t2; e.g., after giving the anti-cancer drug or the therapy), indicates that the cancer in the subject is regressing. Likewise, a higher Wnt2 level at a second time compared to a Wnt2 level at a first time, indicates that the cancer in the subject is progressing. Similarly, a Wnt2 level detected in a biological sample from a subject at a first time (t1; e.g., shortly after surgery) that is higher than the Wnt2 level detected in a comparable biological sample from the same subject taken at a second time (t2; e.g., weeks or months after surgery), may indicate that the cancer in the subject is not reoccurring. Likewise, a higher Wnt2 level at the second time compared to the Wnt2 level at the first time, may indicate that the cancer in the subject is reoccurring.

F. siRNA for Use in the Methods of the Invention

Agents of the present invention that are useful for practicing the methods of the present invention include, but are not limited to anti-Wnt2 antibodies and siRNAs of Wnt2. Typically, such agents are capable of (i) binding to Wnt2 mRNA or Wnt2 protein, (ii) interfere with Wnt2 signaling and/or (iii) inhibit binding of Wnt2 protein to other proteins, such as a Frizzled receptor. In a preferred embodiment, the agent inhibiting cell proliferation is a siRNA of Wnt2. The present invention provides compositions and methods using RNA interference to modulate Wnt2 expression. These methods and compositions are useful for the treatment of disease, in particular cancer, induction of apoptosis and interfering with Wnt2 signaling.

In many species, introduction of double-stranded RNA (dsRNA) which may alternatively be referred to herein as small interfering RNA (siRNA), induces potent and specific gene silencing, a phenomena called RNA interference or RNAi. This phenomenon has been extensively documented in the nematode *C. elegans* (Fire et al., Nature, 391, 806-811, 1998), but is widespread in other organisms, ranging from trypanosomes to mouse. Depending on the organism being discussed, RNA interference has been referred to as "cosuppression", "post-transcriptional gene silencing", "sense suppression" and "quelling." RNAi is an attractive biotechnological tool because it provides a means for knocking out the activity of specific genes. It is particularly useful for knocking out gene expression in species that were not previously considered to be amenable to genetic analysis or manipulation.

RNAi is usually described as a post-transcriptional gene-silencing (PTGS) phenomenon in which dsRNAs trigger degradation of homologous mRNA in the cytoplasm. The basic process involves a dsRNA that is processed into shorter units (called short interfering RNAs (siRNAs)) that guide recognition and targeted cleavage of homologous messenger RNA (mRNA). The dsRNAs that (after processing) trigger RNAi/PTGS can be made in the nucleus or cytoplasm in a number of ways. The processing of dsRNA into siRNAs, which in turn degrade mRNA, is a two-step RNA degradation process. The first step involves a dsRNA endonuclease (ribonuclease III-like; RNase III-like) activity that processes dsRNA into sense and antisense RNAs which are 21 to 25 nucleotides (nt) long (i.e., siRNA). In *Drosophila*, this RNase III-type protein is termed Dicer. In the second step, the antisense siRNAs produced combine with, and serve as guides for, a different ribonuclease complex called RNA-induced silencing complex (RISC), which cleaves the homologous single-stranded mRNAs. RISC cuts the mRNA approximately in the middle of the region paired with the antisense siRNA, after which the mRNA is further degraded. dsRNAs from different sources can enter the processing pathway leading to RNAi/PTGS.

Thus, in a preferred embodiment of the present invention, the agent for use in the methods of the present invention is a siRNA of Wnt2. siRNA can be used to reduce the expression level of Wnt2. A siRNA of Wnt2 hybridizes to a Wnt2 mRNA and thereby decreases or inhibits production of Wnt2 protein.

In designing RNAi experiments there are several factors that need to be considered such as the nature of the siRNA, the durability of the silencing effect, and the choice of delivery system. To produce an RNAi effect, the siRNA that is introduced into the organism should contain exonic sequences. Furthermore, the RNAi process is homology dependent, so the sequences must be carefully selected so as to maximize gene specificity, while minimizing the possibility of cross-interference between homologous, but not gene-specific sequences. Preferably the siRNA exhibits greater than 90% or even 100% identity between the sequence of the siRNA and the gene to be inhibited. Sequences less than about 80% identical to the target gene are substantially less effective. Thus, the greater homology between the siRNA of Wnt2 and the Wnt2 gene whose expression is to be inhibited, the less likely expression of unrelated genes will be affected.

In addition, the size of the siRNA is important. Generally, the present invention relates to siRNA molecules of Wnt2, which are double or single stranded and comprise at least about 19-25 nucleotides, and are able to modulate the gene expression of Wnt2. In the context of the present invention, the siRNA is preferably less than 500, 200, 100, 50 or 25 nucleotides in length. More preferably, the siRNA is from about 19 nucleotides to about 25 nucleotides in length.

In one aspect, the invention generally features an isolated siRNA molecule of at least 19 nucleotides, having at least one strand that is substantially complementary to at least ten but no more than thirty consecutive nucleotides of Wnt2, and that reduces the expression of Wnt2 gene or protein. In a preferred embodiment of the present invention, the siRNA molecule has at least one strand that is substantially complementary to at least ten but no more than thirty consecutive nucleotides of human Wnt2 (GenBank No. NM_0003391, SEQ ID NO:152). More desirable, the isolated siRNA molecule has at least one strand that is substantially complementary to 19 to 25 nucleotides comprising nucleotides 714 to 732 of human Wnt2 (GenBank No. NM_0003391, SEQ ID NO:152). In a preferred embodiment of the present invention, the siRNA nucleic acid sequence is 5'-GAAGATGGGAAGCGC-CAAG-3' (SEQ ID NO:150).

In another preferred embodiment, the siRNA molecule of Wnt2 includes a sequence that is at least 90% homologous, preferably 95%, 99%, or 100% homologous, to the nucleic acid sequence shown in SEQ ID NO:152. Without undue experimentation and using the disclosure of this invention, it is understood that additional siRNAs of Wnt2 that modulate Wnt2 expression can be designed and used to practice the methods of the invention.

The siRNA may also comprise an alteration of one or more nucleotides. Such alterations can include the addition of non-nucleotide material, such as to the end(s) of the 19 to 25 nucleotide RNA or internally (at one or more nucleotides of the RNA). In a preferred embodiment, the RNA molecule contains a 3'-hydroxyl group. Nucleotides in the RNA molecules of the present invention can also comprise non-standard nucleotides, including non-naturally occurring nucleotides or deoxyribonucleotides. The double-stranded oligonucleotide may contain a modified backbone, for example, phosphorothioate, phosphorodithioate, or other modified backbones known in the art, or may contain non-natural internucleoside linkages. Additional modifications of siRNAs (e.g., 2'-O-methyl ribonucleotides, 2'-deoxy-2'-fluoro ribonucleotides, "universal base" nucleotides, 5-C-methyl nucleotides, one or more phosphorothioate internucleotide linkages, and inverted deoxyabasic residue incorporation) can be found in the published U.S. application publication number 20040019001 and U.S. Pat. No. 6,673,611 (incorporated by reference). Collectively, all such altered RNAs described above are referred to as modified siRNAs.

Preferably, RNAi is capable of decreasing the expression of Wnt2 in a cell by at least 10%, 20%, 30%, or 40%, more preferably by at least 50%, 60%, or 70%, and most preferably by at least 75%, 80%, 90%, 95% or more.

Introduction of siRNA into cells can be achieved by methods known in the art, including for example, microinjection, electroporation, or transfection of a vector comprising a nucleic acid from which the siRNA can be transcribed. Alternatively, a siRNA for Wnt2 can be directly introduced into a cell in a form that is capable of binding to Wnt2 mRNA transcripts. To increase durability and membrane-permeability the siRNA may be combined or modified with liposomes, poly-L-lysine, lipids, cholesterol, lipofectine or derivatives thereof. Preferred are cholesterol-conjugated siRNA for Wnt2 (see, Song et al., *Nature Med.* 9:347-351 (2003)).

G. Anti-Wnt2 Antibodies for Use in the Methods of the Invention

In another preferred embodiment of the present invention, the agent used in the methods of the present invention is an anti-Wnt2 antibody as fully described herein. The anti Wnt2 antibody can be a polyclonal or an anti-Wnt2 monoclonal antibody. Preferably, the methods of the present invention use an anti-Wnt2 monoclonal antibody.

IV. IDENTIFICATION OF INHIBITORS OF WNT SIGNALING

Wnt2 protein (or cells expressing them) or members of the Wnt signaling pathway, e.g., dvl, can also be used in drug screening assays to identify agents that inhibit Wnt signaling. The present invention thus provides novel methods for screening for compositions which inhibit cancer.

Assays for Wnt2 signaling can be designed to detect and/or quantify any part of the Wnt2 signaling pathway. For example the ability of an agent to affect intracellular β-catenin levels or to induce apoptosis in target cells can be measured. Assays suitable for these purposes are described herein.

Assays may include those designed to test binding activity of an inhibitor to either the Wnt2 ligand, the Frizzled receptor, or another member of the Wnt2 signaling cascade, e.g., dvl. These assays are particularly useful in identifying agents that modulate Wnt2 activity. Virtually any agent can be tested in such an assay. Such agents include, but are not limited to natural or synthetic polypeptides, antibodies, natural or synthetic small organic molecules, nucleic acids and the like.

As noted above, a family of secreted Frizzled-related proteins (sFRPs) function as soluble endogenous modulators of Wnt signaling by competing with Frizzled receptors for the binding of secreted Wnt ligands. Thus, in some format, test agents are based on natural ligands (e.g., Wnt ligands or sFRPs) of the Frizzled receptor.

Any of the assays for detecting Wnt2 signaling are amenable to high throughput screening. High throughput assays, binding assays and reporter gene assays are similarly well known. Thus, for example, U.S. Pat. No. 5,559,410 discloses high throughput screening methods for proteins, U.S. Pat. No. 5,585,639 discloses high throughput screening methods for nucleic acid binding (i.e., in arrays), while U.S. Pat. Nos. 5,576,220 and 5,541,061 disclose high throughput methods of screening for ligand/antibody binding.

In addition, high throughput screening systems are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate entire procedures including all sample and reagent pipetting, liquid dispensing, timed incubations, and final readings of the microplate in detector(s) appropriate for the assay. These configurable systems provide high throughput and rapid start up as well as a high degree of flexibility and customization. The manufacturers of such systems provide detailed protocols for various high throughput systems. Thus, for example, Zymark Corp. provides technical bulletins describing screening systems for detecting the modulation of gene transcription, ligand binding, and the like.

Other assays useful in the present invention are those designed to test neoplastic phenotypes of cancer cells. These assays include cell growth on soft agar; anchorage dependence; contact inhibition and density limitation of growth; cellular proliferation; cell death (apoptosis); cellular transformation; growth factor or serum dependence; tumor specific marker levels; invasiveness into Matrigel; tumor growth and metastasis in vivo; mRNA and protein expression in cells undergoing metastasis, and other characteristics of cancer cells.

The ability of test agents to inhibit cell growth can also be assessed by introducing the test into an animal model of disease, and assessing the growth of cancer cells in vivo. For example, human tumor cells can be introduced into an immunocompromised animal such as a "nude mouse". The test agent (e.g., a small molecule or an antibody) is administered to the animal and the ability of the tumor cell to form tumors—as assessed by the number and/or size of tumors formed in the animal—is compared to tumor growth in a control animal without the agent.

A. Inhibitors of Gene Expression

In one aspect of the present invention, inhibitors of the Wnt2 signaling pathway, e.g., Dvl inhibitors, can comprise nucleic acid molecules that inhibit expression of the target protein in the pathway. Conventional viral and non-viral based gene transfer methods can be used to introduce nucleic acids encoding engineered polypeptides, e.g., dominant negative forms of the protein, in mammalian cells or target tissues, or alternatively, nucleic acids e.g., inhibitors of target protein expression, such as siRNAs or anti-sense RNAs. Non-viral vector delivery systems include DNA plasmids, naked nucleic acid, and nucleic acid complexed with a delivery vehicle such as a liposome. Viral vector delivery systems include DNA and RNA viruses, which have either episomal or integrated genomes after delivery to the cell. For a review of gene therapy procedures, see Anderson, *Science* 256:808-813 (1992); Nabel & Felgner, *TIBTECH* 11:211-217 (1993); Mitani & Caskey, *TIBTECH* 11:162-166 (1993); Dillon, *TIBTECH* 11:167-175 (1993); Miller, *Nature* 357:455-460 (1992); Van Brunt, *Biotechnology* 6 (10):1149-1154 (1988); Vigne, *Restorative Neurology and Neuroscience* 8:35-36 (1995); Kremer & Perricaudet, *British Medical Bulletin* 51 (1):31-44 (1995); Haddada et al., in *Current Topics in Microbiology and Immunology* Doerfler and Böhm (eds) (1995); and Yu et al., *Gene Therapy* 1:13-26 (1994).

In some embodiments, small interfering RNAs are administered. In mammalian cells, introduction of long dsRNA (>30 nt) often initiates a potent antiviral response, exemplified by nonspecific inhibition of protein synthesis and RNA degradation. The phenomenon of RNA interference is described and discussed, e.g., in Bass, *Nature* 411:428-29 (2001); Elbahir et al., *Nature* 411:494-98 (2001); and Fire et al., *Nature* 391:806-11 (1998), where methods of making interfering RNA also are discussed. The siRNA inhibitors are less than 100 base pairs, typically 30 bps or shorter, and are made by approaches known in the art. Exemplary siRNAs according to the invention can have up to 29 nucleotides, 25 nucleotides, 22 nucleotides, 21 nucleotides, 20 nucleotides, 15 nucleotides, 10 nucleotides, 5 nucleotides or any integer thereabout or therebetween.

V. PHARMACEUTICAL COMPOSITIONS

As noted above, inhibitors of Wnt2 expression and agents of the present invention can be used to treat a disease associated with Wnt2 signaling, such as a cancer associated with Wnt2 signaling. The compositions for administration will commonly comprise an agent as fully described herein dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the patient's needs.

Thus, a typical pharmaceutical composition for intravenous administration would be about 0.1 to 10 mg per patient per day. Dosages from 0.1 up to about 100 mg per patient per day may be used, particularly when the drug is administered to a secluded site and not into the blood stream, such as into a body cavity or into a lumen of an organ. Substantially higher dosages are possible in topical administration. Actual methods for preparing parenterally administrable compositions will be known or apparent to those skilled in the art and are described in more detail in such publications as *Remington's Pharmaceutical Science*, 15th ed., Mack Publishing Company, Easton, Pa. (1980).

The pharmaceutical compositions can be administered in a variety of unit dosage forms depending upon the method of administration. For example, unit dosage forms suitable for oral administration include, but are not limited to, powder, tablets, pills, capsules and lozenges. It is recognized that antibodies when administered orally, should be protected from digestion. This is typically accomplished either by complexing the molecules with a composition to render them resistant to acidic and enzymatic hydrolysis, or by packaging the molecules in an appropriately resistant carrier, such as a liposome or a protection barrier. Means of protecting agents from digestion are well known in the art.

The compositions containing inhibitors and agents of the invention (e.g., antibodies) can be administered for therapeutic or prophylactic treatments. In therapeutic applications, compositions are administered to a patient suffering from a disease (e.g., breast cancer) in an amount sufficient to cure or at least partially arrest the disease and its complications. An amount adequate to accomplish this is defined as a "therapeutically effective dose." Amounts effective for this use will depend upon the severity of the disease and the general state of the patient's health. Single or multiple administrations of the compositions may be administered depending on the dosage and frequency as required and tolerated by the patient. In any event, the composition should provide a sufficient quantity of the agents of this invention to effectively treat the patient. An amount of an inhibitor that is capable of preventing or slowing the development of cancer in a patient is referred to as a "prophylactically effective dose." The particular dose required for a prophylactic treatment will depend upon the medical condition and history of the patient, the particular cancer being prevented, as well as other factors such as age, weight, gender, administration route, efficiency, etc. Such prophylactic treatments may be used, e.g., in a patient who has previously had cancer to prevent a recurrence of the cancer, or in a patient who is suspected of having a significant likelihood of developing cancer.

A "patient" or "subject" for the purposes of the present invention includes both humans and other animals, particularly mammals. Thus the methods are applicable to both human therapy and veterinary applications. In the preferred embodiment the patient is a mammal, preferably a primate, and in the most preferred embodiment the patient is human.

Other known cancer therapies can be used in combination with the methods of the invention. For example, inhibitors of Wnt signaling may also be used to target or sensitize a cell to other cancer therapeutic agents such as 5FU, vinblastine, actinomycin D, cisplatin, methotrexate, and the like. In other embodiments, the methods of the invention can be used with radiation therapy and the like.

In some instances an antibody belongs to a sub-type that activates serum complement when complexed with the transmembrane protein thereby mediating cytotoxicity or antigen-dependent cytotoxicity (ADCC). Thus, cancer can be treated by administering to a patient antibodies directed against Frizzled proteins on the surface of cancer cells. Antibody-labeling may activate a co-toxin, localize a toxin payload, or otherwise provide means to locally ablate cells. In these embodiments, the antibody is conjugated to an effector moiety. The effector moiety can be any number of molecules, including labeling moieties such as radioactive labels or fluorescent labels, or can be a therapeutic moiety, such as a cytotoxic agent.

A. Use of Wnt2 Polypeptides as Vaccines

In addition to administration of inhibitors of Wnt2 signaling, the Wnt2 proteins or immunogenic fragments of them can be administered as vaccine compositions to stimulate HTL, CTL, and antibody responses against the endogenous proteins. Such vaccine compositions can include, e.g., lipidated peptides (see, e.g., Vitiello et al. (1995) *J. Clin. Invest.* 95:341-349), peptide compositions encapsulated in poly(D, L-lactide-co-glycolide, "PLG") microspheres (see, e.g., Eldridge et al. (1991) *Molec. Immunol.* 28:287-294; Alonso et al. (1994) *Vaccine* 12:299-306; Jones et al. (1995) *Vaccine* 13:675-681), peptide compositions contained in immune stimulating complexes (ISCOMS; see, e.g., Takahashi, et al. (1990) *Nature* 344:873-875; Hu et al. (1998) *Clin. Exp. Immunol.* 113:235-243), multiple antigen peptide systems (MAPs; see, e.g., Tam (1988) *Proc. Nat'l Acad. Sci. USA* 85:5409-5413; Tam (1996) *J. Immunol. Methods* 196:17-32); viral delivery vectors (Perkus et al., p. 379, in Kaufmann (ed. 1996) *Concepts in Vaccine Development* de Gruyter; Chakrabarti, et al., (1986) Nature 320:535-537; Hu et al. (1986) *Nature* 320:537-540; Kieny et al., (1986) *AIDS Bio/Technology* 4:790-795; Top et al., (1971) *J. Infect. Dis.* 124:148-154; Chanda et al., (1990) *Virology* 175:535-547), particles of viral or synthetic origin (see, e.g., Kofler et al., (1996) *J. Immunol. Methods* 192:25-35; Eldridge et al., (1993) *Sem. Hematol.* 30:16-24; Falo et al., (1995) *Nature Med.* 7:649-653).

Vaccine compositions often include adjuvants. Many adjuvants contain a substance designed to protect the antigen from rapid catabolism, such as aluminum hydroxide or mineral oil, and a stimulator of immune responses, such as lipid A, *Bortadella pertussis*, or *Mycobacterium tuberculosis* derived proteins. Certain adjuvants are commercially available as, e.g., Freund's Incomplete Adjuvant and Complete Adjuvant (Difco Laboratories, Detroit, Mich.); Merck Adjuvant 65 (Merck and Company, Inc., Rahway, N.J.); AS-2 (SmithKline Beecham, Philadelphia, Pa.); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF, interleukin-2, -7, -12, and other like growth factors, may also be used as adjuvants.

Vaccines can be administered as nucleic acid compositions wherein DNA or RNA encoding the Wnt2 polypeptides, or a fragment thereof, is administered to a patient. See, e.g., Wolff et. al. (1990) *Science* 247:1465-1468; U.S. Pat. Nos. 5,580, 859; 5,589,466; 5,804,566; 5,739,118; 5,736,524; 5,679,647; and WO 98/04720. Examples of DNA-based delivery technologies include "naked DNA", facilitated (bupivicaine, polymers, peptide-mediated) delivery, cationic lipid complexes, and particle-mediated ("gene gun") or pressure-mediated delivery (see, e.g., U.S. Pat. No. 5,922,687).

Methods for the use of genes as DNA vaccines are well known, and include placing the desired gene or portion thereof under the control of a regulatable promoter or a tissue-specific promoter for expression in the patient. The gene used for DNA vaccines can encode full-length Wnt2 protein, or may encode portions of the proteins.

In a some embodiments, the DNA vaccines include a gene encoding an adjuvant molecule with the DNA vaccine. Such adjuvant molecules include cytokines that increase the immunogenic response to the polypeptide encoded by the DNA vaccine.

For therapeutic or prophylactic immunization purposes, the peptides of the invention can be expressed by viral or bacterial vectors. Examples of expression vectors include attenuated viral hosts, such as vaccinia or fowlpox. This approach involves the use of vaccinia virus, e.g., as a vector to express nucleotide sequences that encode Wnt2 polypeptides or polypeptide fragments. Upon introduction into a host, the recombinant vaccinia virus expresses the immunogenic peptide, and thereby elicits an immune response. Vaccinia vectors and methods useful in immunization protocols are described in, e.g., U.S. Pat. No. 4,722,848. Another vector is BCG (Bacille Calmette Guerin). BCG vectors are described in Stover et al., (1991) *Nature* 351:456-460. A wide variety of other vectors useful for therapeutic administration or immunization e.g., adeno and adeno-associated virus vectors, retroviral vectors, *Salmonella typhi* vectors, detoxified anthrax toxin vectors, and the like, will be apparent. See, e.g., Shata et al., (2000) *Mol. Med. Today* 6:66-71; Shedlock et al., (2000) *J. Leukoc. Biol.* 68:793-806; and Hipp et al., (2000) *In Vivo* 14:571-85.

VI. ADMINISTRATION OF INHIBITORS

The agents that inhibit Wnt2 signaling (e.g., anti Wnt2 antibodies and siRNA) can be used in a variety of therapeutic regimens. For example, the agents can be used in methods comprising, but not limited to parenteral (e.g., intravenous, intramuscular, intradermal, intraperitoneal, and subcutaneous routes), topical, oral, local, or transdermal administration. These methods can be used for prophylactic and/or therapeutic treatment.

A. Non-Viral Delivery Methods

Methods of non-viral delivery of nucleic acids encoding engineered polypeptides of the invention include lipofection, microinjection, biolistics, virosomes, liposomes, immunoliposomes, polycation or lipid:nucleic acid conjugates, naked DNA, artificial virions, and agent-enhanced uptake of DNA. Lipofection is described in e.g., U.S. Pat. No. 5,049,386, U.S. Pat. No. 4,946,787; and U.S. Pat. No. 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424, WO 91/16024. Delivery can be to cells (ex vivo administration) or target tissues (in vivo administration).

The preparation of lipid:nucleic acid complexes, including targeted liposomes such as immunolipid complexes, is well known to one of skill in the art (see, e.g., Crystal, *Science* 270:404-410 (1995); Blaese et al., *Cancer Gene Ther.* 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995); Ahmad et al., *Cancer Res.* 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

B. Viral Delivery Methods

The use of RNA or DNA viral based systems for the delivery of inhibitors of target Wnt pathway proteins, e.g., Dvl, are known in the art. Conventional viral based systems for the delivery of such nucleic acid inhibitors can include retroviral, lentivirus, adenoviral, adeno-associated and herpes simplex virus vectors for gene transfer.

In many gene therapy applications, it is desirable that the gene therapy vector be delivered with a high degree of specificity to a particular tissue type, e.g., a lung cancer. A viral vector is typically modified to have specificity for a given cell type by expressing a ligand as a fusion protein with a viral coat protein on the viruses outer surface. The ligand is chosen to have affinity for a receptor known to be present on the cell type of interest. For example, Han et al., *PNAS* 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other pairs of virus expressing a ligand fusion protein and target cell expressing a receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences thought to favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient.

Ex vivo cell transfection for diagnostics, research, or for gene therapy (e.g., via re-infusion of the transfected cells into the host organism) is well known to those of skill in the art. In some embodiments, cells are isolated from the subject organism, transfected with inhibitor nucleic acids and re-infused back into the subject organism (e.g., patient). Various cell types suitable for ex vivo transfection are well known to those of skill in the art (see, e.g., Freshney et al., *Culture of Animal Cells, A Manual of Basic Technique* (3rd ed. 1994)) and the references cited therein for a discussion of how to isolate and culture cells from patients).

Vectors (e.g., retroviruses, adenoviruses, liposomes, etc.) containing therapeutic nucleic acids can also be administered directly to the organism for transduction of cells in vivo. Alternatively, naked DNA can be administered. Administration is by any of the routes normally used for introducing a molecule into ultimate contact with blood or tissue cells. Suitable methods of administering such nucleic acids are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention, as described below (see, e.g., *Remington's Pharmaceutical Sciences*, 17th ed., 1989).

VII. KITS FOR USE IN DIAGNOSTIC, RESEARCH, AND THERAPEUTIC APPLICATIONS

The invention also provides kits that can be used for the detection of the Wnt2 nucleic acids or proteins disclosed here. Further, kits are provide comprising compositions described herein that allow the user to practice the methods of the invention. In diagnostic and research applications such kits may include any or all of the following: assay reagents, buffers, Wnt2-specific or Frizzled-specific nucleic acids or antibodies, hybridization probes and/or primers, and the like. A therapeutic product may include sterile saline or another pharmaceutically acceptable emulsion and suspension base.

In a preferred embodiment, the kit comprises an agent embracing the specifics as outlined herein, wherein the agent binds Wnt2 protein or Wnt2 nucleic acid, such as mRNA, interferes with Wnt2 signaling, or inhibits binding of Wnt2 protein to other proteins, such as a Frizzled receptor. The kit may further comprise one or more containers for agents and compositions of the present invention and instructions for using the agent to inhibit the proliferation of a cell overexpressing Wnt2, to treat a disease, such as a cancer overexpressing Wnt2, to induce apoptosis in a cell overexpressing Wnt2, to detect a cancer cell overexpressing Wnt2 or to practice any of the methods described herein.

In a preferred embodiment of the invention, a kit comprises a siRNA as shown in SEQ ID NO:150 or a siRNA comprising a nucleic acid of about 19-25 contiguous nucleotides of SEQ ID NO:152, wherein the siRNA binds to Wnt2 mRNA and inhibits translation of Wnt2 mRNA. This kit further comprises one or more containers for agents and compositions of the present invention and instructions for using the siRNA to inhibit the proliferation of a cell overexpressing Wnt2, to treat a disease, such as a cancer overexpressing Wnt2, to induce apoptosis in a cell overexpressing Wnt2, to detect a cancer cell overexpressing Wnt2 or to practice any of the methods described herein. Optionally, the kit comprises a control siRNA, for example a siRNA comprising a nucleic acid sequence as shown in SEQ ID NO:151.

As indicated above, the kits may include instructional materials containing directions (i.e., protocols) for the practice of the methods of this invention. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

The present invention also provides kits for screening for inhibitors of Wnt2 signaling. Such kits can be prepared from readily available materials and reagents. For example, such kits comprise one or more of the following materials: a Wnt2 polypeptide or polynucleotide, reaction tubes and instructions for testing the desired Wnt2 signaling function (e.g., β-catenin levels).

Pharmaceutical compositions and kits of the present invention embrace the specifics as outlined herein.

Although the forgoing invention has been described in some detail by way of illustration and example for clarity and understanding, it will be readily apparent to one ordinary skill in the art in light of the teachings of this invention that certain variations, changes, modifications and substitution of equivalents may be made thereto without necessarily departing from the spirit and scope of this invention. As a result, the embodiments described herein are subject to various modifications, changes and the like, with the scope of this invention being determined solely by reference to the claims appended hereto.

While each of the elements of the present invention is described herein as containing multiple embodiments, it should be understood that, unless indicated otherwise, each of the embodiments of a given element of the present invention is capable of being used with each of the embodiments of the other elements of the present invention and each such use is intended to form a distinct embodiment of the present invention.

The invention is further illustrated by the following examples, which are only illustrative and are not intended to limit the definition and scope of the invention in any way.

VIII. EXAMPLES

Example 1

Materials and Methods

1. Cell Lines and Tissue Samples

Human non-small-cell lung cancer (NSCLC) cell lines (A549, NCI-H1703, H460, and H1299), mesothelioma cancer cell lines (NCI-H2052, H28 and H513), melanoma cell lines (LOX, FEM, FEMX, and SK-Mel-2), breast cancer cell lines (MCF-7 and HuL100, and colon cancer cell lines (HCT116 and SW480) were from American Type Culture Collections (ATCC, Manassas, Va.). Mesothelioma cancer cell lines were obtained from the following sources: LRK1A and REN through a generous gift from Dr. Steven Albelda (University of Pennsylvania, Philadelphia, Pa.), NCI-H2052, H28 and H513 from American Type Culture Collections (ATCC, Manassas, Va.), MS-1 and NCI-H290 from NIH (Frederick, Md.) and LP9 were from the Cell Culture Core Facility at Harvard University (Boston, Mass.). All cell lines except LP9 were cultured in RPMI 1640 supplemented with 10% fetal bovine serum, penicillin (100 IU/ml) and streptomycin (100 µg/ml). LP9 was cultured in M199 containing 15% medium plus 10 ng/ml EGF and 0.4 µg/ml HC. Normal human small airway epithelial cells (SAEC) and bronchial epithelial cells (NHBE) were obtained from Clonetics (Walkersville, Md.) and cultured in Clonetics SAGM™ Bullet Kit. All cells were cultured at 37° C. in a humid incubator with 5% $CO_2$. Fresh lung cancer tissue and adjacent normal lung tissue and fresh mesothelioma tissue and adjacent normal pleural tissue from patients undergoing curative primary resection of their tumors were collected at the time of surgery, and immediately snap-frozen in liquid nitrogen (IRB # H8714-22942-01). These tissue samples were kept at −170° C. in a liquid nitrogen freezer before use.

2. Western Blotting

Standard protocol was used. Anti-Dvl3, and anti-Survivin antibodies were from Santa Cruz Biotechnology (Santa Cruz, Calif.). Anti-caspase3 antibody was from Oncogene (Cambridge, Mass.). Anti-β-Actin antibody was obtained from Cell Signaling Technology, Inc. (Beverly, Mass.). Anti-β-Catenin antibody was purchased from Transduction Laboratories (Lexington, Ky.). Anti-Cytochrome c antibody was from BD Biosciences (San Diego, Calif.). For detecting alteration of β-catenin and cytochrome c, cytosolic extracts were prepared and examined as described previously (Wang et al., *Mol Cell Biol* 19 (9):5923-9 (1999)).

3. TOPFLASH Assay of Tcf-Dependent Transcriptional Activity

TOPFLASH assays of Tcf-dependent transcriptional activity in various cell lines following incubation with anti-Wnt2 monoclonal antibody were performed as described in You et al. *Oncogene* (2004) 23:6170-4). Briefly, cells were plated in six-well plates. After incubation with control or anti Wnt2 monoclonal antibody (10 µg/ml) for 48 h, the TOPFLASH or FOPFLASH reporter plasmid was transfected transiently into cells as described previously (Uematsu et al., *Cancer Res*. (2003) 63:4547-51). Tcf-mediated gene transcription was determined by the ration of pTOPFLASH: pFOPFLASH luciferase activity. Each was normalized to luciferase activities of the pRL-TK reporter (cotransfected internalk control). Experiments were performed in triplicate.

4. Apoptosis Analysis

Cells were harvested by trypsinization and processed for determination of cell surface annexin-V and propodium iodide (PI) contents, according to the manufacture's protocol (Annexin V FITC Apoptosis Detection Kit (Oncogene, Cambridge, Mass.); Apotarget (BioSource International)). With the use of Annexin-V-PI double staining regime, three populations of cells are distinguishable in two color flow cytometry: (a) non-apoptotic cells: annexin-V and PI negative; (b) early apoptotic cells with exposed phosphatidylserine but intact cell membranes bound to Annexin V-FITC but excluded propidium iodide; and (c) cells in necrotic or late apoptotic stages were labeled with both Annexin V-FITC and propidium iodide. Then stained cells were immediately analyzed by flow cytometry (FACScan; Decton Dickinson, Franklin Lake, N.J.). TUNEL staining of tumor tissue samples harvested from in vivo experiment was performed using ApopTag Peroxidase In Situ Oligo Ligation Apoptosis Detection Kit (Chemicon International, Temecula, Calif.) according to the manufacturer's protocol.

5. In Vivo Tumor Suppression Study

Female nude mice, 5-6 weeks old, were injected s.c. with $1 \times 10^7$ LOX cells in the dorsal area in a volume of 100 µl. Three days later, the tumors were uniformly formed and the animals were then intraperitoneally (i.p.) injected with monoclonal anti-Wnt2 antibody, a control monoclonal antibody, or PBS buffer in a volume of 100 µl as well. Both the monoclonal anti-Wnt2 and the control antibodies were injected at the dose of 250 µg. Each injection was done twice weekly. Each group consisted of 8 mice. Tumor size was determined at weekly intervals, and tumor volumes were calculated using width (x) and length (y) ($x^2y/2$, where x<y) (Sonoda et al., *Cancer Res* 61 (13):4956-60 (2001)).

6. Proliferation Assay

Alimta® (MTA) was supplied by Eli Lilly (Indianapolis, Ind.). Alimta® was diluted in sterile physiological solution at a concentration of 10 mg/ml. The stock was divided into aliquots, stored at −80° C., and diluted in culture medium before each experiment. Wnt2 antibody was stored at 4° C. and used as previously described. Cell proliferation was determined by measuring metabolic activity of tetrazolium conversion (Cell Titer 96 assay, Promega, Madison, Wis.). Briefly, 5,000 cells were plated per well in a 96-well plate and culture medium containing increasing concentrations of both drugs was added. Plates were incubated at 37° C. for 72 hours in a CO2 incubator. Then a solubilization/stop solution was added and the absorbance was recorded with a fluorescence plate reader at a wavelength of 570 nm. Each experiment was repeated at least 3 times in triplicate.

7. DNA Sequence Analysis of Anti Wnt2 Monoclonal Antibodies

The CDR sequences of monoclonal antibodies produced by the hybridoma cell lines 17F7.G7, 17F7.E5, 8B11.D2 and 8B11.H6 were sequenced using standard DNA sequencing techniques. Briefly, PCR was used to amplify the V regions from first strand cDNA. The primer sets comprised a reverse primer in the constant region and an upstream primer hybridizing to the signal peptide region. Multiple upstream primers for both $V_H$ and $V_L$ were used. DNA sequences for the variable regions of anti-Wnt2 monoclonal antibodies are shown in FIGS. 14A-18C and, for example, in SEQ ID NOS: 68, 75, 92, 95, 111, 118, 129, 135, 141 and 144.

8. Protein Sequence Analysis of Anti-Wnt2 Antibodies

Anti-Wnt2 monoclonal antibodies were also sequenced directly by protein sequencing. Briefly, protein samples were reduced and Cys was alkylated with iodoacetamide yielding Cys(CAM). Next, the samples were electrophoresed by SDS-PAGE under reducing conditions and electroblotted onto PVDF membrane each yielding light and heavy chain upon staining with Amido Black. Standard protein sequencing techniques were employed. The N-terminal sequence of subclone MG7, for example is shown in SEQ ID NO:146.

9. Gene Expression Array

Figure 9:
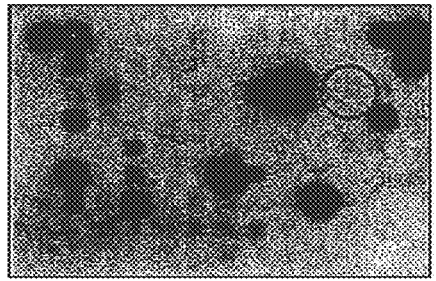
FIG. 9. Wnt-related gene expression profile in mesothelioma tissues. (A) RNA was extracted from 16 matched malignant mesothelioma and adjacent normal pleura. After extraction, RNA was subjected to a reverse transcriptase reaction and cDNA probes were labeled with Biotin-16-dUTP, and hybridized with the Wnt specific arrays. Detection was done using a chemiluminescent reaction and the membranes were exposed to X-ray film. Here are shown two matched samples as an example. Wnt2 is surrounded by a black circle. (B) Data were then matched against the gene list of the GEArray Q series human Wnt signaling pathway array provided by the manufacturer. Upregulated genes in the malignant tissue compared with the normal tissue are shown in gray (light grey for Wnt2). (C) Upregulated and downregulated genes in all studied samples (8 pairs) are detailed.

In some experiments gene expression profiling was analyzed using a custom array designed to profile the expression of genes involved in and downstream of Wnt signaling with the AmpoLabelling-LPR Kit protocol (GEArray Q Human Wnt Signaling Pathway Gene Array, SuperArray, Frederick, Md.). Briefly, total RNA isolated from the selected tissues was subjected to an RT reaction and cDNA probes were subsequently labeled with Biotin-16-dUTP (Roche), denatured and hybridized overnight in hybridization tubes containing the Wnt specific arrays. Detection was done with a chemiluminescent reaction by using a CDD camera. Images of spots were converted in numerical data using software provided by the manufacturer. Expression data was matched against the gene list provided by the manufacturer. A representative gene expression array analysis is shown in FIG. 9.

10. RNA Interference

Cells were plated into a 6-well plate with media without antibiotics 24 hrs before testing. The ion-exchange HPLC-purified siRNAs (Wnt2 siRNA and non-silencing siRNA control) were purchased from Qiagen-Xeragon (Germantown, Md.). The lyophilized siRNAs were dissolved in annealing buffer and reheated to 95° C. for 1 min followed by 1 hr at 37° C. incubation. We followed the protocol described by Elbashir (Elbashir et al., *Methods* 26 (2):199-213 (2002)). After siRNA transfection, plates were incubated for 3 days at 37° C. before further analysis. The siRNA specific for human Wnt2 was derived from the mRNA sequence 5'-GAAGATGGGAAGCGCCAAG-3' (SEQ ID NO:150) of human Wnt2. The control (nonsilencing) siRNA does not target any known mammalian gene 5'-AATTCTCCGAACGTGTCACGT-3' (SEQ ID NO:151).

11. Statistical Analysis

Data shown represent mean values (±S.E.M.). Unpaired T-Test in the Excel was used for comparing different treatments and cell lines. Other statistical comparisons were made with a two-sided Student's t-test (P<0.01).

Example 2

Identification of Antigenic Wnt2 Peptides

Antigenic peptides of human Wnt2 protein were determined using various methods. For example, the EMBOSS (Parker et al., *Biochemistry* 25:5425-5432 (1986)) finds antigenic sites in proteins. Antigenic peptides were also determined using the method of Kolaskar and Tangaonkar (K&T; FEBS Lett. (1990) 276 (1-2):172-4). Both methods led to the identification of similar antigenic peptides of human Wnt2 (Table 1). While most of the antigenic peptide sequences identified can be used to generate antibodies that specifically bind to human Wnt2, some antibodies may also bind to other Wnt proteins due to amino acid sequence homology among various Wnt proteins with human Wnt2. For example, the amino acid sequences of SEQ ID NO:42 and SEQ ID NO:44 have homology to human Wnt2B (Wnt13); the amino acid sequence of SEQ ID NO:43 has homology to human Wnt2B (Wnt13), Wnt3, Wnt3A, Wnt5B, and Wnt10A; the amino acid sequence of SEQ ID NO:45 has homology to human Wnt2B (Wnt13) and Wnt4; the amino acid sequence of SEQ ID NO:47 has homology to human Wnt1 and Wnt2B (Wnt13); and the amino acid sequence of SEQ ID NO:53 has homology to human Wnt-2B (Wnt13), Wnt3, and Wnt8B.

TABLE 1

Antigenic Peptides of Human Wnt2

| Sequence of Antigenic Peptide of Human Wnt2 and Position within SEQ ID NO:1 | SEQ ID NO | Method of Identification |
|---|---|---|
| 49 SSQRQLCHRHPDVMR 63 | 2 | |
| 4 PLGGIWLWLPLLLTWLTPE 22 | 3 | |
| 37 SRVMCDNVPGLV 48 | 4 | |
| 74 AECQHQFRQH 83 | 5 | |
| 92 RDHSLFGRVLLR 103 | 6 | |
| 107 ESAFVYAISSAGVVFAITRACSQGEVKSCSCD 138 | 7 | |
| 137 CDPKKMGSAKDSKG 150 | 8 | |
| 163 YGIKFARAFVD 173 | 9 | |
| 171 VDAKERKGKDAR 183 | 10 | |
| 202 LKQECKCHGVSGSCTLRTCWLAM 224 | 11 | |
| 240 GAIQVVM 246 | 12 | |
| 265 KNDLVYFENSPDYCIR 280 | 13 | |
| 289 TAGRVCNLTSRGMDSCEVMCCG 310 | 14 | |
| 344 DVHTCKAPKNADWTTAT 360 | 15 | |
| 38 RVMCDNVPGLVSSQRQLCHRHP 59 | 30 | EMBOSS |
| 75 ECQHQFR 81 | 31 | EMBOSS |

TABLE 1-continued

Antigenic Peptides of Human Wnt2

| Sequence of Antigenic Peptide of Human Wnt2 and Position within SEQ ID NO:1 | SEQ ID NO | Method of Identification |
|---|---|---|
| 93 DHSLFGRVLLRS 104 | 32 | EMBOSS |
| 108 SAFVYAISSAGVVFAITRACSQGEVKSCSCDP 139 | 33 | EMBOSS |
| 164 GIKFARAFVDA 174 | 34 | EMBOSS |
| 203 KQECKCHGVSGSCTLRTCWLAMA 225 | 35 | EMBOSS |
| 241 IQVVMN 247 | 36 | EMBOSS |
| 266 NDLVYFE 272 | 37 | EMBOSS |
| 275 PDYCIRD 281 | 38 | EMBOSS |
| 290 AGRVCNLT 297 | 39 | EMBOSS |
| 303 SCEVMCCGR 311 | 40 | EMBOSS |
| 323 KCGCKFHWCCAVRCQDCLEALDVHTCKAP 351 | 41 | EMBOSS |
| 37 SRVMCDNVPGLVSSQRQLCHRHP 58 | 42 | K & T |
| 74 AECQHQF 80 | 43 | K & T |
| 92 RDHSLFGRVLLR 103 | 44 | K & T |
| 107 ESAFVYAISSAGVVFAITRACSQGEVKSCSCD 138 | 45 | K & T |
| 163 YGIKFARAFVD 173 | 46 | K & T |
| 202 LKQECKCHGVSGSCTLRTCWLAM 224 | 47 | K & T |
| 240 GAIQVVM 246 | 48 | K & T |
| 265 KNDLVYF 271 | 49 | K & T |
| 274 SPDYCIR 280 | 50 | K & T |
| 289 TAGRVCNL 296 | 51 | K & T |
| 302 DSCEVMCCG 310 | 52 | K & T |
| 322 TKCGCKFHWCCAVRCQDCLEALDVHTCKA 350 | 53 | K & T |

Example 3

Generation of Anti-Wnt2 Monoclonal Antibodies and Antibody Incubation with Cells The antigen used to raise monoclonal anti-Wnt2 antibodies was a synthetic peptide corresponding to amino acid residues 49-63 of the human Wnt2 (Ac-SSQRQLCHRHPDVMR-amide, SEQ ID NO:2). This antigen was chosen bioinformatically based on its hydrophilicity (Parker et al., (1986) *Biochemistry* 25 (19):5425-32), antigenicity (Welling et al., (1985) *FEBS Lett.* 188 (2):215-8), accessibility (Janin, *Nature* 277:491-2 (1979)), sequence homology (BLAST search), and N-terminal vicinity.

Figure 14B:
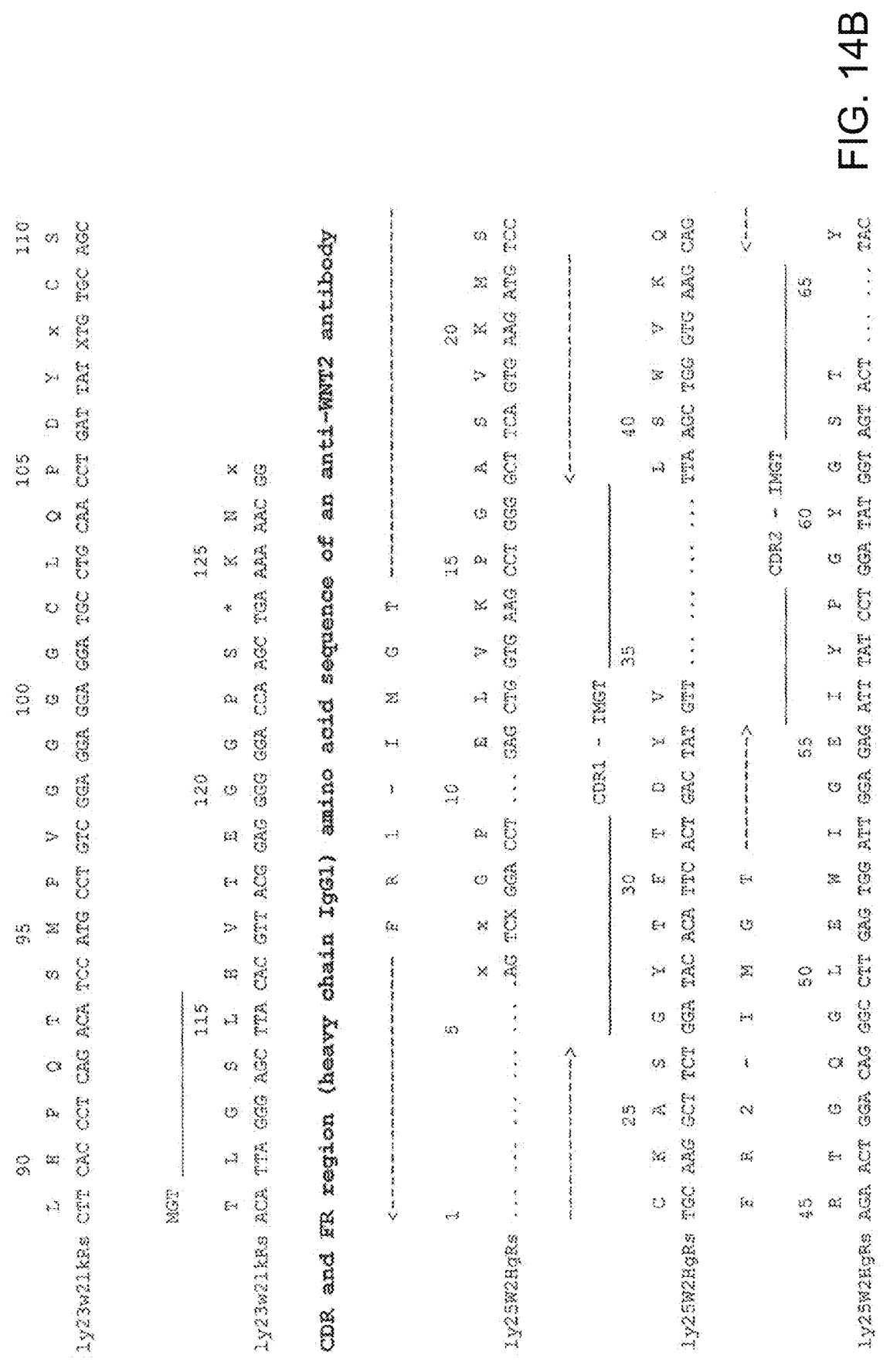
Figure 14C:
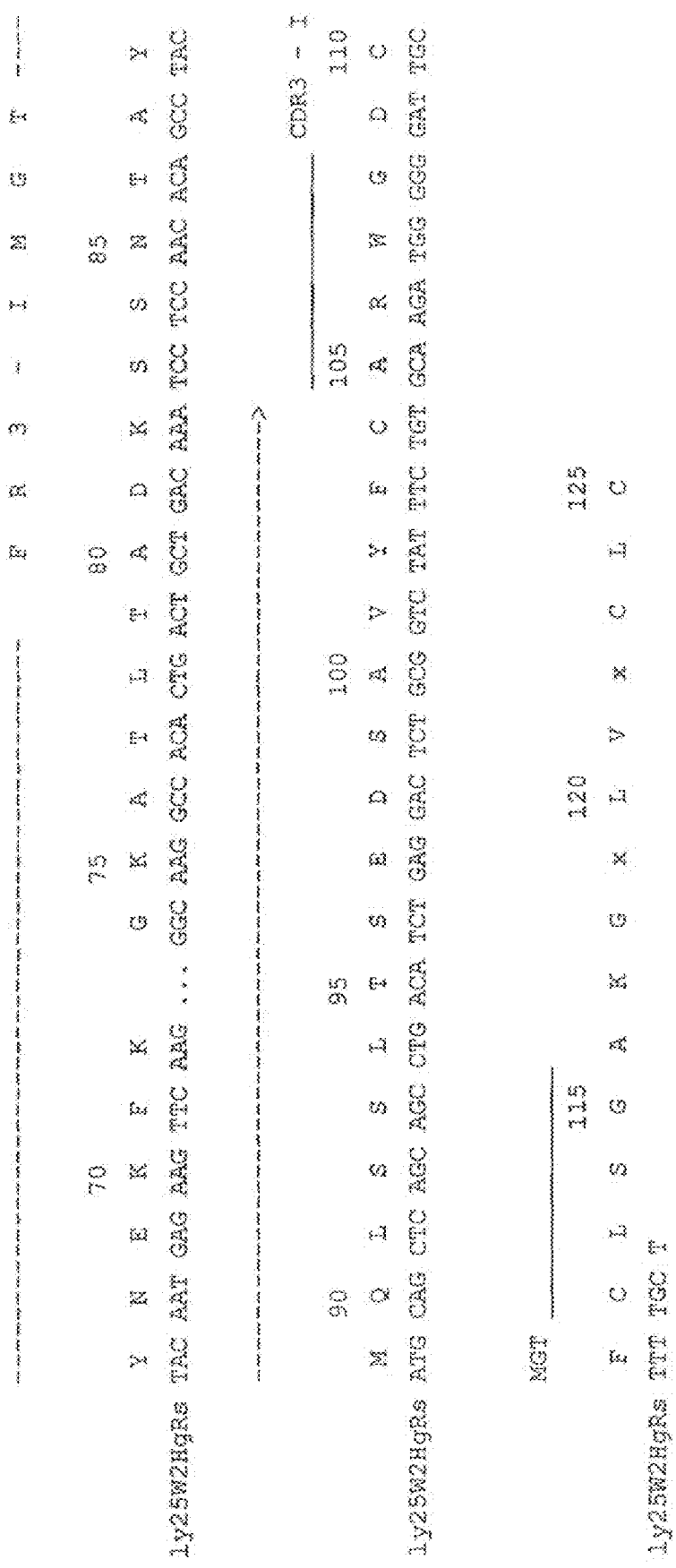

The anti-Wnt2 mouse monoclonal antibody (IgG$_1$) was custom-made at Rockland Inc. (Gilbertsville, Pa.). Several hybridoma cell lines were generated of which five were characterized in detail: (1) 17F7.G7 (Subclone A; FIGS. 14A-14C); (2) 17F7.G7 (Subclone B; FIGS. 18A-18C); (3) 17F7.E5 (FIGS. 16A-16B); (4) 8B11.D2 (FIGS. 15A-15B); and (5) 8B11.H6 (FIGS. 17A-17C). Two different light chains were found in 8B11.H6, termed 8B11.H6 (Chain1) and 8B11.H6 (Chain2). Also, two different light chains, Chain1 and Chain2, were found for 17F7.G7 (Subclone B). The $V_L$CDR and $V_H$CDR sequences of these anti-Wnt2 monoclonal antibodies are shown in Table 2. The location of CDR sequences, FR sequences and nucleic acid sequences encoding same are shown in FIGS. 14A-18C. The test bleed was screened twice by ELISA using the peptide, and the parental clones and the subclones were screened by western blot analysis.

TABLE 2

$V_L$CDR and $V_H$CDR Sequences of Anti-Wnt2 Monoclonal Antibodies

| Anti Wnt2 mAb | $V_L$CDR1 | $V_L$CDR2 | $V_L$CDR3 |
|---|---|---|---|
| 17F7.G7 (subclone A) | KSVSTSGYSY (SEQ ID NO: 56) | LVS (SEQ ID NO: 58) | PDYxCSTLGSL (SEQ ID NO: 60) |
| 17F7.G7 (subclone B) (Chain1) | KSVSTSGYSY (SEQ ID NO: 56) | LVS (SEQ ID NO: 58) | QHIRELTR (SEQ ID NO: 84) |
| 17F7.G7 (subclone B) (Chain2) | QSLLDSDGKTY (SEQ ID NO: 104) | LVS (SEQ ID NO: 58) | WQGTHFPWT (SEQ ID NO: 138) |
| 17F7.E5 | QSLLDSDGKTY (SEQ ID NO: 104) | LVS (SEQ ID NO: 58) | WQGTHFPWTLR (SEQ ID NO: 107) |
| 8B11.D2 | KSVSTSGYSY (SEQ ID NO: 56) | LVS (SEQ ID NO: 58) | QHIRELTR (SEQ ID NO: 84) |
| 8B11.H6 (CHAIN 1) | KSVSTSGYSY (SEQ ID NO: 56) | LVS (SEQ ID NO: 58) | QHIRELTR (SEQ ID NO: 84) |
| 8B11.H6 (CHAIN 2) | QRLLYSNGKTY (SEQ ID NO: 125) | LVS (SEQ ID NO: 58) | VQGTHFPWTLR (SEQ ID NO: 126) |

| Anti Wnt2 mAb | $V_H$CDR1 | $V_H$CDR2 | $V_H$CDR3 |
|---|---|---|---|
| 17F7.G7 (subclone A*) | GYTFTDYV (SEQ ID NO: 63) | IYPGYGST (SEQ ID NO: 65) | ARWGDCFCLSG (SEQ ID NO: 67) |
| 17F7.G7 (subclone B) | GYTFTDYV (SEQ ID NO: 63) | IYPGYGST (SEQ ID NO: 65) | ARWGDSFAY (SEQ ID NO: 110) |
| 17F7.E5 | GYTFTDYV (SEQ ID NO: 63) | IYPGYGST (SEQ ID NO: 65) | ARWGDSFAY (SEQ ID NO: 110) |
| 8B11.D2 | GYTFTTYV (SEQ ID NO: 87) | IDPYNDGT (SEQ ID NO: 89) | TRGNGNYESYYAMDY (SEQ ID NO: 91) |
| 8B11.H6 | GYTFTTYV (SEQ ID NO: 87) | IDPYNDGT (SEQ ID NO: 89) | TRGNGNYESYYAMDY (SEQ ID NO: 91) |

*, 17F7.G7 (subclone A, FIGS. 14A-14C) was resequenced and the CDR3 sequence ARWGDSFAY (SEQ ID NO:110) was obtained.

It is apparent from the analysis of the these antibodies that certain CDR sequences are preferred (see, Table 2). For example, each anti-Wnt2 monoclonal antibody analyzed herein comprises the amino acid sequence LVS (SEQ ID NO:58) for $V_L$CDR2. Other CDR sequences are also very similar, such as the V$_H$CDR1 sequences GYTFTDYV (SEQ ID NO:63) and GYTFTTYV (SEQ ID NO:87), differing by one amino acid residue.

Monoclonal antibodies were affinity purified by using Protein G and kept at −80° C. Seize X mammalian Immunoprecipitation Kit (Pierce Biotechnology, Rockford, Ill.) was used to precipitate Wnt2 protein from cell line extracts according to the manufacture's protocol and followed by Western blotting. Cells were plated in 6-well plates or 10 cm dishes one day before experiments. Then normal media was replaced by media containing antibodies at various concentrations and the cells were incubated at 37° C. in a humid incubator with 5% $CO_2$. At various time points the cells were collected using standard protocols for further analysis. Control antibody is mouse IgG$_1$MOPC21 from Sigma-Aldrich Co. (St Louis, Mo.). Anti Wnt2 monoclonal antibody 17F7.G7 was used in the experiments described.

Example 4

Wnt2 mRNA Expression in Normal and Cancer Tissues

Wnt2 mRNA expression in human normal and cancer tissues using cDNA arrays was studied. Briefly, multiple RNA microarrays (Clontech) from normal (76), as well as tumor-normal matched (19) human RNA panels were used for the detection of Wnt2 mRNA expression using a Wnt2 cDNA probe. A full-length Wnt2 cDNA probe was radiolabeled and hybridized to the RNA microarrays. In normal human organs, Wnt2 mRNA was expressed in placenta and weakly in fetal lung and normal lung (You et al. *Cancer Res.* 64:5385-89 (2004)). Minimal or no expression was noticed in all other normal human tissues in a human RNA master blot (You et al., *Cancer Res.* 64:5385-89 (2004)). In matched human non-cancerous and cancerous tissues, Wnt2 mRNA was frequently overexpressed in a variety of human cancer tissues, including 10 out 10 colon cancers, 10 out of 10 rectal cancers, 6 out of 7 intestinal cancers, 8 out of 10 stomach cancers, and 4 out of 10 thyroid cancers (Table 3). In addition, increased Wnt2 mRNA levels were observed in mesothelioma (FIG. 9), melanoma, sarcoma, cancer of the endometrium, leukemia, glioblastoma, esophagus cancer, nasopharyngeal cancer, head and neck cancer and lung cancer metastasis. A Wnt-related gene expression profile, for example, in mesothelioma cells is shown in FIG. 9.

TABLE 3

Wnt2 mRNA Overexpression in Human Cancers (mRNA Microarray analysis)

| Cancer Tissue | Wnt2 mRNA Overexpression in Tumor |
|---|---|
| 1. Breast | 4/10 |
| 2. Ovary | 4/10 |
| 3. Colon | 10/10 |
| 4. Stomach | 8/10 |
| 5. Lung | 2/10 |
| 6. Kidney | 1/10 |
| 7. Bladder | 3/5 |
| 8. Vulva | 3/5 |
| 9. Prostate | 2/4 |
| 10. Uterus | 5/10 |
| 11. Cervix | 5/10 |
| 12. Rectum | 10/10 |
| 13. Thyroid | 4/10 |
| 14. Testis | 4/10 |
| 15. Skin | 2/10 |
| 16. Intestine | 6/7 |
| 17. Pancreas | 6/7 |
| 18. Trachea | 2/3 |
| 19. Liver | 2/4 |

Example 5

Monoclonal Anti-Wnt2 Antibody Precipitates Human Wnt2 Proteins in Cell Extracts

A monoclonal antibody against a Wnt2 N-terminal peptide was generated (see Example 1). To test whether the monoclonal anti-Wnt2 antibody could bind specifically to the native form of Wnt2 protein in cultured cells, immunoprecipitation with this monoclonal antibody alone or after pre-incubation with blocking peptide (30-fold over the antibody) in cell extracts from three cell lines was performed. The C57Wnt2 cell line served as a positive control. NSCLC (A549) and melanoma (LOX) cell lines were also tested. In C57Wnt2, A549 and LOX cells, Wnt2 protein was precipitated by the monoclonal anti-Wnt2 antibody. When the monoclonal anti-Wnt2 antibody was pre-incubated with blocking peptide, its ability to precipitate Wnt2 protein was blocked in all three cell lines. Wnt2 protein was not precipitated by the monoclonal antibody after pre-incubating with the blocking peptide. These data indicate that the anti-Wnt2 monoclonal antibody can bind specifically to the native form of Wnt2 protein.

Example 6

Human Wnt2 Protein Expression in Normal and Cancer Tissues

Figure 10:
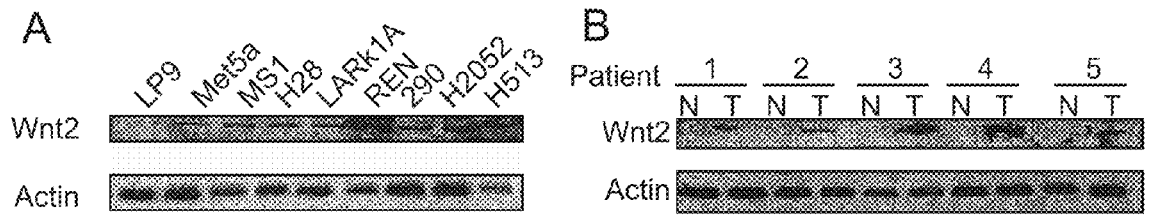
FIG. 10. Wnt2 expression in normal and mesothelioma cell lines and in tissues. (A) Western Blot analysis of Wnt2 expression in normal mesothelial cell line (LP9) and in several malignant mesothelioma cell lines. (B) Western Blot analysis of Wnt2 expression in tissues. Whole cell extracts were prepared from freshly resected tumor (T) and autologous matched normal pleura (N). Actin was used as a control.
Figure 11A:
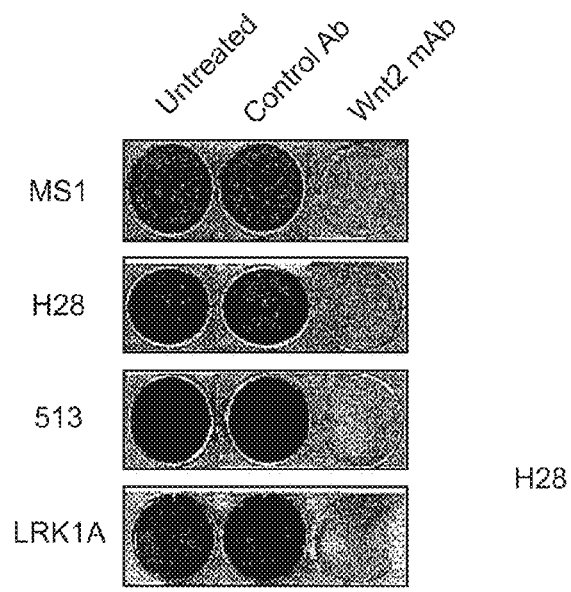
FIGS. 11A-11D. Anti-Wnt2 monoclonal antibody induces apoptosis in mesothelioma cancer cell lines. (A) Staining with 0.5% Crystal Violet of four malignant pleural mesothelioma cell lines either untreated or treated with a control antibody (control Ab) or a specific monoclonal anti-Wnt2 antibody at a concentration of 10 µg/ml (Wnt2 mAb).
Figure 11B:
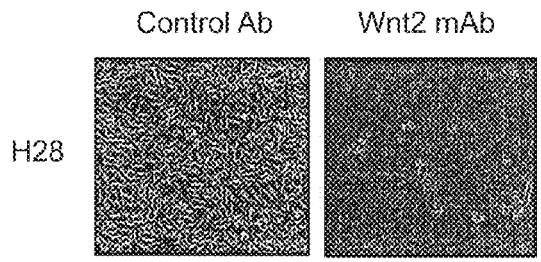
Figure 11C:
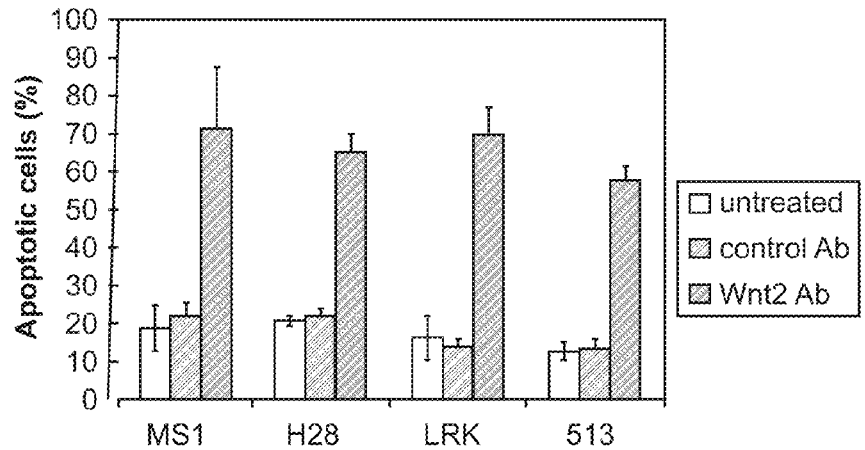
Figure 11D:
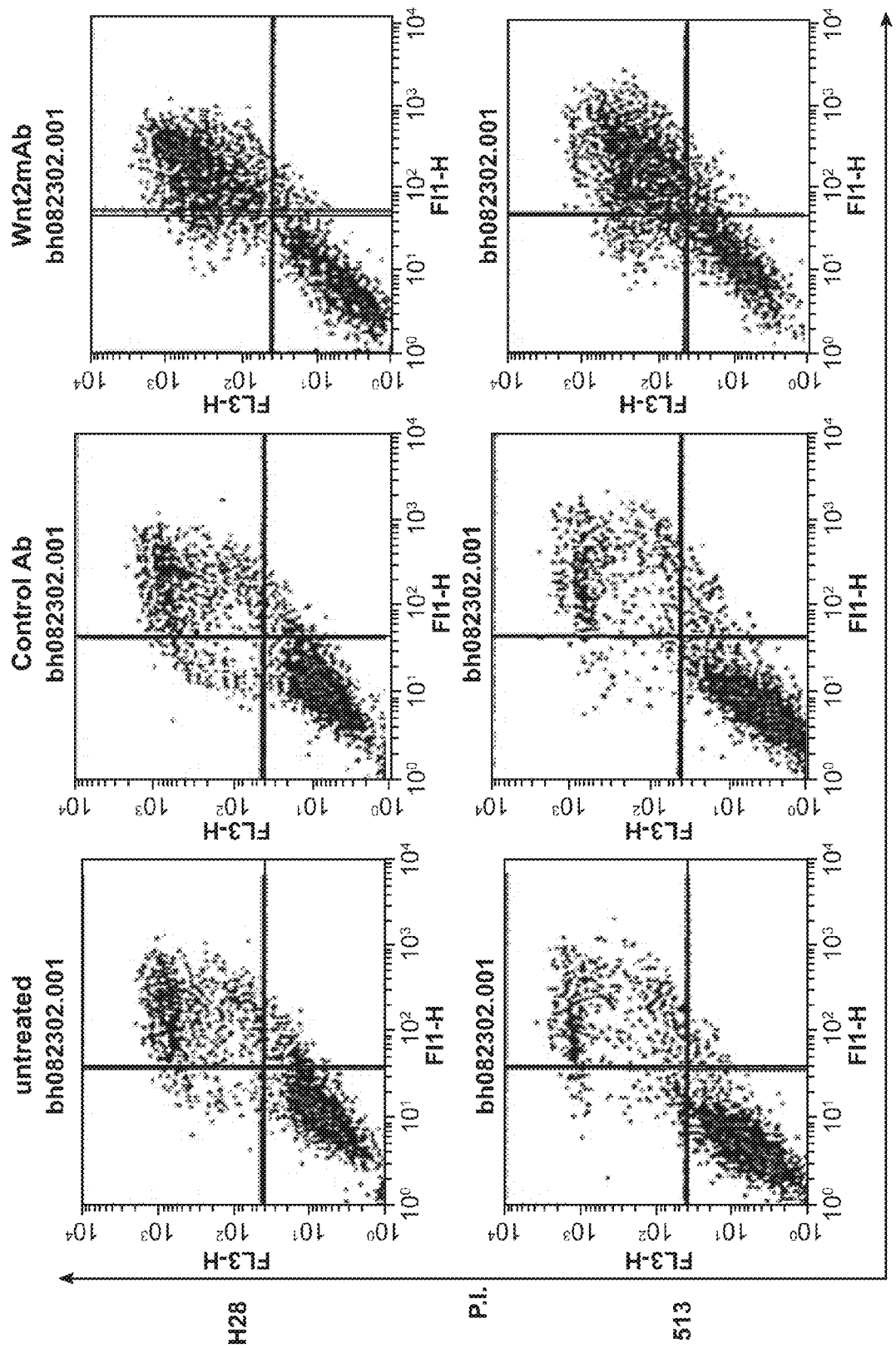

Wnt2 protein expression in numerous human cancer cell lines (Table 3) was tested using this monoclonal antibody; including four human NSCLC cell lines (A549, H1299, H1703, and H460), one normal mesothelial cell line (LP9; FIG. 10) and eight malignant mesothelioma cell lines (Met5a, LARk1A, REN, H290, H2052, MS-1, H513, and H28, FIG. 10), four human melanoma cell lines (LOX, FEM, FEMX, and SK-Mel-2), two breast cancer cell lines (HuL100 and MCF-7), as well as two colon cancer cell lines (HCT116 and SW480). Small airway epithelial cells (SAEC) and normal primary human bronchial epithelial cells (NHBE) were used as normal controls. Wnt2 protein expression was found in all of the cancer cell lines tested. Wnt2 expression was not observed in the two primary normal lung cells (SAEC and NHBE). In addition, 7 out of 8 freshly resected NSCLC tissues had increased expression of Wnt2 protein compared with autologous matched normal lung tissue controls (data not shown). Further, 5 out of 5 freshly resected pleura mesothelioma from patients showed Wnt2 protein expression, while Wnt2 protein was not detected in autologous matched normal pleura (FIG. 10).

Example 7

Anti-Wnt2 Monoclonal Antibody Mediates Cytotoxicity/Apoptosis in Primary Cell Cultures from Cancer Patients Fresh primary cultures made from cancer tissues obtained from patients were established. Most of the cancers analyzed, expressed a high level expression of Wnt2 protein. When these primary cultures freshly made from cancer patients (e.g, thyroid cancer, colon cancer or malignant melanoma) were incubated with anti-Wnt2 monoclonal antibody (about 10 µg/ml), cytotoxicity/apoptosis was observed ("++++;" Table 4).

TABLE 4

Anti-Wnt2 mAb Mediated Cytotoxicity/Apoptosis in Primary Cultures of Cancer Patients.

| Patient | Cancer Type | Cytotoxicity/Apoptosis |
| --- | --- | --- |
| #565 | Lung Cancer | +/− |
| #571 | Lung Cancer | ++ |
| #610 | Lung Cancer | ++++ |
| #595 | Colon Cancer | ++++ |
| #598 | Colon Cancer Metastasis | ++++ |
| #599 | Colon Cancer Metastasis | ++++ |
| #560 | Thyroid Cancer | +++ |
| #570 | Ovarian Cancer | ++++ |
| #547 | Malignant Melanoma | ++++ |
| #608 | Malignant Melanoma | ++++ |
| #714 | Malignant Melanoma | ++++ |
| #696 | Mesothelioma | ++++ |
| #569 | Osteogenic Sarcoma | ++++ |
| #588 | Sarcoma | ++++ |
| #602 | Sarcoma Metastasis | ++++ |
| #603 | Sarcoma | ++++ |

The following cytotoxicty/apoptosis is indicated: +/−, about 40%; ++, about 70%, and ++++, more than 90%.

Example 8

Anti-Wnt2 Antibody-Induced Apoptosis is Correlated with Wnt2 Expression

Figure 6:
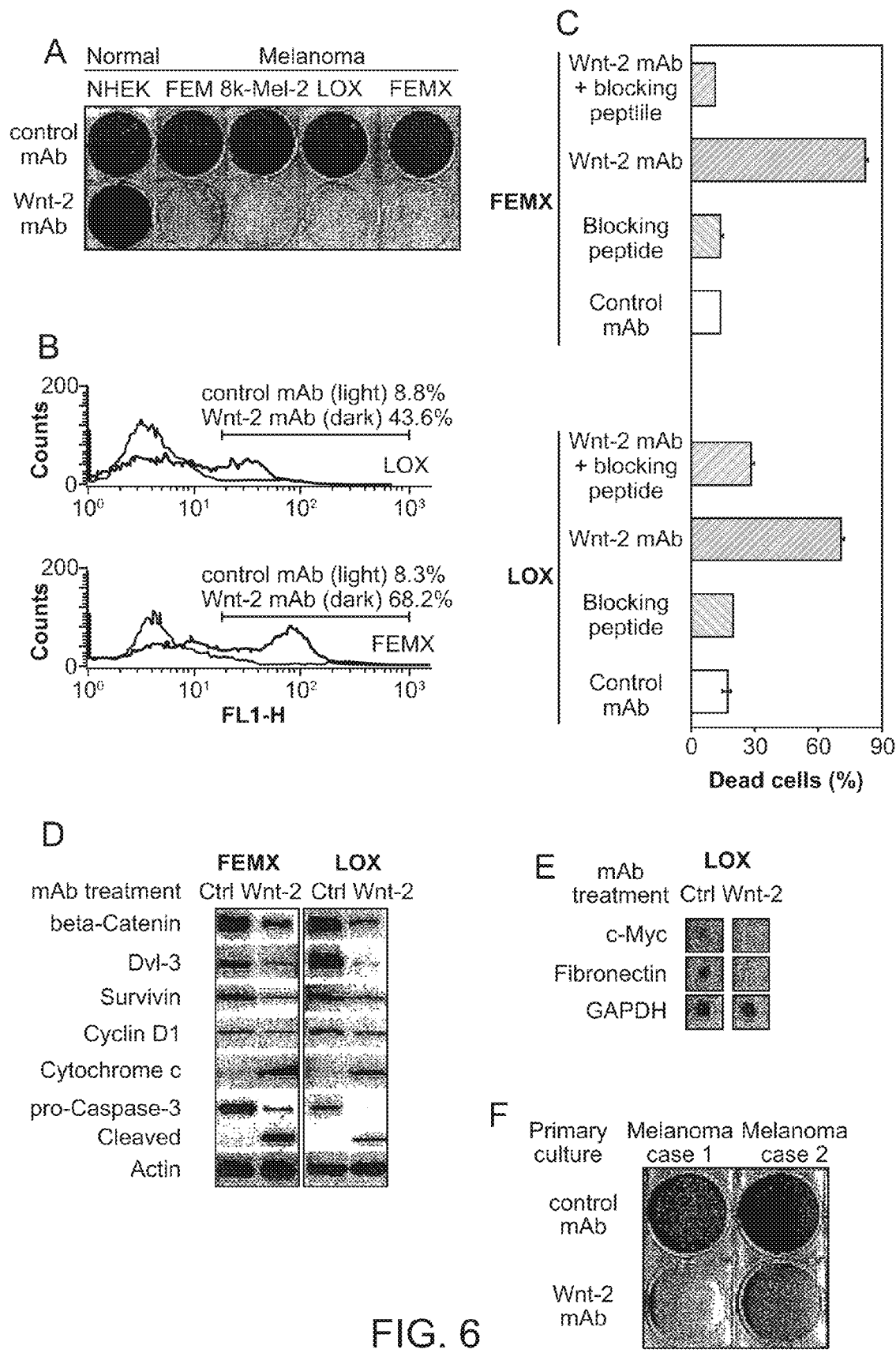
FIG. 6. The anti-Wnt2 monoclonal antibody induces apoptosis in melanoma cell lines and primary cultures. (a) This panel shows 0.5% Crystal Violet staining of normal human epithelial keratinocytes (NHEK) and four human melanoma cell lines (LOX, FEMX, FEM, and SK-Mel-2) after the anti-Wnt2 antibody treatment. (b) The panel shows these examples of apoptosis analysis by flow cytometry. FEMX and LOX cancer cells were treated with control antibody and anti Wnt2 monoclonal antibody, respectively. FL1-H represents annexin V-FITC staining. (c) Specific cell killing by anti Wnt2 monoclonal antibody in FEMX and LOX cancer cells. The panel shows percentage of dead FEMX and LOX cells after about 72 h treatment with monoclonal antibody alone and with monoclonal antibody blocked by preincubation with blocking peptide. Controls are blocking peptide alone and control mAb. After incubation, cells were collected for flow cytometry analysis. Results are the means±s.d. (error bars). (d) Western analysis before and after anti-Wnt2 antibody treatment. Two melanoma cell lines, FEMX and LOX, were treated with anti Wnt2 antibody. Expression of Dvl-3, β-catenin, surviving, cyclin D1, cytochrome c, pro-caspase-3, and cleaved caspase-3 was assessed. Actin served as a loading control. (e) c-Myc and fibronectin genes are down-regulated in the LOX melanoma cell line after anti-Wnt2 monoclonal antibody treatment. Total RNA was used for hybridization. (f) This panel shows 0.5% Crystal Violet staining of primary tumor cultures freshly made from patients with malignant melanoma after the anti-Wnt2 antibody treatment.

Anti-Wnt2 monoclonal antibody was used to treat a number of human cancer cell lines including four human NSCLC cell lines (A549, H1299, H1703, and H460), five malignant pleural mesothelioma cell lines (H290, H2052, MS-1, H513, and H28), four human melanoma cell lines (LOX, FEM, FEMX, and SK-Mel-2), two breast cancer cell lines (HuL100 and MCF-7), as well as two colon cancer cell lines (HCT116 and SW480). After 3-5 days of incubation significant cell death in all these cell lines (over 90% cell death at 10.0 µg/ml of the antibody, P<0.005) was observed (Table 5). No noticeable cytopathic effect in these cell lines was observed when the monoclonal antibody was pre-incubated with a blocking peptide or after control monoclonal antibody treatment. Also no effect was noticed in the NHBE cells treated with the same monoclonal anti-Wnt2 antibody. Cell killing was due largely to induction of apoptosis (43.6-79.2% of apoptotic cells after 72 hrs of incubation). Induction of apoptosis by this monoclonal antibody was dose and time dependent (data not shown). A representative example of this analysis using NSCLC cell lines is shown in FIG. 1. Induction of apoptosis in melanoma cells is shown in FIG. 6 and induction of apoptosis in mesothelioma cancer cell lines is shown in FIGS. 11A-11D. In addition, cytotoxic effects of anti-Wnt2 monoclonal antibody in hepatoma cell lines HepG2 and Hep3B were observed (data not shown).

As a specificity control, induction of apoptosis was examined by using monoclonal Wnt2 antibody blocked by overnight pre-incubation with blocking peptide (30-fold over the antibody) in A549, LOX and FEMX. After 72 hrs of incubation, the anti-Wnt2 antibody induced apoptosis could be inhibited significantly by blocking peptide (P<0.003). Same dose of blocking peptide (300 µg/ml for 72 hrs) alone had no effect on cell viability. After about 72 hrs of treatment with either the monoclonal antibody alone (10 µg/ml) or with the monoclonal antibody blocked by pre-incubation with blocking peptide (30-fold over the antibody), no significant apoptosis induction was detected. A representative example of this analysis using A549 is shown in FIG. 1. A similar experiment in melanoma cells is shown in FIG. 6.

Figure 5:
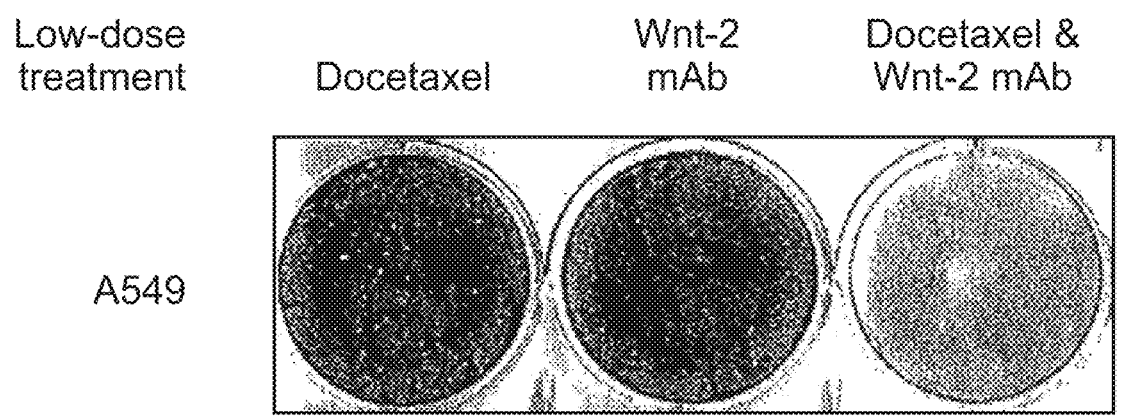
FIG. 5. Synergy with chemotherapy. A synergistic effect in A549 cells is observed when low dose chemotherapy (docetaxel) is combined with low dose of monoclonal anti Wnt2 antibody.

In addition, two primary cultures freshly made from a melanoma patient and a thyroid cancer patient were treated with the anti-Wnt2 monoclonal antibody, and significant cell lysis in both patients' primary cultures after antibody treatment was observed. Furthermore, when A549 cells were treated with low-dose anti-Wnt2 antibody (2.0 µg/ml) plus low-dose chemotherapy (0.01 nM Docetaxel), a synergistic effect was observed (FIG. 5).

TABLE 5

The Wnt2-targeted monoclonal antibody induces apoptosis in human cancer cell lines.

| Cell Lines | Wnt2 Protein Expression | Apoptosis Induction by Wnt2-targeted Monoclonal Antibody |
| --- | --- | --- |
| Normal, Control | | |
| NHBE | − | − |
| SAEC | − | − |
| LUNG CANCER | | |
| A549 | + | + |
| H1299 | + | + |
| H1703 | + | + |
| H460 | + | + |
| MESOTHELIOMA | | |
| MS-1 | + | + |
| H2052 | + | + |
| H513 | + | + |
| H290 | + | + |
| H28 | + | + |
| MELANOMA | | |
| LOX | + | + |
| FEMX | + | + |
| FEM | + | + |
| SK-MEL-2 | + | + |
| BREAST CANCER | | |
| Hu100 | + | + |
| MCF-7 | + | + |
| COLON CANCER | | |
| HCT-116 | + | + |
| SW480 | + | + |

Example 9

Anti-Wnt2 Monoclonal Antibody Inhibits Wnt Signaling and Induces Apoptosis Through Release of Cytochrome c, Down-Regulation of Survivin and Activation of Caspase-3

Figure 2:
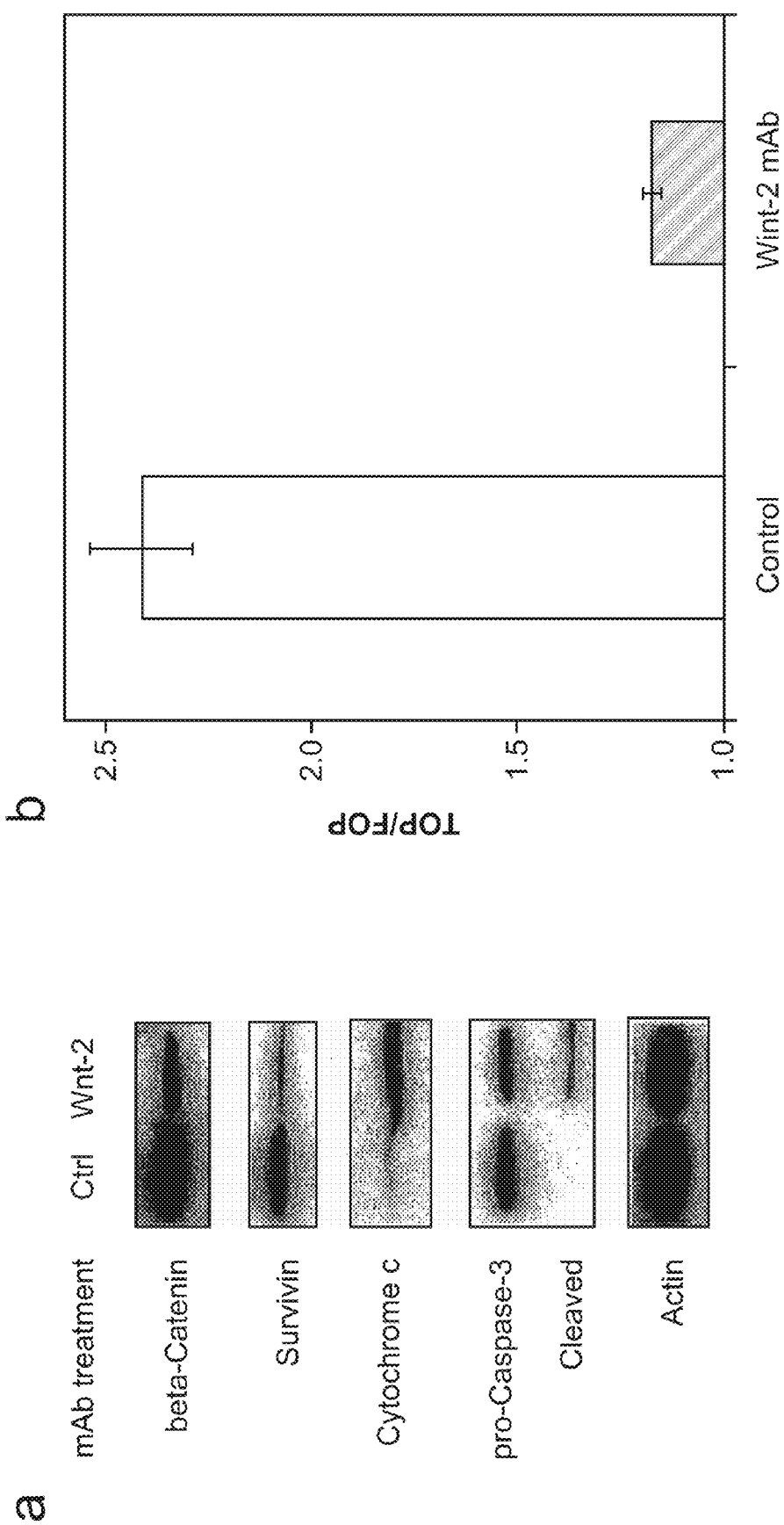
FIG. 2. Anti-Wnt2 monoclonal antibody decreases Wnt signaling and increases apoptotic signaling in NSCLC cell line A549. (a) Western analysis of β-catenin, Survivin, cytochrome c, pro- and cleaved caspase-3 of NSCLC a549 before and after anti-Wnt2 antibody treatment. (b) TOPFLASH assay of Tcf-dependent transcriptional activity in NSCLC cell line A549 after incubation with control or anti-Wnt2 monoclonal antibody.

Overexpression of Dvl-3 in NSCLC and mesothelioma has been reported (Uematsu et al., *Oncogene* 22(46):7218-21 (2003); Uematsu et al., *Cancer Res* 63(15):4547-51 (2003)). We found that both cytosolic β-catenin, and Dvl-3 were down-regulated after monoclonal anti-Wnt2 antibody treatment in cancer cells, including NSCLC cell line A549 (FIG. 2), melanoma cell lines FEMX and LOX (FIG. 6) and mesothelioma cell lines MS1, H28 and LRK1A (data not shown). In A549, FEMX and LOX cells in which the monoclonal anti-Wnt2 antibody induced apoptosis, the cleaved (active) form of caspase-3 was up-regulated (See, FIG. 2 for A549; FIG. 6 for FEMX and LOX). Consistent with this caspase-3 activity, increased levels of Cytochrome c in these cells after monoclonal anti-Wnt2 antibody treatment was detected (FIG. 6). In addition, an inhibitor of apoptosis (IAP) protein, Survivin, was also down-regulated in these cells after the antibody treatment (FIG. 6). Further, a significant reduction in TCF dependent transcriptional activity (TOPFLASH assay) (P<0.01) in the A549 cells after the monoclonal anti-Wnt2 antibody treatment was observed (FIG. 2). The β-catenin-TCF targeted genes, c-Myc and fibronectin, were also down-regulated after anti-Wnt2 monoclonal antibody treatment of LOX cells (FIG. 6.) and of primary tumor cultures freshly made from patients with malignant melanoma (FIG. 6).

Example 10

Wnt2 siRNA Induces Apoptosis in Cancer Cells

Figure 3:
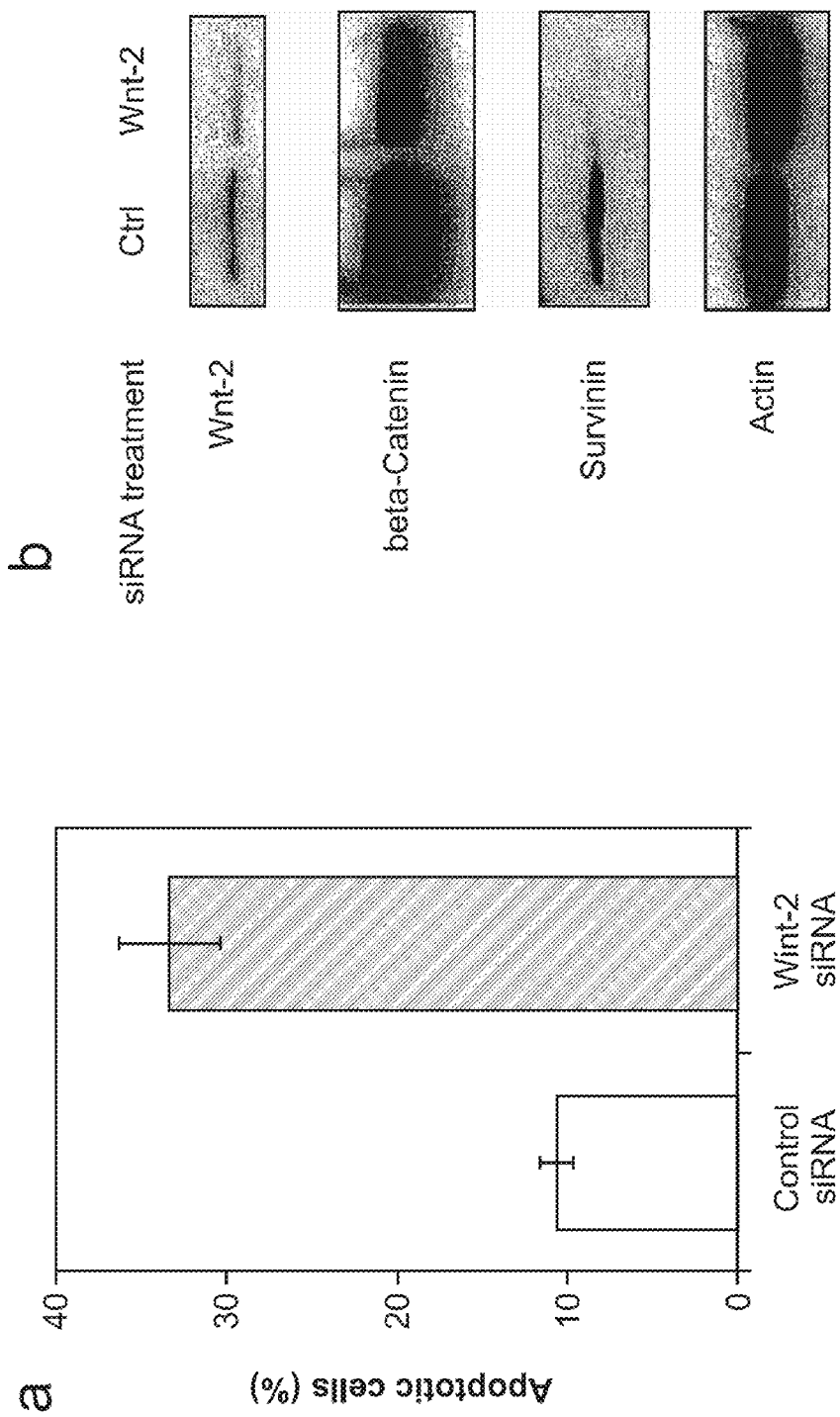
FIG. 3. Wnt2 siRNA induces apoptosis and blocks Wnt signal transduction in NSCLC cell line A549. (a) Annexin V analysis of apoptosis induced by Wnt2 siRNA. From left to right, A549 was treated with nonsilencing control siRNA and Wnt2 siRNA, respectively. (b) Western analysis of Wnt2, β-catenin, Survivin in A549 cells after Wnt2 siRNA treatment. Nonsilencing siRNA served as control.
Figure 7:
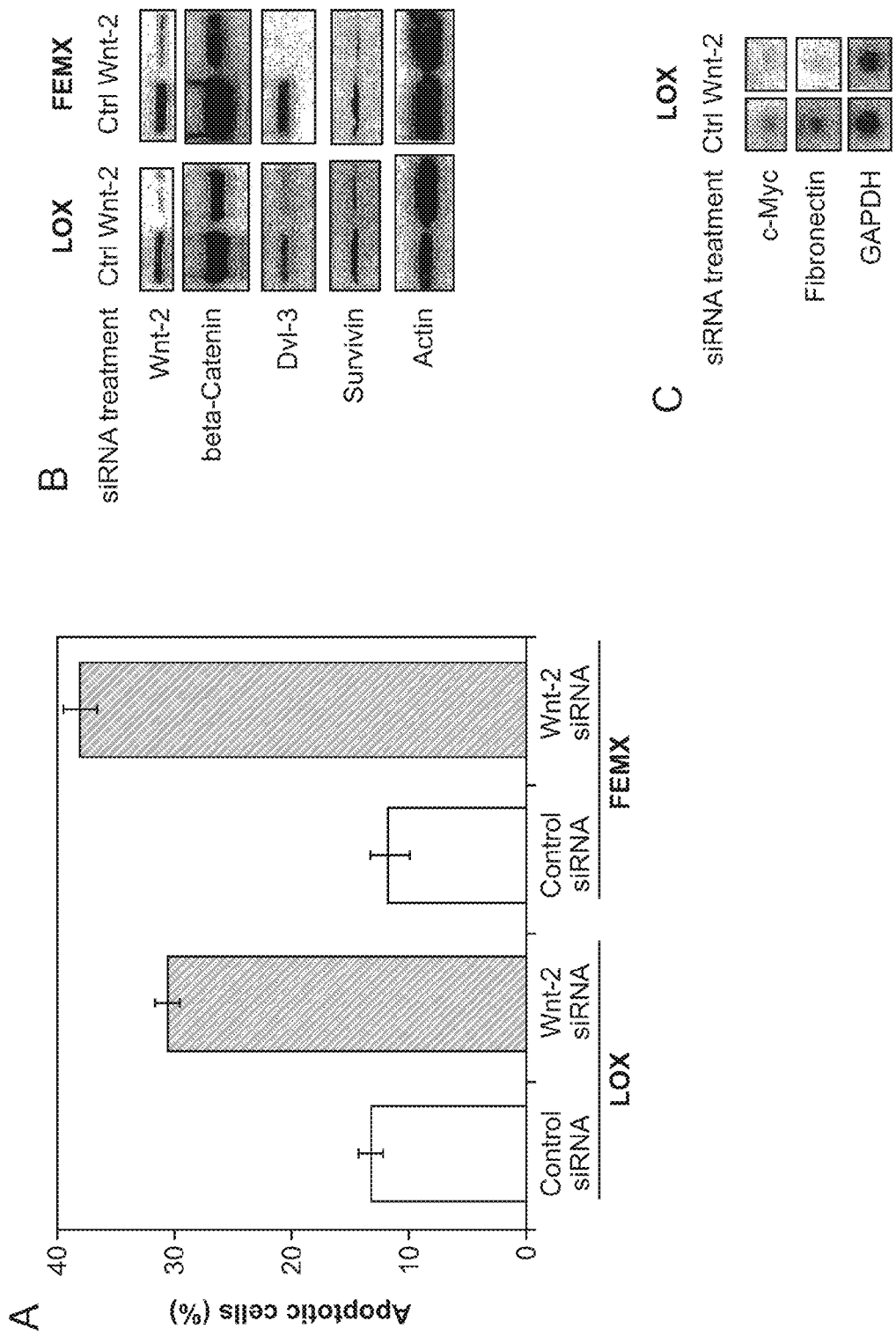
FIG. 7. Wnt2 siRNA induces apoptosis and blocks Wnt signal transduction in FEMX and LOX cancer cell lines. (a) Annexin V analysis of apoptosis induced by Wnt2 siRNA. LOX and FEMX cancer cells were treated with nonsilencing control siRNA and Wnt2 siRNA, respectively. (b) Western analysis of Wnt2, β-catenin, Survivin in LOX and FEMX cells after Wnt2 siRNA treatment. Actin served as a loading control. Nonsilencing siRNA served as control. (c) c-Myc and fibronectin genes were down-regulated after Wnt2 siRNA treatment in LOX cells. Total RNA was used for hybridization.
Figure 12:
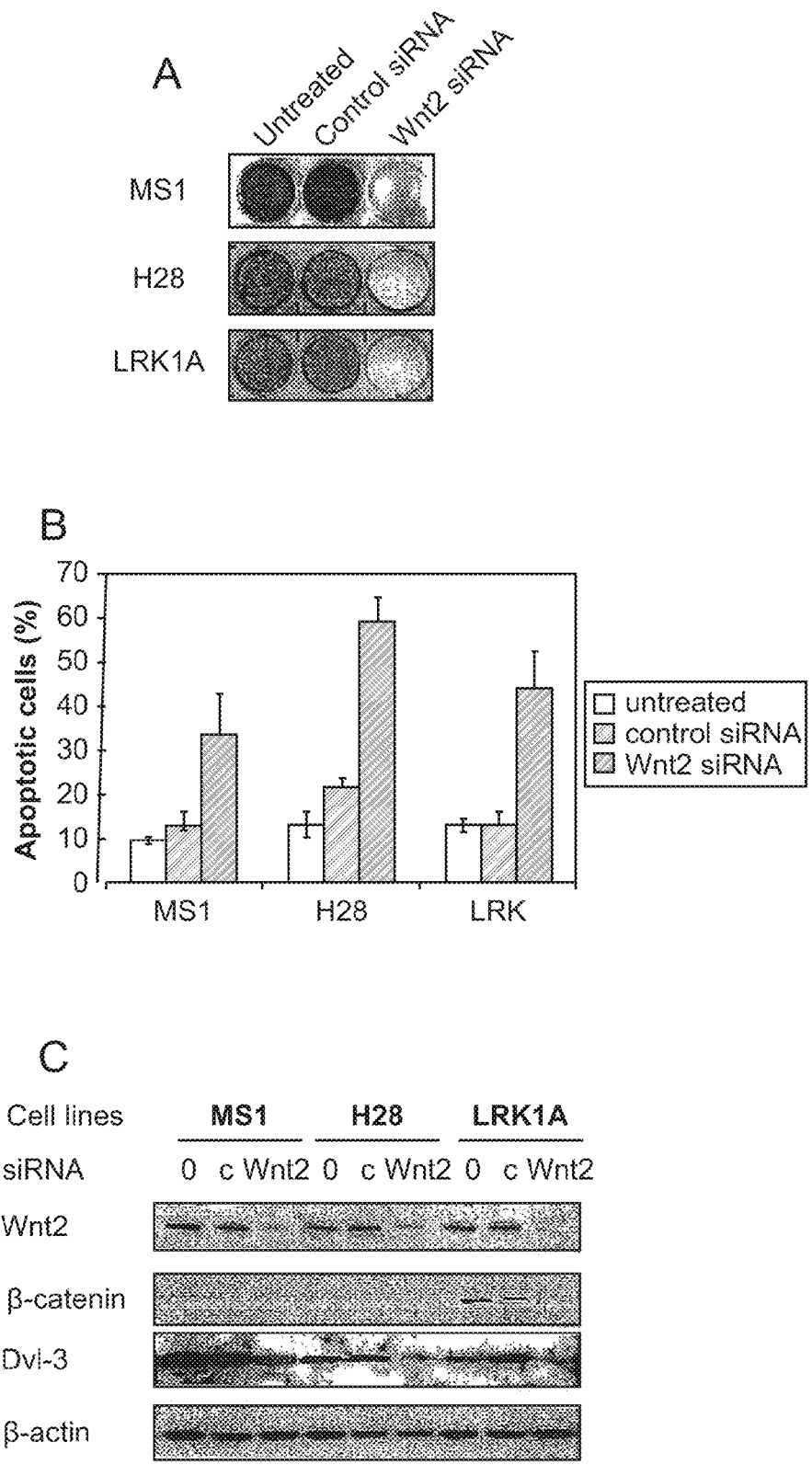
FIG. 12. Wnt2 siRNA induces apoptosis and blocks Wnt signal transduction in mesothelioma cell lines. (A) 0.5% Crystal Violet staining of three malignant pleural mesothelioma cell lines realized 35 days after transfection with lipofectamine alone (untreated), with a non-silencing siRNA (control siRNA) or 100 nM of a specific Wnt2 siRNA (Wnt2 siRNA). (B) Annexin V analysis of apoptosis induced by Wnt2 siRNA. Mesothelioma cells were transfected as described in A. (C) Western analysis after Wnt2 siRNA treatments (100 nM for 72 hrs), no treatments and non-silencing siRNA served as controls. Wnt2, Dvl-3, β-catenin were used as primary antibodies. β-actin served as a loading control.
Figure 13:
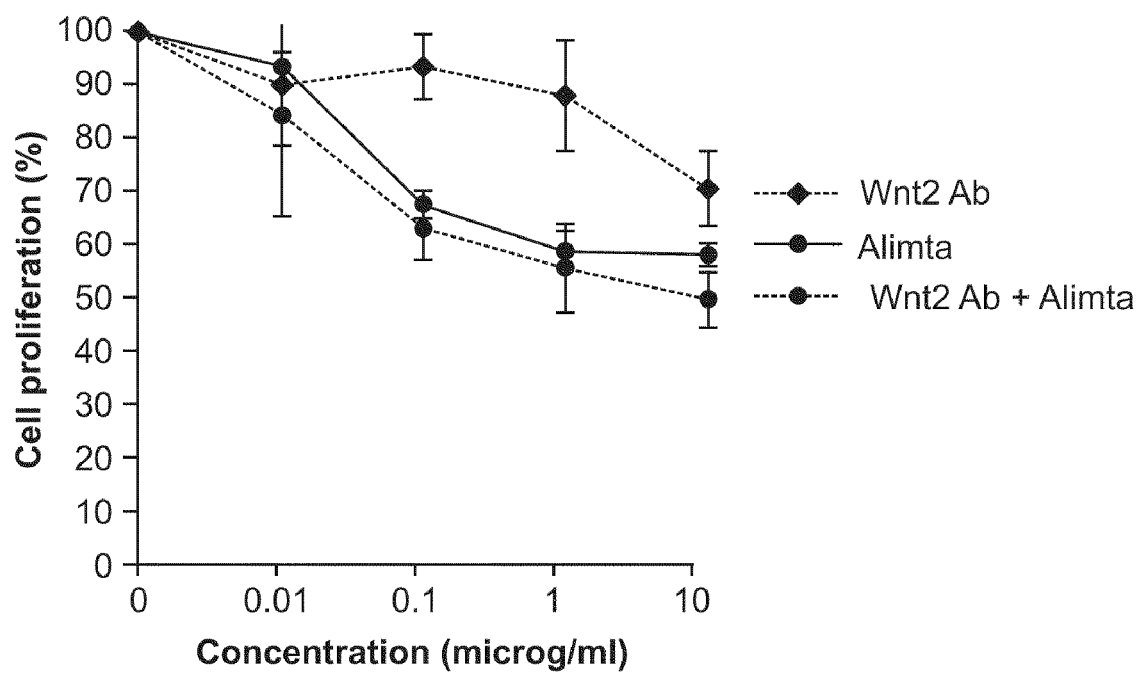
FIG. 13. Effects of Wnt2 antibody and Alimta® on cell proliferation. MS1 mesothelioma cell line was plated in 96-well plates and treated with increasing concentration of Wnt2 antibody (dotted line), Alimta® (solid line) or both (dashed line). Cell proliferation was assessed 3 days latter by measuring the metabolic activity of cellular enzyme (here the tetrazolium conversion). Results are the means±SD (error bars).

RNA interference was carried out by following the protocol described by Elbashir et al. (Elbashir et al., Methods 26 (2):199-213 (2002)) and Wnt2 targeted small interfering RNA (siRNA) was used to study the effect of Wnt2 mRNA silencing. Similar to the monoclonal anti-Wnt2 antibody, treatment with Wnt2 siRNA for 3-5 days induced apoptosis in all cancer cell lines expressing Wnt2 (See, FIG. 3 for A549 cells; FIG. 7 for LOX and FEMX cells; and FIG. 12 for MS1, H28 and LRK1A cells). Significant apoptosis was induced by 100 nM Wnt2 siRNA, and no apoptosis was induced by non-silencing siRNA control (100 nM) (P<0.01) (FIG. 3). Silencing of Wnt2 expression after Wnt2 siRNA treatments (100 nM for 72 hrs) was confirmed by Western blot analysis (FIG. 3 for A549 cells; FIG. 7 for LOX and FEMX cells; and FIG. 12 for MS1, H28 and LRK1A cells). Non-silencing siRNA served as control (100 nM for 72 hrs). To determine whether the apoptotic effects correlated with the inhibition of Wnt2 signaling, down-regulated expression levels for Dvl-3, cytosolic β-catenin, and Survivin were observed after Wnt2 siRNA treatment (FIG. 3 for A549 cells; FIG. 7 for LOX and FEMX cells; and FIG. 12 for MS1, H28 and LRK1A cells). The β-catenin-TCF targeted genes, c-Myc and fibronectin, were also found down-regulated in siRNA Wnt2 treated LOX cells (FIG. 7).

Example 11

Anti-Wnt2 Monoclonal Antibody Suppresses Tumor Growth In Vivo

Figure 4:
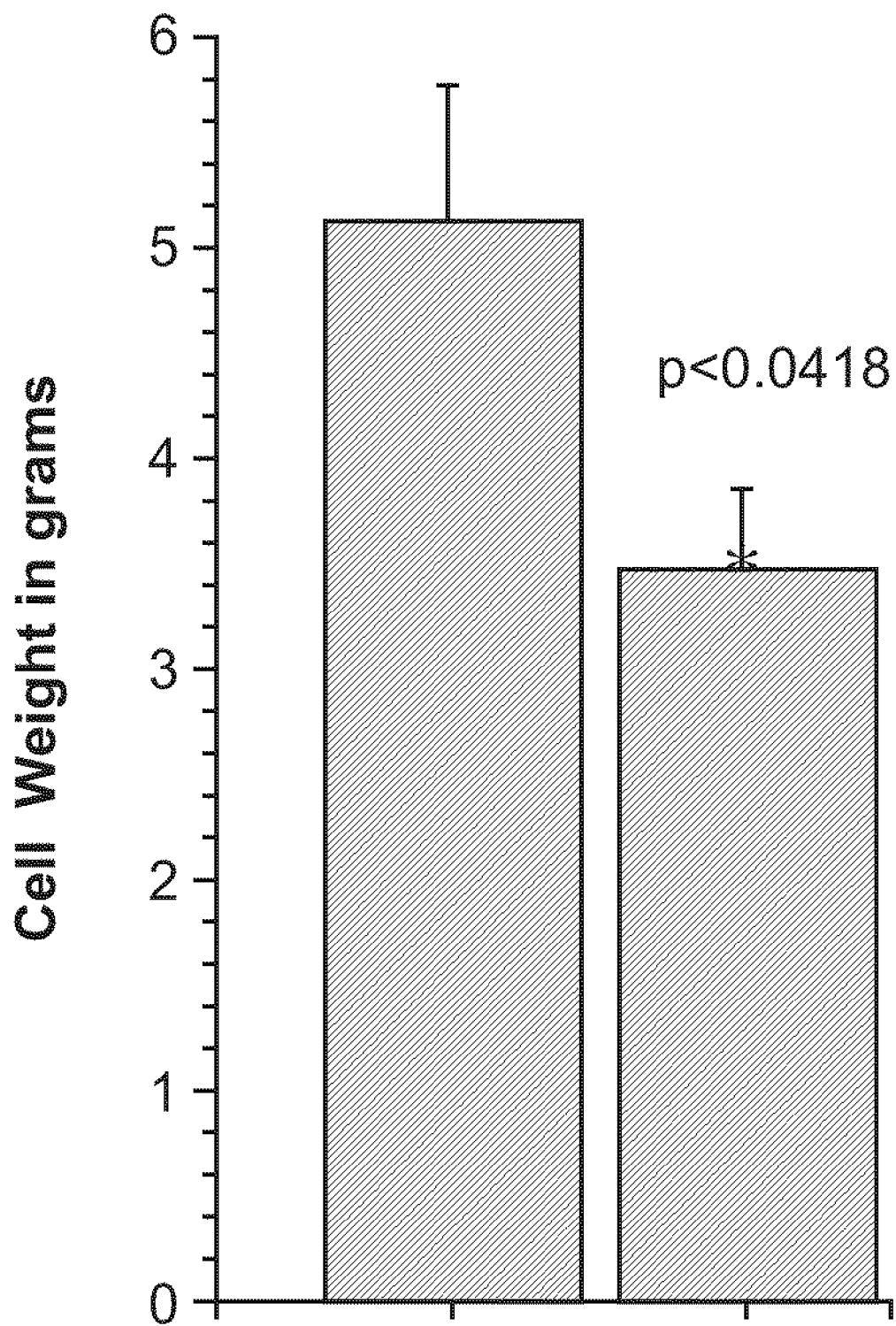
FIG. 4. In vivo study of anti Wnt2 monoclonal antibody on lung metastasis.

In vivo studies were carried out using a mouse model specific for tumor development in the lung. In one experiment, a malignant melanoma cell line, LOX, was inoculated through the tail vein into athymic nude mice at 3 million cells/per mouse. Ten mice were then treated with 250 μg of the monoclonal anti-Wnt2 antibody or PBS control via intraperitoneal (i.p.) injection twice a week for four weeks. Mice were sacrificed one week after. Lungs were collected surgically and weighed. Results were analyzed with Student's t-test. A difference in lung weight was observed between anti Wnt2 monoclonal antibody treated mice and untreated control mice (P<0.0418; FIG. 4).

Figure 8:
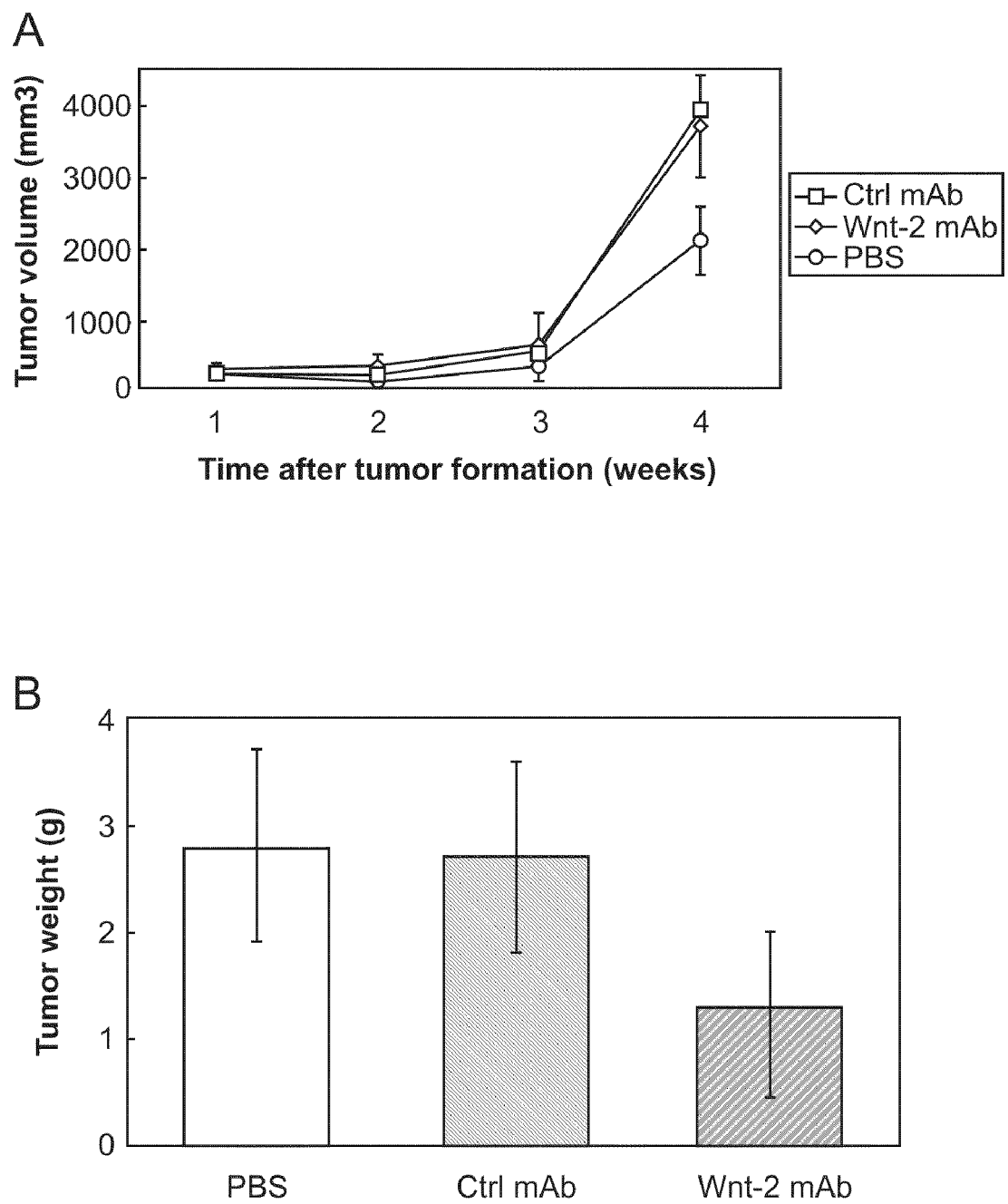
FIG. 8. Anti-Wnt2 monoclonal antibody suppresses tumor growth in vivo. (a) Anti-Wnt2 monoclonal antibody treatment (and control mAb and PBS treatment) was started 3 days after LOX tumor cell inoculation, and tumor volume ($mm^3$) is shown at various times after treatment. Results are the means±s.d. (error bars) for eight animals. (b) Tumor weight changes after treatment with PBS, control monoclonal antibody, or anti-Wnt2 monoclonal antibody, respectively. Results are the means±s.d. (error bars) for eight animals.

In another experiment, malignant melanoma LOX cells were injected s.c. into nude mice. The animals were then treated with 250 μg of the anti-Wnt2 monoclonal antibody, control antibody, or 100 μl PBS control via i.p. injections twice a week. The monoclonal anti-Wnt2 antibody significantly inhibited tumor growth versus control (FIG. 8). Suppression of tumor growth was seen when the anti-Wnt2 monoclonal antibody injection was started after the tumors were already established (three days after tumor cell inoculation) (P<0.005; FIGS. 8a and 8b). The tumor tissues were harvested and analyzed via TUNEL staining and apoptotic cells were noticed in those tumor tissues treated with the anti-Wnt2 monoclonal antibody.

Example 12

Administration of Anti-Wnt2 Monoclonal Antibody does not Show Noticeable Toxicity in Mouse Organs To address whether possible cytotoxic effects are caused by administration of monoclonal anti Wnt2 antibody, several tissue samples including brain, lung, kidney, heart, small intestine, large intestine, stomach, ovary, skin, muscle, liver, and bone of mice treated with monoclonal anti Wnt2 antibody were examined microscopically. Blinded analysis by an experienced pathologist failed to demonstrate noticeable toxicities or abnormalities among Wnt2 monoclonal antibody treated mice. Finally, the Wnt2 antibody treated mice appeared completely normal after 4 weeks of treatment. Tissue samples were surgically resected and embedded in paraffin blocks. Tissue dissections (5 um) were histochemically stained with eosin and examined under the light microscope by a certified mouse pathologist.

Example 13

Anti-Wnt2 Antibody-Induced Apoptosis is a Fast Process and Dose Dependent

A dosage and time course experiments on two NSCLC cell lines, H838 and A549, was performed. Flow cytometry analysis after about 32 hr incubation of anti-Wnt2 antibody showed that 1 μg/ml antibody could induce apoptosis. Anti-Wnt2 antibody at a concentration of 20 μg/ml caused dramatic apoptotic cell death. Anti-Wnt2 antibody (at concentration of 8 μg/ml) induced apoptosis could be detected as early as after 6 hr incubation and after 50 hr incubation almost all cells were found undergoing apoptosis or necrosis. In contrast, control anti-SOCS3 antibody did not have effect on those cancer cells in the parallel experiments. Anti-Wnt2 antibody incubation with normal lung cell line (CCL-75) was also insensitive to either time or dosage.

Example 14

Anti-Wnt2 Antibody-Induced Apoptosis is Associated with Releasing of Smac/Diablo and Cytochrome C from Mitochondria to the Cytosol and JNK Activation During apoptosis, Smac/Diablo (second mitochondria-derived activator of caspase/direct IAP-binding protein with low pI) functions to remove the IAP-mediated caspase inhibition. Stimulation of apoptosis causes releasing of Smac/Diablo from the intermembrane space of mitochondria into the cytosol, together with cytochrome c. Cytochrome c directly activates Apaf-1 and caspase-9 and Smac/Diablo interacts with multiple IAPs to remove IAP-mediated inhibition of both initiator and effector caspases. Consistent with above results where caspase-3 activity increases in the cancer cells, but not in the normal cells, an increased level of both Smac/Diablo and cytochrome c in the cytosol of the cancer cells after anti-Wnt2 antibody treatment, but not in that of the normal cells was observed. These results indicate that both Smac/Diablo and cytochrome c are likely involved in anti-Wnt2 antibody induced apoptosis by removing survivin and/or other IAPs-mediated inhibition and direct activation of caspases, respectively.

Example 15

Role of Dvl Activation in Non Small Cell Lung Cancer

The role of Dvl activation in non small-cell lung cancer (NSCLC) was also examined. This example demonstrated that Dvl-3 is overexpressed in freshly resected NSCLC and established NSCLC cell lines. Thus, additional evidence is provided that Wnt2 signaling through canonical β-catenin pathways is due to upstream events, such as Dvl expression.

Dvl expression and function was analyzed in order to evaluate the function of Wnt2 signaling in NSCLC. Eight NSCLC fresh tumors (four squamous cell and four adenocarcinomas) and their autologous matched normal lung tissue were obtained from patients undergoing resection of their tumors as part of their treatment for early stage I NSCLC. Patients had not received any prior treatment, e.g., chemotherapy. Western blot analysis of these samples showed that in 75% (three of four squamous cell carcinomas and three of four adenocarcinomas) of all cancer cells tested, Dvl-3 was overexpressed while the corresponding matched normal microdissected lung tissues failed to show expression of Dvl-3. Furthermore, seven of eight NSCLC tumors with Dvl-3 overexpression showed higher expression of Wnt2 by western blot analysis. Expression of Dvl-1 or Dvl-2 was not detected.

Example 16

Effects of Anti-Wnt2 Monoclonal Antibody, Alimta® Alone and in Combination on Cell Proliferation The effects of the anti-Wnt2 monoclonal antibody on cell proliferation were assessed and compared with the effects of Alimta®. Alimta® (LY231514, MTA, pemetrexed) is a novel multifunctional antifolate antimetabolite (Hanauske *Lung Cancer* 45 Suppl 1:S121-4 (2004)). Recently, a phase III trial showed that the combination of Alimta® with cisplatine resulted in a significantly increased efficacy compared with cisplatine alone (Vogelzang et al. *J. Clin. Oncol.* 21:2636-44 (2003)). Alimta® is now considered a standard in the treatment of surgically non-amenable mesothelioma. MS1 mesothelioma cells were plated in 96-well plates and treated with increasing concentrations of the Wnt2 antibody, Alimta® or both. Three days later the cell proliferation was assessed by measuring the metabolic activity of cellular enzyme (here the tetrazolium conversion). A decrease of about 30% (SD +/−7%) in cell proliferation was observed when the anti-Wnt2 antibody was used at a concentration of 10 µg/ml. Alimta® treatment induced a decrease in cell proliferation of about 41.9% (SD +/−4%) at a concentration of 1 µg/ml and of about 42.9% (SD +/−2%) at a concentration of 10 µg/ml. When the anti Wnt2 monoclonal antibody and Alimta® were used together at a concentration of 10 µg/ml, cell proliferation was inhibited by about 51.2% (SD +/−5%, p<0.005).

Discussion

As noted above, little is known regarding the role that wnt ligand plays in human carcinogenesis. The data presented here demonstrate that wnt signals play a causal role in human cancer cells and thus are cancer therapeutic targets.

The data presented above demonstrate that the anti-Wnt2 antibodies can induce apoptosis in human cancer cells. Furthermore, our data indicates that the anti-tumor effect was due to the blockade of wnt signaling pathway. The apoptotic cell death induced by anti-Wnt antibody was not only correlated with the Wnt protein expression, but also consistent with the decreased dvl and cytosolic β catenin protein expression in the human tumor cells tested. Conversely, both Dvl and cytosolic β-catenin proteins remain the same level in normal cell lines after anti-Wnt antibody treatment. The antibodies showed no detectable effect on normal cell lines, suggesting that the anti-Wnt2 antibody could specifically induce apoptosis in cancer cells, but not in normal cells. Given the possibility that polyclonal antibodies may generate non-specific effects, we used an anti-Wnt2 monoclonal antibody to further investigate the specificity of the effect of anti-Wnt2 antibodies. The anti-Wnt2 monoclonal antibody was able to induce apoptosis in human cancer cell lines that over-express Wnt2 protein, e.g., human lung cancer cell line. Similar to the results obtained from polyclonal antibody study, both dvl and cytosolic β catenin proteins were decreased after the anti-Wnt2 monoclonal antibody treatment in these tumor cells. However, the anti-Wnt2 monoclonal antibody showed much higher specificity than the anti-Wnt2 polyclonal antibody, e.g., the anti-Wnt2 monoclonal induces apoptosis only in the tumor cells that over-express Wnt2 protein (A549, LOX and FEMX), and has no detectable effect in the tumor cells that express Wnt2 protein; the anti-Wnt-1 polyclonal antibody induces apoptotic cell death in the tumor cells that over-express Wnt2. Taken together, these data indicate that the anti-Wnt2 antibody treatment can induce tumor-specific apoptosis and down-regulate the Wnt-dvl-β catenin signaling pathway in human cancer cells.

Through frizzled receptor and disheveled protein, Wnt signal activates two distinct pathways: the canonical pathway (i.e., β catenin pathway) and the JNK pathway. Disheveled protein has three highly conserved domains, DIX, PDZ, and DEP. Among them, the DIX and PDZ domains are necessary for the canonical signaling pathway while the DEP domain is important for the activation of JNK pathway. It has been suggested that the activation of JNK plays a critical role in initiating apoptosis (Wang, C. Y. et al., *Mol Cell Biol* 19 (9):5923-9 (1999)). Recently, Chen et al. have demonstrated that Wnt-1 inhibits apoptosis by activating β catenin and TCF transcription (Chen, S. et al., *J Cell Biol* 152 (1):87-96 (2001)). In this study, both overexpression of β-catenin and increased JNK activity were observed after anti-Wnt antibody treatment, suggesting that both the canonical pathway and the JNK pathway are involved in the apoptosis induced by anti-Wnt antibody. In addition, overexpression of Dvl in a normal mesothelial cell line down regulated JNK activities and the inhibition of Dvl by using Apigenin to block CK-2 activity increased JNK activity. Most likely, the activation of JNK after anti-Wnt antibody treatment is through Dvl.

Furthermore, siRNA-mediated inhibition of Dvl expression in NSCLC cells decreased β-catenin-mediated Tcf transcription, which further supports that Dvl overexpression is important to the canonical Wnt/B-catenin pathway in some lung cancer cells. Inhibition of Dvl also suppressed cell growth and colony formation in NSCLC cells, which indicates that aberrant upstream events in Wnt signaling is related to tumorigenesis in NSCLC.

Degradation of Dvl by siRNA resulted in growth suppression in H1703, but not in A549 cells. These are both squamous cell lung cancer cell lines, but H1703 has mutational inactivation of p53 whereas A549 has wild-type p53. The p53 status may therefore explain, at least in part, the differences in Dvl function between the two squamous cell lung cancer cell lines treated.

To further elucidate the mechanism through which anti-Wnt antibody induce apoptosis in human cancer cells, we have examined other possible components in the apoptotic pathway. For instance, releasing of Smac/Diablo into cytosol was detected in these tumor cells treated with wnt antibody. Smac/Diablo (second mitochondria-derived activator of caspase/direct IAP-binding protein with low pI) (Du, C. et al., *Cell* 102 (1):33-42 (2000); Verhagen, A. M. et al., *Cell* 102 (1):43-53 (2000)) functions by releasing the IAP-mediated caspase inhibition. Stimulation of apoptosis causes releasing of Smac/Diablo from the intermembrane space of mitochondria into the cytosol, together with cytochrome c. Cytochrome c directly activates Apaf-1 and caspase-9 and Smac/Diablo interacts with multiple IAPs to remove IAP-mediated inhibition of both initiator and effector caspases (Chai, J. et al., *Nature* 406 (6798):855-62 (2000); Srinivasula, S. M. et al., *J_Biol_Chem* 275 (46):36152-7 (2000)). Consistent with above results where caspase-3 activity increases in the cancer cells, but not in the normal cells, we found increase level of both Smac/Diablo and cytochrome c in the cytosol of the cancer cells after anti-Wnt antibody treatment, but not in that of the normal cells. Our results indicate that both Smac/Diablo and cytochrome c are likely involved in this anti-Wnt antibody induced apoptosis by removing survivin and/or other IAPs-mediated inhibition and direct activation of caspases, respectively.

The above findings suggest that wnt antibodies may not only induce directly apoptosis in cancer cell that overexpress wnt proteins, but also release potentially drug resistance by restoring normal apoptotic machinery back to these tumor cells. The basis for drug resistance in tumor cells is most likely the disruption of apoptosis. Over expression of Survivin, an inhibitor of apoptosis, is a common feature of most human cancers. It has been shown that targeting of survivin increases the sensitivity of tumor cells to cytotoxic drugs (Grossman, D. et al., *Proc Natl Acad Sci USA* 98 (2):635-40 (2001)). It has been shown that antisense survivin is sufficient to cause apoptosis in human mesothelioma cells. Moreover, a synergistic effect between antisense surviving and chemotherapy has also been reported.

We have shown that wnt antibody treatment dramatically decreases the protein expression level of Survivin. Taken together, Wnt antibody should potentiate and synergize the effect of standard chemotherapy in human cancer cells.

Other antagonists of Wnt signal or Frizzled receptor should also induce apoptosis through disheveled. For instance, sFRPs function as soluble modulators of Wnt signaling by competing with the Frizzled receptors for the binding of secreted Wnt ligands (Melkonyan, H. S. et al., *Proc Natl Acad Sci USA* 94 (25):13636-41 (1997)). Specifically, sFRPs can either antagonize Wnt function by binding the protein and blocking access to its cell surface signaling receptor, or they can enhance Wnt activity by facilitating the presentation of ligand to the Frizzled receptors (Uthoff, S. M. et al., *Mol Carcinog* 31 (1):56-62 (2001)). Frizzled receptor antagonists (e.g., antibody specific for the extracellular domain or small molecule specific for the intracellular domain) should induce apoptosis in human cancer cells that overexpress wnt/frizzled proteins.

In summary, our results indicate that wnt monoclonal antibodies can induce tumor-specific apoptosis in human cancer cells, probably through both the canonical and the JNK pathways. Our data demonstrate that Wnt/Frizzled is a useful therapeutic targets for the treatment of cancer, and the results from xenograft mouse model implicate that Wnt monoclonal antibodies are good candidates of tumor-targeting cancer therapeutics.

In this example, we show that genetic alterations in frizzled (fz) genes and/or LRP (LDL-related protein) genes result in mutant and/or truncated forms of all Fz receptors and/or LRP co-receptors (extracellular, transmembrane, and/or intracellular domains) in cancers. The cancer types that we tested include breast cancer, colon cancer, prostate cancer, lung cancer, mesothelioma, and sarcoma. The genetic alterations mentioned above include chromosomal deletion (homozygous or heterozygous), chromosomal translocation, chromosomal breaks, chromosomal inversions, internal small deletions, insertions, and point mutations. These mutant and/or truncated forms of Fz receptors and/or LRP co-receptors result in constitutive signaling regardless presence of Wnt ligands, which in turn result in constitutive downstream transcriptional activities in cancers. In contrast, there are no mutant forms of Fz receptors and/or LRP co-receptors in normal cells/tissues.

This invention demonstrates that mutant and/or truncated forms of Fz receptors and/or LRP co-receptors for the Wnt signaling pathway are cancer specific. They have very strong potential to be used as targets for developing therapeutic drugs (e.g., small molecules, chemical compounds, antibodies, antisense-oligos or RNAi as discussed above). These drugs are able to target cancers only, but not normal cells. Thus, this invention will be of great help in therapeutic strategies for treatment of a number of cancers as noted above, including colon cancer, breast cancer, lung cancer, e.g., NSCLC, mesothelioma and sarcoma, and the like.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of reducing the proliferation of a human cancer cell that overexpresses a Wnt2 protein in a patient comprising:
   administering to said patient an antibody specific for an epitope within amino acids 49-63 of the Wnt2 protein, wherein said administering reduces the proliferation of said human cancer cell.

2. The method of claim 1, wherein the antibody is a humanized antibody.

3. The method of claim 1, wherein the antibody is a single chain Fv fragment (scFv).

4. The method of claim 1, wherein the antibody competes for binding to a Wnt2 protein with an antibody that comprises
   (i) a $V_L$CDR1 comprising an amino acid sequence of SEQ ID NO:56, NO:104, or NO:125;
   (ii) a $V_L$CDR2 comprising an amino acid sequence of SEQ ID NO:58;
   (iii) a $V_L$CDR3 comprising an amino acid sequence of SEQ ID NO:60, NO:84, NO:107, NO:126, or NO:138;
   (iv) a $V_H$CDR1 comprising an amino acid sequence of SEQ ID NO:63 or NO:87;
   (v) a $V_H$CDR2 comprising an amino acid sequence of SEQ ID NO:65 or NO:89; and
   (vi) a $V_H$CDR3 comprising an amino acid sequence of SEQ ID NO:67, NO:91, or NO:110.

5. The method of claim 1, wherein the cancer cell is melanoma.

6. The method of claim 1, wherein the cancer cell is a lung cancer cell.

7. The method of claim 1, further comprising administering a second cancer therapeutic agent to said patient.

8. The method of claim 7, wherein said second therapeutic agent is an agent for chemotherapy.

9. A method of reducing the proliferation of a human cancer cell that overexpresses a Wnt2 protein in a patient comprising:
   administering to said patient an antibody specific for the Wnt2 protein,
   wherein the antibody competes for binding to a Wnt2 protein with an antibody that comprises
   (i) a $V_L$CDR1 comprising an amino acid sequence of SEQ ID NO:56, NO:104, or NO:125;
   (ii) a $V_L$CDR2 comprising an amino acid sequence of SEQ ID NO:58;
   (iii) a $V_L$CDR3 comprising an amino acid sequence of SEQ ID NO:60, NO:84, NO:107, NO:126, or NO:138;
   (iv) a $V_H$CDR1 comprising an amino acid sequence of SEQ ID NO:63 or NO:87;
   (v) a $V_H$CDR2 comprising an amino acid sequence of SEQ ID NO:65 or NO:89; and
   (vi) a $V_H$CDR3 comprising an amino acid sequence of SEQ ID NO:67, NO:91, or NO:110;
   wherein said administering reduces the proliferation of said human cancer cell.

10. The method of claim 9, wherein the antibody is a humanized antibody.

11. The method of claim 9, wherein the antibody is a single chain Fv fragment (scFv).

12. The method of claim 9, wherein the cancer cell is melanoma.

13. The method of claim 9, wherein the cancer cell is a lung cancer cell.

14. The method of claim 9, further comprising administering a second cancer therapeutic agent to said patient.

15. The method of claim 14, wherein said second therapeutic agent is an agent for chemotherapy.

* * * * *

SEQUENCE LISTING

<160> NUMBER OF SEQ ID NOS: 160

<210> SEQ ID NO 1
<211> LENGTH: 360
<212> TYPE: PRT
<213> ORGANISM: Homo sapiens
<220> FEATURE:

-continued

<223> OTHER INFORMATION: human wingless-type MMTV integration site
family member 2 precursor (Wnt2), including signal
peptide, peptide sequence #1

<400> SEQUENCE: 1

Met Asn Ala Pro Leu Gly Gly Ile Trp Leu Trp Leu Pro Leu Leu
1               5                   10                  15

Thr Trp Leu Thr Pro Glu Val Asn Ser Ser Trp Trp Tyr Met Arg Ala
            20                  25                  30

Thr Gly Gly Ser Ser Arg Val Met Cys Asp Asn Val Pro Gly Leu Val
        35                  40                  45

Ser Ser Gln Arg Gln Leu Cys His Arg His Pro Asp Val Met Arg Ala
    50                  55                  60

Ile Ser Gln Gly Val Ala Glu Trp Thr Ala Glu Cys Gln His Gln Phe
65                  70                  75                  80

Arg Gln His Arg Trp Asn Cys Asn Thr Leu Asp Arg Asp His Ser Leu
                85                  90                  95

Phe Gly Arg Val Leu Leu Arg Ser Ser Arg Glu Ser Ala Phe Val Tyr
            100                 105                 110

Ala Ile Ser Ser Ala Gly Val Val Phe Ala Ile Thr Arg Ala Cys Ser
        115                 120                 125

Gln Gly Glu Val Lys Ser Cys Ser Cys Asp Pro Lys Lys Met Gly Ser
    130                 135                 140

Ala Lys Asp Ser Lys Gly Ile Phe Asp Trp Gly Gly Cys Ser Asp Asn
145                 150                 155                 160

Ile Asp Tyr Gly Ile Lys Phe Ala Arg Ala Phe Val Asp Ala Lys Glu
                165                 170                 175

Arg Lys Gly Lys Asp Ala Arg Ala Leu Met Asn Leu His Asn Asn Arg
            180                 185                 190

Ala Gly Arg Lys Ala Val Lys Arg Phe Leu Lys Gln Glu Cys Lys Cys
        195                 200                 205

His Gly Val Ser Gly Ser Cys Thr Leu Arg Thr Cys Trp Leu Ala Met
    210                 215                 220

Ala Asp Phe Arg Lys Thr Gly Asp Tyr Leu Trp Arg Lys Tyr Asn Gly
225                 230                 235                 240

Ala Ile Gln Val Val Met Asn Gln Asp Gly Thr Gly Phe Thr Val Ala
                245                 250                 255

Asn Glu Arg Phe Lys Lys Pro Thr Lys Asn Asp Leu Val Tyr Phe Glu
            260                 265                 270

Asn Ser Pro Asp Tyr Cys Ile Arg Asp Arg Glu Ala Gly Ser Leu Gly
        275                 280                 285

Thr Ala Gly Arg Val Cys Asn Leu Thr Ser Arg Gly Met Asp Ser Cys
    290                 295                 300

Glu Val Met Cys Cys Gly Arg Gly Tyr Asp Thr Ser His Val Thr Arg
305                 310                 315                 320

Met Thr Lys Cys Gly Cys Lys Phe His Trp Cys Cys Ala Val Arg Cys
                325                 330                 335

Gln Asp Cys Leu Glu Ala Leu Asp Val His Thr Cys Lys Ala Pro Lys
            340                 345                 350

Asn Ala Asp Trp Thr Thr Ala Thr
        355                 360

<210> SEQ ID NO 2
<211> LENGTH: 15
<212> TYPE: PRT
<213> ORGANISM: Artificial Sequence

```
<220> FEATURE:
<223> OTHER INFORMATION: Description of Artificial Sequence:human Wnt2
      antigenic peptide sequence #2

<400> SEQUENCE: 2

Ser Ser Gln Arg Gln Leu Cys His Arg His Pro Asp Val Met Arg
1               5                   10                  15

<210> SEQ ID NO 3
<211> LENGTH: 19
<212> TYPE: PRT
<213> ORGANISM: Artificial Sequence
<220> FEATURE:
<223> OTHER INFORMATION: Description of Artificial Sequence:human Wnt2
      antigenic peptide sequence #3

<400> SEQUENCE: 3

Pro Leu Gly Gly Ile Trp Leu Trp Leu Pro Leu Leu Leu Thr Trp Leu
1               5                   10                  15

Thr Pro Glu

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence:human Wnt2
      antigenic peptide sequence #4

<400> SEQUENCE: 4

Ser Arg Val Met Cys Asp Asn Val Pro Gly Leu Val
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence:human Wnt2
      antigenic peptide sequence #5

<400> SEQUENCE: 5

Ala Glu Cys Gln His Gln Phe Arg Gln His
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence:human Wnt2
      antigenic peptide sequence #6

<400> SEQUENCE: 6

Arg Asp His Ser Leu Phe Gly Arg Val Leu Leu Arg
1               5                   10

<210> SEQ ID NO 7
<211> LENGTH: 32
<212> TYPE: PRT
<213> ORGANISM: Artificial Sequence
<220> FEATURE:
<223> OTHER INFORMATION: Description of Artificial Sequence:human Wnt2
      antigenic peptide sequence #7

<400> SEQUENCE: 7

Glu Ser Ala Phe Val Tyr Ala Ile Ser Ser Ala Gly Val Val Phe Ala
1               5                   10                  15
```

```
Ile Thr Arg Ala Cys Ser Gln Gly Glu Val Lys Ser Cys Ser Cys Asp
            20                  25                  30

<210> SEQ ID NO 8
<211> LENGTH: 14
<212> TYPE: PRT
<213> ORGANISM: Artificial Sequence
<220> FEATURE:
<223> OTHER INFORMATION: Description of Artificial Sequence:human Wnt2
      antigenic peptide sequence #8

<400> SEQUENCE: 8

Cys Asp Pro Lys Lys Met Gly Ser Ala Lys Asp Ser Lys Gly
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence:human Wnt2
      antigenic peptide sequence #9

<400> SEQUENCE: 9

Tyr Gly Ile Lys Phe Ala Arg Ala Phe Val Asp
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence:human Wnt2
      antigenic peptide sequence #10

<400> SEQUENCE: 10

Val Asp Ala Lys Glu Arg Lys Gly Lys Asp Ala Arg
1               5                   10

<210> SEQ ID NO 11
<211> LENGTH: 23
<212> TYPE: PRT
<213> ORGANISM: Artificial Sequence
<220> FEATURE:
<223> OTHER INFORMATION: Description of Artificial Sequence:human Wnt2
      antigenic peptide sequence #11

<400> SEQUENCE: 11

Leu Lys Gln Glu Cys Lys Cys His Gly Val Ser Gly Ser Cys Thr Leu
1               5                   10                  15

Arg Thr Cys Trp Leu Ala Met
            20

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence:human Wnt2
      antigenic peptide sequence #12

<400> SEQUENCE: 12

Gly Ala Ile Gln Val Val Met
1               5

<210> SEQ ID NO 13
<211> LENGTH: 16
```

```
<212> TYPE: PRT
<213> ORGANISM: Artificial Sequence
<220> FEATURE:
<223> OTHER INFORMATION: Description of Artificial Sequence:human Wnt2
      antigenic peptide sequence #13

<400> SEQUENCE: 13

Lys Asn Asp Leu Val Tyr Phe Glu Asn Ser Pro Asp Tyr Cys Ile Arg
1               5                   10                  15

<210> SEQ ID NO 14
<211> LENGTH: 22
<212> TYPE: PRT
<213> ORGANISM: Artificial Sequence
<220> FEATURE:
<223> OTHER INFORMATION: Description of Artificial Sequence:human Wnt2
      antigenic peptide sequence #14

<400> SEQUENCE: 14

Thr Ala Gly Arg Val Cys Asn Leu Thr Ser Arg Gly Met Asp Ser Cys
1               5                   10                  15

Glu Val Met Cys Cys Gly
            20

<210> SEQ ID NO 15
<211> LENGTH: 17
<212> TYPE: PRT
<213> ORGANISM: Artificial Sequence
<220> FEATURE:
<223> OTHER INFORMATION: Description of Artificial Sequence:human Wnt2
      antigenic peptide sequence #15

<400> SEQUENCE: 15

Asp Val His Thr Cys Lys Ala Pro Lys Asn Ala Asp Trp Thr Thr Ala
1               5                   10                  15

Thr

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence:human Wnt2
      cDNA reverse transcription PCR (RT-PCR) primer pair #1

<400> SEQUENCE: 16
agtctgacct gatgcagacg                                              20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence:human Wnt2
      cDNA reverse transcription PCR (RT-PCR) primer pair #1

<400> SEQUENCE: 17
ccagtgttct tgcagatcca                                              20

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence:human Wnt2
      cDNA reverse transcription PCR (RT-PCR) primer pair #2

<400> SEQUENCE: 18
```

```
atgaacgccc ctctcggtgg a                                             21
```

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence:human Wnt2
      cDNA reverse transcription PCR (RT-PCR) primer pair #2

<400> SEQUENCE: 19

```
tcatgtagcg gttgtccagt                                               20
```

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence:human Wnt2
      cDNA reverse transcription PCR (RT-PCR) primer pair #3

<400> SEQUENCE: 20

```
gtggatgcaa aggaaaggaa                                               20
```

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence:human Wnt2
      cDNA reverse transcription PCR (RT-PCR) primer pair #3

<400> SEQUENCE: 21

```
agccagcatg tcctgagagt                                               20
```

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence:human Wnt2
      cDNA reverse transcription PCR (RT-PCR) primer pair #4

<400> SEQUENCE: 22

```
cgggaatctg cctttgttta                                               20
```

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence:human Wnt2
      cDNA reverse transcription PCR (RT-PCR) primer pair #4

<400> SEQUENCE: 23

```
ttcctttcct ttgcatccac                                               20
```

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence:human Wnt2
      cDNA reverse transcription PCR (RT-PCR) primer pair #5

<400> SEQUENCE: 24

```
ctccctctgc tcttgacctg                                               20
```

-continued

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence:human Wnt2
      cDNA reverse transcription PCR (RT-PCR) primer pair #5

<400> SEQUENCE: 25
cacatctgga tgtcggtgac                                                   20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence:human Wnt2
      cDNA reverse transcription PCR (RT-PCR) primer pair #6

<400> SEQUENCE: 26
cgaagtagtc gggaatctgc                                                   20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence:human Wnt2
      cDNA reverse transcription PCR (RT-PCR) primer pair #6

<400> SEQUENCE: 27
ttcctttcct ttgcatccac                                                   20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence:human Wnt2
      cDNA reverse transcription PCR (RT-PCR) primer pair #7

<400> SEQUENCE: 28
cagggtgatg tgcgataatg                                                   20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence:human Wnt2
      cDNA reverse transcription PCR (RT-PCR) primer pair #7

<400> SEQUENCE: 29
gcagattccc gactacttcg                                                   20

<210> SEQ ID NO 30
<211> LENGTH: 22
<212> TYPE: PRT
<213> ORGANISM: Artificial Sequence
<220> FEATURE:
<223> OTHER INFORMATION: Description of Artificial Sequence:human Wnt2
      antigenic peptide sequence #16

<400> SEQUENCE: 30

Arg Val Met Cys Asp Asn Val Pro Gly Leu Val Ser Ser Gln Arg Gln
1               5                   10                  15

```
Leu Cys His Arg His Pro
            20

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence:human Wnt2
      antigenic peptide sequence #17

<400> SEQUENCE: 31

Glu Cys Gln His Gln Phe Arg
1               5

<210> SEQ ID NO 32
<211> LENGTH: 12
<212> TYPE: PRT
<213> ORGANISM: Artificial Sequence
<220> FEATURE:
<223> OTHER INFORMATION: Description of Artificial Sequence:human Wnt2
      antigenic peptide sequence #18

<400> SEQUENCE: 32

Asp His Ser Leu Phe Gly Arg Val Leu Leu Arg Ser
1               5                   10

<210> SEQ ID NO 33
<211> LENGTH: 32
<212> TYPE: PRT
<213> ORGANISM: Artificial Sequence
<220> FEATURE:
<223> OTHER INFORMATION: Description of Artificial Sequence:human Wnt2
      antigenic peptide sequence #19

<400> SEQUENCE: 33

Ser Ala Phe Val Tyr Ala Ile Ser Ser Ala Gly Val Val Phe Ala Ile
1               5                   10                  15

Thr Arg Ala Cys Ser Gln Gly Glu Val Lys Ser Cys Ser Cys Asp Pro
            20                  25                  30

<210> SEQ ID NO 34
<211> LENGTH: 11
<212> TYPE: PRT
<213> ORGANISM: Artificial Sequence
<220> FEATURE:
<223> OTHER INFORMATION: Description of Artificial Sequence:human Wnt2
      antigenic peptide sequence #20

<400> SEQUENCE: 34

Gly Ile Lys Phe Ala Arg Ala Phe Val Asp Ala
1               5                   10

<210> SEQ ID NO 35
<211> LENGTH: 23
<212> TYPE: PRT
<213> ORGANISM: Artificial Sequence
<220> FEATURE:
<223> OTHER INFORMATION: Description of Artificial Sequence:human Wnt2
      antigenic peptide sequence #21

<400> SEQUENCE: 35

Lys Gln Glu Cys Lys Cys His Gly Val Ser Gly Ser Cys Thr Leu Arg
1               5                   10                  15

Thr Cys Trp Leu Ala Met Ala
            20
```

```
<210> SEQ ID NO 36
<211> LENGTH: 6
<212> TYPE: PRT
<213> ORGANISM: Artificial Sequence
<220> FEATURE:
<223> OTHER INFORMATION: Description of Artificial Sequence:human Wnt2
      antigenic peptide sequence #22

<400> SEQUENCE: 36

Ile Gln Val Val Met Asn
1               5

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence:human Wnt2
      antigenic peptide sequence #23

<400> SEQUENCE: 37

Asn Asp Leu Val Tyr Phe Glu
1               5

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence:human Wnt2
      antigenic peptide sequence #24

<400> SEQUENCE: 38

Pro Asp Tyr Cys Ile Arg Asp
1               5

<210> SEQ ID NO 39
<211> LENGTH: 8
<212> TYPE: PRT
<213> ORGANISM: Artificial Sequence
<220> FEATURE:
<223> OTHER INFORMATION: Description of Artificial Sequence:human Wnt2
      antigenic peptide sequence #25

<400> SEQUENCE: 39

Ala Gly Arg Val Cys Asn Leu Thr
1               5

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence:human Wnt2
      antigenic peptide sequence #26

<400> SEQUENCE: 40

Ser Cys Glu Val Met Cys Cys Gly Arg
1               5

<210> SEQ ID NO 41
<211> LENGTH: 29
<212> TYPE: PRT
<213> ORGANISM: Artificial Sequence
<220> FEATURE:
<223> OTHER INFORMATION: Description of Artificial Sequence:human Wnt2
      antigenic peptide sequence #27

<400> SEQUENCE: 41
```

-continued

Lys Cys Gly Cys Lys Phe His Trp Cys Cys Ala Val Arg Cys Gln Asp
1               5                   10                  15

Cys Leu Glu Ala Leu Asp Val His Thr Cys Lys Ala Pro
            20                  25

<210> SEQ ID NO 42
<211> LENGTH: 23
<212> TYPE: PRT
<213> ORGANISM: Artificial Sequence
<220> FEATURE:
<223> OTHER INFORMATION: Description of Artificial Sequence:human Wnt2
      antigenic peptide sequence #28

<400> SEQUENCE: 42

Ser Arg Val Met Cys Asp Asn Val Pro Gly Leu Val Ser Ser Gln Arg
1               5                   10                  15

Gln Leu Cys His Arg His Pro
            20

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence:human Wnt2
      antigenic peptide sequence #29

<400> SEQUENCE: 43

Ala Glu Cys Gln His Gln Phe
1               5

<210> SEQ ID NO 44
<211> LENGTH: 12
<212> TYPE: PRT
<213> ORGANISM: Artificial Sequence
<220> FEATURE:
<223> OTHER INFORMATION: Description of Artificial Sequence:human Wnt2
      antigenic peptide sequence #30

<400> SEQUENCE: 44

Arg Asp His Ser Leu Phe Gly Arg Val Leu Leu Arg
1               5                   10

<210> SEQ ID NO 45
<211> LENGTH: 32
<212> TYPE: PRT
<213> ORGANISM: Artificial Sequence
<220> FEATURE:
<223> OTHER INFORMATION: Description of Artificial Sequence:human Wnt2
      antigenic peptide sequence #31

<400> SEQUENCE: 45

Glu Ser Ala Phe Val Tyr Ala Ile Ser Ser Ala Gly Val Val Phe Ala
1               5                   10                  15

Ile Thr Arg Ala Cys Ser Gln Gly Glu Val Lys Ser Cys Ser Cys Asp
            20                  25                  30

<210> SEQ ID NO 46
<211> LENGTH: 11
<212> TYPE: PRT
<213> ORGANISM: Artificial Sequence
<220> FEATURE:
<223> OTHER INFORMATION: Description of Artificial Sequence:human Wnt2
      antigenic peptide sequence #32

<400> SEQUENCE: 46

Tyr Gly Ile Lys Phe Ala Arg Ala Phe Val Asp
1               5                   10

```
<210> SEQ ID NO 47
<211> LENGTH: 23
<212> TYPE: PRT
<213> ORGANISM: Artificial Sequence
<220> FEATURE:
<223> OTHER INFORMATION: Description of Artificial Sequence:human Wnt2
      antigenic peptide sequence #33

<400> SEQUENCE: 47

Leu Lys Gln Glu Cys Lys Cys His Gly Val Ser Gly Ser Cys Thr Leu
1               5                   10                  15

Arg Thr Cys Trp Leu Ala Met
            20

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence:human Wnt2
      antigenic peptide sequence #34

<400> SEQUENCE: 48

Gly Ala Ile Gln Val Val Met
1               5

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence:human Wnt2
      antigenic peptide sequence #35

<400> SEQUENCE: 49

Lys Asn Asp Leu Val Tyr Phe
1               5

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence:human Wnt2
      antigenic peptide sequence #36

<400> SEQUENCE: 50

Ser Pro Asp Tyr Cys Ile Arg
1               5

<210> SEQ ID NO 51
<211> LENGTH: 8
<212> TYPE: PRT
<213> ORGANISM: Artificial Sequence
<220> FEATURE:
<223> OTHER INFORMATION: Description of Artificial Sequence:human Wnt2
      antigenic peptide sequence #37

<400> SEQUENCE: 51

Thr Ala Gly Arg Val Cys Asn Leu
1               5

<210> SEQ ID NO 52
<211> LENGTH: 9
<212> TYPE: PRT
<213> ORGANISM: Artificial Sequence
```

```
<220> FEATURE:
<223> OTHER INFORMATION: Description of Artificial Sequence:human Wnt2
      antigenic peptide sequence #38

<400> SEQUENCE: 52

Asp Ser Cys Glu Val Met Cys Cys Gly
1               5

<210> SEQ ID NO 53
<211> LENGTH: 29
<212> TYPE: PRT
<213> ORGANISM: Artificial Sequence
<220> FEATURE:
<223> OTHER INFORMATION: Description of Artificial Sequence:human Wnt2
      antigenic peptide sequence #39

<400> SEQUENCE: 53

Thr Lys Cys Gly Cys Lys Phe His Trp Cys Cys Ala Val Arg Cys Gln
1               5                   10                  15

Asp Cys Leu Glu Ala Leu Asp Val His Thr Cys Lys Ala
            20                  25

<210> SEQ ID NO 54
<211> LENGTH: 111
<212> TYPE: PRT
<213> ORGANISM: Artificial Sequence
<220> FEATURE:
<223> OTHER INFORMATION: Description of Artificial Sequence:anti-Wnt2
      monoclonal antibody 17F7.G7 (subclone A) light
      chain kappa CDR and FR region
<220> FEATURE:
<221> NAME/KEY: MOD_RES
<222> LOCATION: (96)
<223> OTHER INFORMATION: Xaa = Met, Leu or Val

<400> SEQUENCE: 54

Asp Ile Val Leu Thr Gln Ser Pro Ala Ser Leu Ala Val Ser Leu Gly
1               5                   10                  15

Gln Arg Ala Thr Ile Ser Tyr Arg Ala Ser Lys Ser Val Ser Thr Ser
            20                  25                  30

Gly Tyr Ser Tyr Met His Trp Asn Gln Gln Lys Pro Gly Gln Pro Pro
        35                  40                  45

Arg Leu Leu Ile Tyr Leu Val Ser Asn Leu Glu Ser Arg Arg Ser Pro
    50                  55                  60

Ala Arg Phe Ser Gly Gln Trp Cys Leu Val Tyr Arg Leu His Pro Gln
65                  70                  75                  80

Thr Ser Met Pro Val Gly Gly Gly Cys Leu Gln Pro Asp Tyr Xaa
                85                  90                  95

Cys Ser Thr Leu Gly Ser Leu His Val Thr Glu Gly Gly Pro Ser
            100                 105                 110

<210> SEQ ID NO 55
<211> LENGTH: 26
<212> TYPE: PRT
<213> ORGANISM: Artificial Sequence
<220> FEATURE:
<223> OTHER INFORMATION: Description of Artificial Sequence:anti-Wnt2
      monoclonal antibodies 17F7.G7 (subclone A and
      subclone B, chain 1), 8B11.D2, and 8B11.H6 (kappa
      chain 1) light chain kappa FR1 region

<400> SEQUENCE: 55

Asp Ile Val Leu Thr Gln Ser Pro Ala Ser Leu Ala Val Ser Leu Gly
1               5                   10                  15

Gln Arg Ala Thr Ile Ser Tyr Arg Ala Ser
            20                  25
```

```
                         20                  25

<210> SEQ ID NO 56
<211> LENGTH: 10
<212> TYPE: PRT
<213> ORGANISM: Artificial Sequence
<220> FEATURE:
<223> OTHER INFORMATION: Description of Artificial Sequence:anti-Wnt2
      monoclonal antibodies 17F7.G7 (subclone A and
      subclone B, chain 1), 8B11.D2, and 8B11.H6 (kappa
      chain 1) light chain kappa CDR1 region

<400> SEQUENCE: 56

Lys Ser Val Ser Thr Ser Gly Tyr Ser Tyr
1               5                   10

<210> SEQ ID NO 57
<211> LENGTH: 17
<212> TYPE: PRT
<213> ORGANISM: Artificial Sequence
<220> FEATURE:
<223> OTHER INFORMATION: Description of Artificial Sequence:anti-Wnt2
      monoclonal antibodies 17F7.G7 (subclone A and
      subclone B, chain 1), 8B11.D2, and 8B11.H6 (kappa
      chain 1) light chain kappa FR2 region

<400> SEQUENCE: 57

Met His Trp Asn Gln Gln Lys Pro Gly Gln Pro Pro Arg Leu Leu Ile
1               5                   10                  15

Tyr

<210> SEQ ID NO 58
<211> LENGTH: 3
<212> TYPE: PRT
<213> ORGANISM: Artificial Sequence
<220> FEATURE:
<223> OTHER INFORMATION: Description of Artificial Sequence:anti-Wnt2
      monoclonal antibodies 17F7.G7 (subclone A and subclone B, chains 1
      and 2), 8B11.D2, 8B11.H6 (kappa chains 1 and 2) and 17F7.E5
      light chain kappa CDR2 region

<400> SEQUENCE: 58

Leu Val Ser
1

<210> SEQ ID NO 59
<211> LENGTH: 36
<212> TYPE: PRT
<213> ORGANISM: Artificial Sequence
<220> FEATURE:
<223> OTHER INFORMATION: Description of Artificial Sequence:anti-Wnt2
      monoclonal antibody 17F7.G7 (subclone A) light
      chain kappa FR3 region

<400> SEQUENCE: 59

Asn Leu Glu Ser Arg Arg Ser Pro Ala Arg Phe Ser Gly Gln Trp Cys
1               5                   10                  15

Leu Val Tyr Arg Leu His Pro Gln Thr Ser Met Pro Val Gly Gly Gly
                20                  25                  30

Gly Cys Leu Gln
            35

<210> SEQ ID NO 60
<211> LENGTH: 11
<212> TYPE: PRT
<213> ORGANISM: Artificial Sequence
<220> FEATURE:
<223> OTHER INFORMATION: Description of Artificial Sequence:anti-Wnt2
```

```
      monoclonal antibody 17F7.G7 (subclone A) light
      chain kappa CDR3 region
<220> FEATURE:
<221> NAME/KEY: MOD_RES
<222> LOCATION: (4)
<223> OTHER INFORMATION: Xaa = Met, Leu or Val

<400> SEQUENCE: 60

Pro Asp Tyr Xaa Cys Ser Thr Leu Gly Ser Leu
1               5                   10

<210> SEQ ID NO 61
<211> LENGTH: 110
<212> TYPE: PRT
<213> ORGANISM: Artificial Sequence
<220> FEATURE:
<223> OTHER INFORMATION: Description of Artificial Sequence:anti-Wnt2
      monoclonal antibody 17F7.G7 (subclone A) heavy
      chain IgG1 CDR and FR region
<221> NAME/KEY: MOD_RES
<222> LOCATION: (1)..(110)
<223> OTHER INFORMATION: Xaa = any amino acid

<400> SEQUENCE: 61

Gly Pro Glu Leu Val Lys Pro Gly Ala Ser Val Lys Met Ser Cys Lys
1               5                   10                  15

Ala Ser Gly Tyr Thr Phe Thr Asp Tyr Val Leu Ser Trp Val Lys Gln
            20                  25                  30

Arg Thr Gly Gln Gly Leu Glu Trp Ile Gly Glu Ile Tyr Pro Gly Tyr
        35                  40                  45

Gly Ser Thr Tyr Tyr Asn Glu Lys Phe Lys Gly Lys Ala Thr Leu Thr
    50                  55                  60

Ala Asp Lys Ser Ser Asn Thr Ala Tyr Met Gln Leu Ser Ser Leu Thr
65                  70                  75                  80

Ser Glu Asp Ser Ala Val Tyr Phe Cys Ala Arg Trp Gly Asp Cys Phe
                85                  90                  95

Cys Leu Ser Gly Ala Lys Gly Xaa Leu Val Xaa Cys Leu Cys
            100                 105                 110

<210> SEQ ID NO 62
<211> LENGTH: 18
<212> TYPE: PRT
<213> ORGANISM: Artificial Sequence
<220> FEATURE:
<223> OTHER INFORMATION: Description of Artificial Sequence:anti-Wnt2
      monoclonal antibody 17F7.G7 (subclone A) heavy
      chain IgG1 FR1 region

<400> SEQUENCE: 62

Gly Pro Glu Leu Val Lys Pro Gly Ala Ser Val Lys Met Ser Cys Lys
1               5                   10                  15

Ala Ser

<210> SEQ ID NO 63
<211> LENGTH: 8
<212> TYPE: PRT
<213> ORGANISM: Artificial Sequence
<220> FEATURE:
<223> OTHER INFORMATION: Description of Artificial Sequence:anti-Wnt2
      monoclonal antibodies 17F7.G7 (subclones A and B)
      and 17F.E5 heavy chain IgG1 CDR1 region

<400> SEQUENCE: 63

Gly Tyr Thr Phe Thr Asp Tyr Val
1               5
```

```
<210> SEQ ID NO 64
<211> LENGTH: 17
<212> TYPE: PRT
<213> ORGANISM: Artificial Sequence
<220> FEATURE:
<223> OTHER INFORMATION: Description of Artificial Sequence:anti-Wnt2
      monoclonal antibodies 17F7.G7 (subclones A and B)
      and 17F.E5 heavy chain IgG1 FR2 region

<400> SEQUENCE: 64

Leu Ser Trp Val Lys Gln Arg Thr Gly Gln Gly Leu Glu Trp Ile Gly
1               5                   10                  15

Glu

<210> SEQ ID NO 65
<211> LENGTH: 8
<212> TYPE: PRT
<213> ORGANISM: Artificial Sequence
<220> FEATURE:
<223> OTHER INFORMATION: Description of Artificial Sequence:anti-Wnt2
      monoclonal antibodies 17F7.G7 (subclones A and B)
      and 17F.E5 heavy chain IgG1 CDR2 region

<400> SEQUENCE: 65

Ile Tyr Pro Gly Tyr Gly Ser Thr
1               5

<210> SEQ ID NO 66
<211> LENGTH: 38
<212> TYPE: PRT
<213> ORGANISM: Artificial Sequence
<220> FEATURE:
<223> OTHER INFORMATION: Description of Artificial Sequence:anti-Wnt2
      monoclonal antibodies 17F7.G7 (subclones A and B)
      and 17F.E5 heavy chain IgG1 FR3 region

<400> SEQUENCE: 66

Tyr Tyr Asn Glu Lys Phe Lys Gly Lys Ala Thr Leu Thr Ala Asp Lys
1               5                   10                  15

Ser Ser Asn Thr Ala Tyr Met Gln Leu Ser Ser Leu Thr Ser Glu Asp
            20                  25                  30

Ser Ala Val Tyr Phe Cys
        35

<210> SEQ ID NO 67
<211> LENGTH: 11
<212> TYPE: PRT
<213> ORGANISM: Artificial Sequence
<220> FEATURE:
<223> OTHER INFORMATION: Description of Artificial Sequence:anti-Wnt2
      monoclonal antibody 17F7.G7 (subclone A) heavy
      chain IgG1 CDR3 region

<400> SEQUENCE: 67

Ala Arg Trp Gly Asp Cys Phe Cys Leu Ser Gly
1               5                   10

<210> SEQ ID NO 68
<211> LENGTH: 333
<212> TYPE: DNA
<213> ORGANISM: Artificial Sequence
<220> FEATURE:
<223> OTHER INFORMATION: Description of Artificial Sequence:anti-Wnt2
      monoclonal antibody 17F7.G7 (subclone A) light
      chain kappa CDR and FR region
<220> FEATURE:
<221> NAME/KEY: modified_base
<222> LOCATION: (286)
```

```
<223> OTHER INFORMATION: n = g, a, c or t

<400> SEQUENCE: 68
gacattgtgc tgacacagtc tcctgcttcc ttagctgtat ctctggggca gagggccacc      60
atctcataca gggccagcaa aagtgtcagt acatctggct atagttatat gcactggaac     120
caacagaaac caggacagcc acccagactc tcatctatc ttgtatccaa cctagaatct      180
aggaggtcac ctgccaggtt cagtggtcag tggtgtctgg tgtacagact tcaccctcag    240
acatccatgc ctgtcggagg aggaggatgc ctgcaacctg attatntgtg cagcacatta    300
gggagcttac acgttacgga gggggacca agc                                   333

<210> SEQ ID NO 69
<211> LENGTH: 78
<212> TYPE: DNA
<213> ORGANISM: Artificial Sequence
<220> FEATURE:
<223> OTHER INFORMATION: Description of Artificial Sequence:anti-Wnt2
      monoclonal antibodies 17F7.G7 (subclone A and
      subclone B, chain 1), 8B11.D2, and 8B11.H6 (kappa
      chain 1) light chain kappa FR1 region

<400> SEQUENCE: 69
gacattgtgc tgacacagtc tcctgcttcc ttagctgtat ctctggggca gagggccacc      60
atctcataca gggccagc                                                    78

<210> SEQ ID NO 70
<211> LENGTH: 30
<212> TYPE: DNA
<213> ORGANISM: Artificial Sequence
<220> FEATURE:
<223> OTHER INFORMATION: Description of Artificial Sequence:anti-Wnt2
      monoclonal antibodies 17F7.G7 (subclone A and
      subclone B, chain 1), 8B11.D2, and 8B11.H6 (kappa
      chain 1) light chain kappa CDR1 region

<400> SEQUENCE: 70
aaaagtgtca gtacatctgg ctatagttat                                       30

<210> SEQ ID NO 71
<211> LENGTH: 51
<212> TYPE: DNA
<213> ORGANISM: Artificial Sequence
<220> FEATURE:
<223> OTHER INFORMATION: Description of Artificial Sequence:anti-Wnt2
      monoclonal antibody 17F7.G7 (subclone A) light
      chain kappa CDR and FR region

<400> SEQUENCE: 71
atgcactgga accaacagaa accaggacag ccacccagac tcctcatcta t                51

<210> SEQ ID NO 72
<211> LENGTH: 9
<212> TYPE: DNA
<213> ORGANISM: Artificial Sequence
<220> FEATURE:
<223> OTHER INFORMATION: Description of Artificial Sequence:anti-Wnt2
      monoclonal antibodies 17F7.G7 (subclone A and subclone B, chains 1
      and 2), 8B11.D2, 8B11.H6 (kappa chains 1 and 2) and 17F7.E5
      light chain kappa CDR2 region

<400> SEQUENCE: 72 cttgtatcc                                                               9

<210> SEQ ID NO 73
<211> LENGTH: 108
```

```
<212> TYPE: DNA
<213> ORGANISM: Artificial Sequence
<220> FEATURE:
<223> OTHER INFORMATION: Description of Artificial Sequence:anti-Wnt2
      monoclonal antibody 17F7.G7 (subclone A) light
      chain kappa CDR and FR region

<400> SEQUENCE: 73
aacctagaat ctaggaggtc acctgccagg ttcagtggtc agtggtgtct ggtgtacaga    60
cttcaccctc agacatccat gcctgtcgga ggaggaggat gcctgcaa               108

<210> SEQ ID NO 74
<211> LENGTH: 33
<212> TYPE: DNA
<213> ORGANISM: Artificial Sequence
<220> FEATURE:
<223> OTHER INFORMATION: Description of Artificial Sequence:anti-Wnt2
      monoclonal antibody 17F7.G7 (subclone A) light
      chain kappa CDR and FR region
<220> FEATURE:
<221> NAME/KEY: modified_base
<222> LOCATION: (10)
<223> OTHER INFORMATION: n = g, a, c or t

<400> SEQUENCE: 74
cctgattatn tgtgcagcac attagggagc tta                                33

<210> SEQ ID NO 75
<211> LENGTH: 297
<212> TYPE: DNA
<213> ORGANISM: Artificial Sequence
<220> FEATURE:
<223> OTHER INFORMATION: Description of Artificial Sequence:anti-Wnt2
      monoclonal antibody 17F7.G7 (subclone A) heavy
      chain IgG1 CDR and FR region
<220> FEATURE:
<221> NAME/KEY: modified_base
<222> LOCATION: (5)
<223> OTHER INFORMATION: n = g, a, c or t

<400> SEQUENCE: 75
agtcnggacc tgagctggtg aagcctgggg cttcagtgaa gatgtcctgc aaggcttctg    60
gatacacatt cactgactat gttttaagct gggtgaagca gagaactgga cagggccttg   120
agtggattgg agagatttat cctggatatg gtagtactta ctacaatgag aagttcaagg   180
gcaaggccac actgactgct gacaaatcct ccaacacagc ctacatgcag ctcagcagcc   240
tgacatctga ggactctgcg gtctatttct gtgcaagatg gggggattgc ttttgct      297

<210> SEQ ID NO 76
<211> LENGTH: 59
<212> TYPE: DNA
<213> ORGANISM: Artificial Sequence
<220> FEATURE:
<223> OTHER INFORMATION: Description of Artificial Sequence:anti-Wnt2
      monoclonal antibody 17F7.G7 (subclone A) heavy
      chain IgG1 FR1 region
<220> FEATURE:
<221> NAME/KEY: modified_base
<222> LOCATION: (5)
<223> OTHER INFORMATION: n = g, a, c or t

<400> SEQUENCE: 76
agtcnggacc tgagctggtg aagcctgggg cttcagtgaa gatgtcctgc aaggcttct     59

<210> SEQ ID NO 77
<211> LENGTH: 24
<212> TYPE: DNA
<213> ORGANISM: Artificial Sequence
```

```
<220> FEATURE:
<223> OTHER INFORMATION: Description of Artificial Sequence:anti-Wnt2
      monoclonal antibodies 17F7.G7 (subclones A and B)
      and 17F7.E5 heavy chain IgG1 CDR1 region

<400> SEQUENCE: 77
ggatacacat tcactgacta tgtt                                          24

<210> SEQ ID NO 78
<211> LENGTH: 51
<212> TYPE: DNA
<213> ORGANISM: Artificial Sequence
<220> FEATURE:
<223> OTHER INFORMATION: Description of Artificial Sequence:anti-Wnt2
      monoclonal antibody 17F7.G7 (subclones A and B)
      and 17F7.E5 heavy chain IgG1 FR2 region

<400> SEQUENCE: 78
ttaagctggg tgaagcagag aactggacag ggccttgagt ggattggaga g            51

<210> SEQ ID NO 79
<211> LENGTH: 24
<212> TYPE: DNA
<213> ORGANISM: Artificial Sequence
<220> FEATURE:
<223> OTHER INFORMATION: Description of Artificial Sequence:anti-Wnt2
      monoclonal antibody 17F7.G7 (subclones A and B)
      and 17F7.E5 heavy chain IgG1 CDR2 region

<400> SEQUENCE: 79
atttatcctg gatatggtag tact                                          24

<210> SEQ ID NO 80
<211> LENGTH: 114
<212> TYPE: DNA
<213> ORGANISM: Artificial Sequence
<220> FEATURE:
<223> OTHER INFORMATION: Description of Artificial Sequence:anti-Wnt2
      monoclonal antibody 17F7.G7 (subclones A and B)
      and 17F7.E5 heavy chain IgG1 FR3 region

<400> SEQUENCE: 80
tactacaatg agaagttcaa gggcaaggcc acactgactg ctgacaaatc ctccaacaca   60
gcctacatgc agctcagcag cctgacatct gaggactctg cggtctattt ctgt        114

<210> SEQ ID NO 81
<211> LENGTH: 25
<212> TYPE: DNA
<213> ORGANISM: Artificial Sequence
<220> FEATURE:
<223> OTHER INFORMATION: Description of Artificial Sequence:anti-Wnt2
      monoclonal antibody 17F7.G7 (subclone A) heavy
      chain IgG1 CDR3 region

<400> SEQUENCE: 81
gcaagatggg gggattgctt ttgct                                         25

<210> SEQ ID NO 82
<211> LENGTH: 108
<212> TYPE: PRT
<213> ORGANISM: Artificial Sequence
<220> FEATURE:
<223> OTHER INFORMATION: Description of Artificial Sequence:anti-Wnt2
      monoclonal antibodies 17F7.G7 (subclone B, chain
      1) and 8B11.D2 light chain kappa CDR and FR region

<400> SEQUENCE: 82

Asp Ile Val Leu Thr Gln Ser Pro Ala Ser Leu Ala Val Ser Leu Gly
```

```
                   1               5                  10                 15
Gln Arg Ala Thr Ile Ser Tyr Arg Ala Ser Lys Ser Val Ser Thr Ser
                20                  25                 30

Gly Tyr Ser Tyr Met His Trp Asn Gln Gln Lys Pro Gly Gln Pro Pro
            35                  40                 45

Arg Leu Leu Ile Tyr Leu Val Ser Asn Leu Glu Ser Gly Val Pro Ala
        50                  55                 60

Arg Phe Ser Gly Ser Gly Ser Gly Thr Asp Phe Thr Leu Asn Ile His
65                  70                  75                 80

Pro Val Glu Glu Glu Asp Ala Ala Thr Tyr Tyr Cys Gln His Ile Arg
                85                  90                 95

Glu Leu Thr Arg Ser Glu Gly Gly Pro Ser Trp Lys
            100                 105

<210> SEQ ID NO 83
<211> LENGTH: 36
<212> TYPE: PRT
<213> ORGANISM: Artificial Sequence
<220> FEATURE:
<223> OTHER INFORMATION: Description of Artificial Sequence:anti-Wnt2
      monoclonal antibodies 17F7.G7 (subclone B, chain
      1) and 8B11.D2 light chain kappa FR3 region

<400> SEQUENCE: 83

Asn Leu Glu Ser Gly Val Pro Ala Arg Phe Ser Gly Ser Gly Ser Gly
1               5                   10                  15

Thr Asp Phe Thr Leu Asn Ile His Pro Val Glu Glu Glu Asp Ala Ala
            20                  25                  30

Thr Tyr Tyr Cys
        35

<210> SEQ ID NO 84
<211> LENGTH: 8
<212> TYPE: PRT
<213> ORGANISM: Artificial Sequence
<220> FEATURE:
<223> OTHER INFORMATION: Description of Artificial Sequence:anti-Wnt2
      monoclonal antibodies 17F7.G7 (subclone B, chain
      1), 8B11.H6 (kappa chain 1) and 8B11.D2 light
      chain kappa CDR3 region

<400> SEQUENCE: 84

Gln His Ile Arg Glu Leu Thr Arg
1               5

<210> SEQ ID NO 85
<211> LENGTH: 131
<212> TYPE: PRT
<213> ORGANISM: Artificial Sequence
<220> FEATURE:
<223> OTHER INFORMATION: Description of Artificial Sequence:anti-Wnt2
      monoclonal antibody 8B11.D2 heavy chain IgG1 CDR
      and FR region

<400> SEQUENCE: 85

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Thr Tyr
            20                  25                  30

Val Met His Trp Val Lys Gln Lys Pro Gly Gln Gly Leu Glu Trp Ile
        35                  40                  45

Gly Tyr Ile Asp Pro Tyr Asn Asp Gly Thr Lys Tyr Asn Glu Lys Phe
    50                  55                  60
```

```
Lys Gly Lys Ala Thr Leu Thr Ser Asp Lys Ser Ser Ser Thr Ala Tyr
 65                  70                  75                  80

Met Glu Leu Ser Ser Leu Thr Ser Glu Asp Ser Ala Val Tyr Tyr Cys
                 85                  90                  95

Thr Arg Gly Asn Gly Asn Tyr Glu Ser Tyr Tyr Ala Met Asp Tyr Trp
            100                 105                 110

Gly Gln Gly Thr Ser Val Thr Val Ser Ser Ala Lys Thr Thr Pro Pro
        115                 120                 125

Ser Val Tyr
    130

<210> SEQ ID NO 86
<211> LENGTH: 25
<212> TYPE: PRT
<213> ORGANISM: Artificial Sequence
<220> FEATURE:
<223> OTHER INFORMATION: Description of Artificial Sequence:anti-Wnt2
      monoclonal antibody 8B11.D2 heavy chain IgG1 FR1
      region

<400> SEQUENCE: 86

Glu Val Gln Leu Gln Gln Ser Gly Pro Glu Leu Val Lys Pro Gly Ala
1               5                   10                  15

Ser Val Lys Met Ser Cys Lys Ala Ser
            20                  25

<210> SEQ ID NO 87
<211> LENGTH: 8
<212> TYPE: PRT
<213> ORGANISM: Artificial Sequence
<220> FEATURE:
<223> OTHER INFORMATION: Description of Artificial Sequence:anti-Wnt2
      monoclonal antibodies 8B11.D2 and 8B11.H6 heavy
      chain IgG1 CDR1 region

<400> SEQUENCE: 87

Gly Tyr Thr Phe Thr Thr Tyr Val
1               5

<210> SEQ ID NO 88
<211> LENGTH: 17
<212> TYPE: PRT
<213> ORGANISM: Artificial Sequence
<220> FEATURE:
<223> OTHER INFORMATION: Description of Artificial Sequence:anti-Wnt2
      monoclonal antibodies 8B11.D2 and 8B11.H6 heavy
      chain IgG1 FR2 region

<400> SEQUENCE: 88

Met His Trp Val Lys Gln Lys Pro Gly Gln Gly Leu Glu Trp Ile Gly
1               5                   10                  15

Tyr

<210> SEQ ID NO 89
<211> LENGTH: 8
<212> TYPE: PRT
<213> ORGANISM: Artificial Sequence
<220> FEATURE:
<223> OTHER INFORMATION: Description of Artificial Sequence:anti-Wnt2
      monoclonal antibodies 8B11.D2 and 8B11.H6 heavy
      chain IgG1 CDR2 region

<400> SEQUENCE: 89

Ile Asp Pro Tyr Asn Asp Gly Thr
1               5
```

<210> SEQ ID NO 90
<211> LENGTH: 38
<212> TYPE: PRT
<213> ORGANISM: Artificial Sequence
<220> FEATURE:
<223> OTHER INFORMATION: Description of Artificial Sequence:anti-Wnt2
monoclonal antibodies 8B11.D2 and 8B11.H6 heavy
chain IgG1 FR3 region

<400> SEQUENCE: 90

```
Lys Tyr Asn Glu Lys Phe Lys Gly Lys Ala Thr Leu Thr Ser Asp Lys
1               5                   10                  15

Ser Ser Ser Thr Ala Tyr Met Glu Leu Ser Ser Leu Thr Ser Glu Asp
            20                  25                  30

Ser Ala Val Tyr Tyr Cys
        35
```

<210> SEQ ID NO 91
<211> LENGTH: 15
<212> TYPE: PRT
<213> ORGANISM: Artificial Sequence
<220> FEATURE:
<223> OTHER INFORMATION: Description of Artificial Sequence:anti-Wnt2
monoclonal antibodies 8B11.D2 and 8B11.H6 heavy
chain IgG1 CDR3 region

<400> SEQUENCE: 91

```
Thr Arg Gly Asn Gly Asn Tyr Glu Ser Tyr Tyr Ala Met Asp Tyr
1               5                   10                  15
```

<210> SEQ ID NO 92
<211> LENGTH: 324
<212> TYPE: DNA
<213> ORGANISM: Artificial Sequence
<220> FEATURE:
<223> OTHER INFORMATION: Description of Artificial Sequence:anti-Wnt2
monoclonal antibodies 17F7.G7 (subclone B, chain
1), 8B11.D2 and 8B11.H6 (kappa chain 1) light
chain kappa CDR and FR region

<400> SEQUENCE: 92

```
gacattgtgc tgacacagtc tcctgcttcc ttagctgtat ctctggggca gagggccacc    60
atctcataca gggccagcaa aagtgtcagt acatctggct atagttatat gcactggaac   120
caacagaaac caggacagcc acccagactc ctcatctatc ttgtatccaa cctagaatct   180
ggggtccctg ccaggttcag tggcagtggg tctgggacag acttcaccct caacatccat   240
cctgtggagg aggaggatgc tgcaacctat tactgtcagc acattaggga gcttacacgt   300
tcggaggggg gaccaagctg gaaa                                          324
```

<210> SEQ ID NO 93
<211> LENGTH: 108
<212> TYPE: DNA
<213> ORGANISM: Artificial Sequence
<220> FEATURE:
<223> OTHER INFORMATION: Description of Artificial Sequence:anti-Wnt2
monoclonal antibodies 17F7.G7 (subclone B, chain
1), 8B11.D2 and 8B11.H6 (kappa chain 1) light
chain kappa FR3 region

<400> SEQUENCE: 93

```
aacctagaat ctgggggtccc tgccaggttc agtggcagtg ggtctgggac agacttcacc    60
ctcaacatcc atcctgtgga ggaggaggat gctgcaacct attactgt              108
```

<210> SEQ ID NO 94
<211> LENGTH: 24
<212> TYPE: DNA
<213> ORGANISM: Artificial Sequence
<220> FEATURE:
<223> OTHER INFORMATION: Description of Artificial Sequence:anti-Wnt2
monoclonal antibodies 17F7.G7 (subclone B, chain
1), 8B11.D2 and 8B11.H6 (kappa chain 1) light
chain kappa CDR3 region

<400> SEQUENCE: 94
cagcacatta gggagcttac acgt                                           24

<210> SEQ ID NO 95
<211> LENGTH: 394
<212> TYPE: DNA
<213> ORGANISM: Artificial Sequence
<220> FEATURE:
<223> OTHER INFORMATION: Description of Artificial Sequence:anti-Wnt2
monoclonal antibody 8B11.D2 heavy chain IgG1 CDR
and FR region

<400> SEQUENCE: 95
gaggtccagc tgcagcagtc tggacctgag ctggtgaagc ctggggcttc tgtgaagatg     60
tcctgcaagg cttctggata cacattcact acctatgtta tgcactgggt gaaacagaag    120
cctgggcagg gccttgagtg gattggatac attgatcctt acaatgatgg tactaagtac    180
aatgagaagt tcaaaggcaa ggccacactg acttcagaca atcctccag cacagcctac     240 atggagctca gcagcctgac ctctgaggac tctgcggtct attactgtac aagagggaat    300
ggtaactacg agagttacta tgctatggac tactgggggtc aaggaacctc agtcaccgtc   360
tcctcagcca aaacgacacc cccatctgtc tata                                394

<210> SEQ ID NO 96
<211> LENGTH: 75
<212> TYPE: DNA
<213> ORGANISM: Artificial Sequence
<220> FEATURE:
<223> OTHER INFORMATION: Description of Artificial Sequence:anti-Wnt2
monoclonal antibody 8B11.D2 heavy chain IgG1 FR1
region

<400> SEQUENCE: 96
gaggtccagc tgcagcagtc tggacctgag ctggtgaagc ctggggcttc tgtgaagatg     60
tcctgcaagg cttct                                                     75

<210> SEQ ID NO 97
<211> LENGTH: 24
<212> TYPE: DNA
<213> ORGANISM: Artificial Sequence
<220> FEATURE:
<223> OTHER INFORMATION: Description of Artificial Sequence:anti-Wnt2
monoclonal antibodies 8B11.D2 and 8B11.H6 heavy
chain IgG1 CDR1 region

<400> SEQUENCE: 97
ggatacacat tcactaccta tgtt                                           24

<210> SEQ ID NO 98
<211> LENGTH: 51
<212> TYPE: DNA
<213> ORGANISM: Artificial Sequence
<220> FEATURE:
<223> OTHER INFORMATION: Description of Artificial Sequence:anti-Wnt2
monoclonal antibodies 8B11.D2 and 8B11.H6 heavy
chain IgG1 FR2 region

```
<400> SEQUENCE: 98
atgcactggg tgaaacagaa gcctgggcag ggccttgagt ggattggata c          51

<210> SEQ ID NO 99
<211> LENGTH: 24
<212> TYPE: DNA
<213> ORGANISM: Artificial Sequence
<220> FEATURE:
<223> OTHER INFORMATION: Description of Artificial Sequence:anti-Wnt2
      monoclonal antibodies 8B11.D2 and 8B11.H6 heavy
      chain IgG1 CDR2 region

<400> SEQUENCE: 99
attgatcctt acaatgatgg tact                                        24

<210> SEQ ID NO 100
<211> LENGTH: 114
<212> TYPE: DNA
<213> ORGANISM: Artificial Sequence
<220> FEATURE:
<223> OTHER INFORMATION: Description of Artificial Sequence:anti-Wnt2
      monoclonal antibodies 8B11.D2 and 8B11.H6 heavy
      chain IgG1 FR3 region

<400> SEQUENCE: 100
aagtacaatg agaagttcaa aggcaaggcc acactgactt cagacaaatc ctccagcaca  60
gcctacatgg agctcagcag cctgacctct gaggactctg cggtctatta ctgt       114

<210> SEQ ID NO 101
<211> LENGTH: 45
<212> TYPE: DNA
<213> ORGANISM: Artificial Sequence
<220> FEATURE:
<223> OTHER INFORMATION: Description of Artificial Sequence:anti-Wnt2
      monoclonal antibodies 8B11.D2 and 8B11.H6 heavy
      chain IgG1 CDR3 region

<400> SEQUENCE: 101
acaagaggga atggtaacta cgagagttac tatgctatgg actac                 45

<210> SEQ ID NO 102
<211> LENGTH: 112
<212> TYPE: PRT
<213> ORGANISM: Artificial Sequence
<220> FEATURE:
<223> OTHER INFORMATION: Description of Artificial Sequence:anti-Wnt2
      monoclonal antibody 17F7.E5 light chain kappa CDR
      and FR region

<400> SEQUENCE: 102

Asp Ile Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Trp Thr Leu Arg Trp Arg His Gln Ala Glu Ser Ile
            100                 105                 110
```

<210> SEQ ID NO 103
<211> LENGTH: 26
<212> TYPE: PRT
<213> ORGANISM: Artificial Sequence
<220> FEATURE:
<223> OTHER INFORMATION: Description of Artificial Sequence:anti-Wnt2
monoclonal antibodies 17F7.G7 (subclone B, chain
2) and 17F7.E5 light chain kappa FR1 region

<400> SEQUENCE: 103

Asp Ile Val Met Thr Gln Thr Pro Leu Thr Leu Ser Val Thr Ile Gly
1               5                   10                  15

Gln Pro Ala Ser Ile Ser Cys Lys Ser Ser
            20                  25

<210> SEQ ID NO 104
<211> LENGTH: 11
<212> TYPE: PRT
<213> ORGANISM: Artificial Sequence
<220> FEATURE:
<223> OTHER INFORMATION: Description of Artificial Sequence:anti-Wnt2
monoclonal antibodies 17F7.G7 (subclone B, chain
2) and 17F7.E5 light chain kappa CDR1 region

<400> SEQUENCE: 104

Gln Ser Leu Leu Asp Ser Asp Gly Lys Thr Tyr
1               5                   10

<210> SEQ ID NO 105
<211> LENGTH: 17
<212> TYPE: PRT
<213> ORGANISM: Artificial Sequence
<220> FEATURE:
<223> OTHER INFORMATION: Description of Artificial Sequence:anti-Wnt2
monoclonal antibodies 17F7.G7 (subclone B, chain
2), 17F7.E5 and 8B11.H6 (kappa chain 2) light
chain kappa FR2 region

<400> SEQUENCE: 105

Leu Asn Trp Leu Leu Gln Arg Pro Gly Gln Ser Pro Lys Arg Leu Ile
1               5                   10                  15

Tyr

<210> SEQ ID NO 106
<211> LENGTH: 36
<212> TYPE: PRT
<213> ORGANISM: Artificial Sequence
<220> FEATURE:
<223> OTHER INFORMATION: Description of Artificial Sequence:anti-Wnt2
monoclonal antibodies 17F7.G7 (subclone B, chain
2), 17F7.E5 and 8B11.H6 (kappa chain 2) light
chain kappa FR3 region

<400> SEQUENCE: 106

Lys Leu Asp Ser Gly Val Pro Asp Arg Phe Thr Gly Ser Gly Ser Gly
1               5                   10                  15

Thr Asp Phe Thr Leu Lys Ile Ser Arg Val Glu Ala Glu Asp Leu Gly
            20                  25                  30

Val Tyr Tyr Cys
        35

<210> SEQ ID NO 107
<211> LENGTH: 11
<212> TYPE: PRT
<213> ORGANISM: Artificial Sequence
<220> FEATURE:

```
<223> OTHER INFORMATION: Description of Artificial Sequence:anti-Wnt2
      monoclonal antibody 17F7.E5 light chain kappa CDR3
      region

<400> SEQUENCE: 107

Trp Gln Gly Thr His Phe Pro Trp Thr Leu Arg
1               5                   10

<210> SEQ ID NO 108
<211> LENGTH: 124
<212> TYPE: PRT
<213> ORGANISM: Artificial Sequence
<220> FEATURE:
<223> OTHER INFORMATION: Description of Artificial Sequence:anti-Wnt2
      monoclonal antibody 17F7.E5 heavy chain IgG1 CDR
      and FR region

<400> SEQUENCE: 108

Gln Val Gln Leu Gln Gln Ser Gly Ala Glu Leu Gly Thr Trp Gly Phe
1               5                   10                  15

Ser Glu Asp Val Leu Gln Ala Ser Gly Tyr Thr Phe Thr Asp Tyr Val
                20                  25                  30

Leu Ser Trp Val Lys Gln Arg Thr Gly Gln Gly Leu Glu Trp Ile Gly
        35                  40                  45

Glu Ile Tyr Pro Gly Tyr Gly Ser Thr Tyr Tyr Asn Glu Lys Phe Lys
    50                  55                  60

Gly Lys Ala Thr Leu Thr Ala Asp Lys Ser Ser Asn Thr Ala Tyr Met
65                  70                  75                  80

Gln Leu Ser Ser Leu Thr Ser Glu Asp Ser Ala Val Tyr Phe Cys Ala
                85                  90                  95

Arg Trp Gly Asp Ser Phe Ala Tyr Trp Gly Gln Gly Thr Leu Val Thr
            100                 105                 110

Val Ser Ala Ala Lys Thr Thr Pro Pro Ser Val Tyr
        115                 120

<210> SEQ ID NO 109
<211> LENGTH: 24
<212> TYPE: PRT
<213> ORGANISM: Artificial Sequence
<220> FEATURE:
<223> OTHER INFORMATION: Description of Artificial Sequence:anti-Wnt2
      monoclonal antibody 17F7.E5 heavy chain IgG1 FR1
      region

<400> SEQUENCE: 109

Gln Val Gln Leu Gln Gln Ser Gly Ala Glu Leu Gly Thr Trp Gly Phe
1               5                   10                  15

Ser Glu Asp Val Leu Gln Ala Ser
                20

<210> SEQ ID NO 110
<211> LENGTH: 9
<212> TYPE: PRT
<213> ORGANISM: Artificial Sequence
<220> FEATURE:
<223> OTHER INFORMATION: Description of Artificial Sequence:anti-Wnt2
      monoclonal antibodies 17F7.E5 and 17F7.G7
      (subclone B and subclone A resequenced) heavy
      chain IgG1 CDR3 region

<400> SEQUENCE: 110

Ala Arg Trp Gly Asp Ser Phe Ala Tyr
1               5
```

```
<210> SEQ ID NO 111
<211> LENGTH: 337
<212> TYPE: DNA
<213> ORGANISM: Artificial Sequence
<220> FEATURE:
<223> OTHER INFORMATION: Description of Artificial Sequence:anti-Wnt2
      monoclonal antibody 17F7.E5 light chain kappa CDR
      and FR region

<400> SEQUENCE: 111
gacattgtga tgacacagac tccactcact tgtcggtta ccattggaca accagcctcc      60
atctcttgca agtcaagtca gagcctctta gatagtgatg aaagacata tttgaattgg     120 ctgttacaga ggccaggcca gtctccaaag cgcctaatct atctggtgtc taaactggac    180
tctggagtcc ctgacaggtt cactggcagt ggatcaggga cagatttcac actgaaaatc    240
agcagagtgg aggctgagga tttgggagtt tattattgct ggcaaggtac acattttccg    300
tggacgttgc ggtggaggca ccaagctgaa tcaatcg                             337

<210> SEQ ID NO 112
<211> LENGTH: 78
<212> TYPE: DNA
<213> ORGANISM: Artificial Sequence
<220> FEATURE:
<223> OTHER INFORMATION: Description of Artificial Sequence:anti-Wnt2
      monoclonal antibodies 17F7.E5 and 17F7.G7
      (subclone B, chain 2) light chain kappa FR1 region

<400> SEQUENCE: 112
gacattgtga tgacacagac tccactcact tgtcggtta ccattggaca accagcctcc      60
atctcttgca agtcaagt                                                   78

<210> SEQ ID NO 113
<211> LENGTH: 33
<212> TYPE: DNA
<213> ORGANISM: Artificial Sequence
<220> FEATURE:
<223> OTHER INFORMATION: Description of Artificial Sequence:anti-Wnt2
      monoclonal antibodies 17F7.E5 and 17F7.G7
      (subclone B, chain 2) light chain kappa CDR1
      region

<400> SEQUENCE: 113
cagagcctct tagatagtga tggaaagaca tat                                  33

<210> SEQ ID NO 114
<211> LENGTH: 51
<212> TYPE: DNA
<213> ORGANISM: Artificial Sequence
<220> FEATURE:
<223> OTHER INFORMATION: Description of Artificial Sequence:anti-Wnt2
      monoclonal antibody 17F7.E5 light chain kappa FR2
      region

<400> SEQUENCE: 114
ttgaattggc tgttacagag gccaggccag tctccaaagc gcctaatcta t              51

<210> SEQ ID NO 115
<211> LENGTH: 9
<212> TYPE: DNA
<213> ORGANISM: Artificial Sequence
<220> FEATURE:
<223> OTHER INFORMATION: Description of Artificial Sequence:anti-Wnt2
      monoclonal antibodies 17F7.E5, 8B11.H6 (kappa
      chain 2) and 17F7.G7 (subclone B, chain 2) light
      chain kappa CDR2 region

<400> SEQUENCE: 115
``` ctggtgtct 9

<210> SEQ ID NO 116
<211> LENGTH: 108
<212> TYPE: DNA
<213> ORGANISM: Artificial Sequence
<220> FEATURE:
<223> OTHER INFORMATION: Description of Artificial Sequence:anti-Wnt2
monoclonal antibodies 17F7.E5 and 17F7.G7
(subclone B, chain 2) light chain kappa FR3 region

<400> SEQUENCE: 116
aaactggact ctggagtccc tgacaggttc actggcagtg gatcagggac agatttcaca    60
ctgaaaatca gcagagtgga ggctgaggat ttgggagttt attattgc                108

<210> SEQ ID NO 117
<211> LENGTH: 33
<212> TYPE: DNA
<213> ORGANISM: Artificial Sequence
<220> FEATURE:
<223> OTHER INFORMATION: Description of Artificial Sequence:anti-Wnt2
monoclonal antibody 17F7.E5 light chain kappa CDR3
region

<400> SEQUENCE: 117
tggcaaggta cacattttcc gtggacgttg cgg                                  33

<210> SEQ ID NO 118
<211> LENGTH: 376
<212> TYPE: DNA
<213> ORGANISM: Artificial Sequence
<220> FEATURE:
<223> OTHER INFORMATION: Description of Artificial Sequence:anti-Wnt2
monoclonal antibody 17F7.E5 heavy chain IgG1 CDR
and FR region
<220> FEATURE:
<221> NAME/KEY: modified_base
<222> LOCATION: (374)
<223> OTHER INFORMATION: n = g, a, c or t

<400> SEQUENCE: 118
caggtccagc tgcagcagtc tggagctgag ctgggaacct ggggcttcag tgaagatgtc    60
ctgcaggctt ctggatacac attcactgac tatgttttaa gctgggtgaa gcagagaact   120
ggacagggcc ttgagtggat tggagagatt tatcctggat atggtagtac ttactacaat   180
gagaagttca agggcaaggc cacactgact gctgacaaat cctccaacac agcctacatg   240
cagctcagca gcctgacatc tgaggactct gcggtctatt tctgtgcaag atgggggggat   300 tcttttgctt actggggcca agggactctg gtcactgtct ctgcagccaa aacgacaccc   360
ccatctgtct atanaa                                                    376

<210> SEQ ID NO 119
<211> LENGTH: 72
<212> TYPE: DNA
<213> ORGANISM: Artificial Sequence
<220> FEATURE:
<223> OTHER INFORMATION: Description of Artificial Sequence:anti-Wnt2
monoclonal antibody 17F7.E5 heavy chain IgG1 FR1
region

<400> SEQUENCE: 119
caggtccagc tgcagcagtc tggagctgag ctgggaacct ggggcttcag tgaagatgtc    60
ctgcaggctt ct                                                         72

```
<210> SEQ ID NO 120
<211> LENGTH: 27
<212> TYPE: DNA
<213> ORGANISM: Artificial Sequence
<220> FEATURE:
<223> OTHER INFORMATION: Description of Artificial Sequence:anti-Wnt2
      monoclonal antibodies 17F7.E5 and 17F7.G7
      (subclone B) heavy chain IgG1 CDR3 region

<400> SEQUENCE: 120
gcaagatggg gggattctttt tgcttac                                            27

<210> SEQ ID NO 121
<211> LENGTH: 108
<212> TYPE: PRT
<213> ORGANISM: Artificial Sequence
<220> FEATURE:
<223> OTHER INFORMATION: Description of Artificial Sequence:anti-Wnt2
      monoclonal antibody 8B11.H6 light chain kappa
      (kappa chain 1) CDR and FR region

<400> SEQUENCE: 121

Asp Ile Val Leu Thr Gln Ser Pro Ala Ser Leu Ala Val Ser Leu Gly
1               5                   10                  15

Gln Arg Ala Thr Ile Ser Tyr Arg Ala Ser Lys Ser Val Ser Thr Ser
            20                  25                  30

Gly Tyr Ser Tyr Met His Trp Asn Gln Gln Lys Pro Gly Gln Pro Pro
        35                  40                  45

Arg Leu Leu Ile Tyr Leu Val Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ile Arg
                85                  90                  95

Glu Leu Thr Arg Ser Glu Gly Gly Pro Ser Trp Lys
            100                 105

<210> SEQ ID NO 122
<211> LENGTH: 36
<212> TYPE: PRT
<213> ORGANISM: Artificial Sequence
<220> FEATURE:
<223> OTHER INFORMATION: Description of Artificial Sequence:anti-Wnt2
      monoclonal antibody 8B11.H6 light chain kappa
      (kappa chain 1) FR3 region

<400> SEQUENCE: 122

Asn Leu Glu Ser Gly Val Pro Ala Arg Phe Ser Gly Ser Gly Ser Gly
1               5                   10                  15

Thr Asp Phe Thr Leu Asn Ile His Pro Val Glu Glu Glu Asp Ala Ala
            20                  25                  30

Thr Tyr Tyr Cys
        35

<210> SEQ ID NO 123
<211> LENGTH: 113
<212> TYPE: PRT
<213> ORGANISM: Artificial Sequence
<220> FEATURE:
<223> OTHER INFORMATION: Description of Artificial Sequence:anti-Wnt2
      monoclonal antibody 8B11.H6 light chain kappa
      (kappa chain 2) CDR and FR region

<400> SEQUENCE: 123

Asp Ile Val Met Thr Gln Thr Pro Leu Thr Leu Ser Val Thr Ile Gly
```

-continued

```
                1               5                  10                  15
Gln Pro Ala Ser Phe Ser Cys Lys Ser Ser Gln Arg Leu Leu Tyr Ser
                20                  25                  30

Asn Gly Lys Thr Tyr Leu Asn Trp Leu Leu Gln Arg Pro Gly Gln Ser
            35                  40                  45

Pro Lys Arg Leu Ile Tyr Leu Val Ser Lys Leu Asp Ser Gly Val Pro
        50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Val Gln Gly
                85                  90                  95

Thr His Phe Pro Trp Thr Leu Arg Trp Arg His Gln Ala Glu Ile Asn
                100                 105                 110

Arg
```

<210> SEQ ID NO 124
<211> LENGTH: 26
<212> TYPE: PRT
<213> ORGANISM: Artificial Sequence
<220> FEATURE:
<223> OTHER INFORMATION: Description of Artificial Sequence:anti-Wnt2
      monoclonal antibody 8B11.H6 light chain kappa
      (kappa chain 2) FR1 region

<400> SEQUENCE: 124

```
Asp Ile Val Met Thr Gln Thr Pro Leu Thr Leu Ser Val Thr Ile Gly
1               5                  10                  15

Gln Pro Ala Ser Phe Ser Cys Lys Ser Ser
            20                  25
```

<210> SEQ ID NO 125
<211> LENGTH: 11
<212> TYPE: PRT
<213> ORGANISM: Artificial Sequence
<220> FEATURE:
<223> OTHER INFORMATION: Description of Artificial Sequence:anti-Wnt2
      monoclonal antibody 8B11.H6 light chain kappa
      (kappa chain 2) CDR1 region

<400> SEQUENCE: 125

```
Gln Arg Leu Leu Tyr Ser Asn Gly Lys Thr Tyr
1               5                  10
```

<210> SEQ ID NO 126
<211> LENGTH: 11
<212> TYPE: PRT
<213> ORGANISM: Artificial Sequence
<220> FEATURE:
<223> OTHER INFORMATION: Description of Artificial Sequence:anti-Wnt2
      monoclonal antibody 8B11.H6 light chain kappa
      (kappa chain 2) CDR3 region

<400> SEQUENCE: 126

```
Val Gln Gly Thr His Phe Pro Trp Thr Leu Arg
1               5                  10
```

<210> SEQ ID NO 127
<211> LENGTH: 123
<212> TYPE: PRT
<213> ORGANISM: Artificial Sequence
<220> FEATURE:
<223> OTHER INFORMATION: Description of Artificial Sequence:anti-Wnt2
      monoclonal antibody 8B11.H6 heavy chain IgG1 CDR
      and FR region

<400> SEQUENCE: 127

Glu Val Gln Leu Gln Glu Ser Gly Pro Glu Leu Val Lys Pro Gly Ala
1               5                   10                  15

Ser Val Lys Met Ser Cys Lys Ala Ser Gly Tyr Thr Phe Thr Thr Tyr
            20                  25                  30

Val Met His Trp Val Lys Gln Lys Pro Gly Gln Gly Leu Glu Trp Ile
        35                  40                  45

Gly Tyr Ile Asp Pro Tyr Asn Asp Gly Thr Lys Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Thr Arg Gly Asn Gly Asn Tyr Glu Ser Tyr Tyr Ala Met Asp Tyr Trp
            100                 105                 110

Gly Gln Gly Thr Ser Val Thr Val Ser Ser Ala
        115                 120

<210> SEQ ID NO 128
<211> LENGTH: 25
<212> TYPE: PRT
<213> ORGANISM: Artificial Sequence
<220> FEATURE:
<223> OTHER INFORMATION: Description of Artificial Sequence:anti-Wnt2
      monoclonal antibody 8B11.H6 heavy chain IgG1 FR1
      region

<400> SEQUENCE: 128

Glu Val Gln Leu Gln Glu Ser Gly Pro Glu Leu Val Lys Pro Gly Ala
1               5                   10                  15

Ser Val Lys Met Ser Cys Lys Ala Ser
            20                  25

<210> SEQ ID NO 129
<211> LENGTH: 338
<212> TYPE: DNA
<213> ORGANISM: Artificial Sequence
<220> FEATURE:
<223> OTHER INFORMATION: Description of Artificial Sequence:anti-Wnt2
      monoclonal antibody 8B11.H6 light chain kappa
      (kappa chain 2) CDR and FR region

<400> SEQUENCE: 129
gacattgtga tgacacagac tccactcact ttgtcggtta ccattggaca accagcctct      60
ttctcttgca agtcaagtca gagactctta tatagtaatg gaaaaaccta tttgaattgg    120
ttattacaga ggccaggcca gtctccaaag cgcctaatct atctggtgtc taaactggac    180
tctggagtcc ctgacaggtt cactggcagt ggatcaggaa cagatttac actgaaaatc     240 agcagagtgg aggctgagga tttgggagtt tattactgcg tgcaaggtac acattttcct   300
tggacgttgc ggtggaggca ccaagctgaa atcaatcg                            338

<210> SEQ ID NO 130
<211> LENGTH: 78
<212> TYPE: DNA
<213> ORGANISM: Artificial Sequence
<220> FEATURE:
<223> OTHER INFORMATION: Description of Artificial Sequence:anti-Wnt2
      monoclonal antibody 8B11.H6 light chain kappa
      (kappa chain 2) FR1 region

<400> SEQUENCE: 130

```
gacattgtga tgacacagac tccactcact ttgtcggtta ccattggaca accagcctct    60
ttctcttgca agtcaagt                                                  78
```

<210> SEQ ID NO 131
<211> LENGTH: 33
<212> TYPE: DNA
<213> ORGANISM: Artificial Sequence
<220> FEATURE:
<223> OTHER INFORMATION: Description of Artificial Sequence:anti-Wnt2
      monoclonal antibody 8B11.H6 light chain kappa
      (kappa chain 2) CDR1 region

<400> SEQUENCE: 131

```
cagagactct tatatagtaa tggaaaaacc tat                                 33
```

<210> SEQ ID NO 132
<211> LENGTH: 51
<212> TYPE: DNA
<213> ORGANISM: Artificial Sequence
<220> FEATURE:
<223> OTHER INFORMATION: Description of Artificial Sequence:anti-Wnt2
      monoclonal antibody 8B11.H6 light chain kappa
      (kappa chain 2) FR2 region

<400> SEQUENCE: 132

```
ttgaattggt tattacagag gccaggccag tctccaaagc gcctaatcta t             51
```

<210> SEQ ID NO 133
<211> LENGTH: 108
<212> TYPE: DNA
<213> ORGANISM: Artificial Sequence
<220> FEATURE:
<223> OTHER INFORMATION: Description of Artificial Sequence:anti-Wnt2
      monoclonal antibody 8B11.H6 light chain kappa
      (kappa chain 2) FR3 region

<400> SEQUENCE: 133

```
aaactggact ctggagtccc tgacaggttc actggcagtg gatcaggaac agattttaca    60
ctgaaaatca gcagagtgga ggctgaggat ttgggagttt attactgc                108
```

<210> SEQ ID NO 134
<211> LENGTH: 33
<212> TYPE: DNA
<213> ORGANISM: Artificial Sequence
<220> FEATURE:
<223> OTHER INFORMATION: Description of Artificial Sequence:anti-Wnt2
      monoclonal antibody 8B11.H6 light chain kappa
      (kappa chain 2) CDR3 region

<400> SEQUENCE: 134

```
gtgcaaggta cacattttcc ttggacgttg cgg                                 33
```

<210> SEQ ID NO 135
<211> LENGTH: 369
<212> TYPE: DNA
<213> ORGANISM: Artificial Sequence
<220> FEATURE:
<223> OTHER INFORMATION: Description of Artificial Sequence:anti-Wnt2
      monoclonal antibody 8B11.H6 heavy chain IgG1 CDR
      and FR region

<400> SEQUENCE: 135

```
gaggttcagc tggaggagtc aggacctgag ctggtaaagc ctggggcttc tgtgaagatg    60
tcctgcaagg cttctggata cacattcact acctatgtta tgcactgggt gaaacagaag   120
cctgggcagg gccttgagtg gattggatac attgatcctt acaatgatgg tactaagtac   180
```

```
aatgagaagt tcaaaggcaa ggccacactg acttcagaca atcctccag cacagcctac      240 atggagctca gcagcctgac ctctgaggac tctgcggtct attactgtac aagagggaat      300
ggtaactacg agagttacta tgctatggac tactggggtc aaggaacctc agtcaccgtc      360
tcctcagcc                                                              369
```

```
<210> SEQ ID NO 136
<211> LENGTH: 75
<212> TYPE: DNA
<213> ORGANISM: Artificial Sequence
<220> FEATURE:
<223> OTHER INFORMATION: Description of Artificial Sequence:anti-Wnt2
      monoclonal antibody 8B11.H6 heavy chain IgG1 FR1
      region

<400> SEQUENCE: 136
gaggttcagc tggaggagtc aggacctgag ctggtaaagc ctggggcttc tgtgaagatg       60
tcctgcaagg cttct                                                        75
```

```
<210> SEQ ID NO 137
<211> LENGTH: 112
<212> TYPE: PRT
<213> ORGANISM: Artificial Sequence
<220> FEATURE:
<223> OTHER INFORMATION: Description of Artificial Sequence:anti-Wnt2
      monoclonal antibody 17F7.G7 (subclone B, chain 2)
      light chain kappa CDR and FR region

<400> SEQUENCE: 137

Asp Ile Val Met Thr Gln Thr Pro Leu Thr Leu Ser Val Thr Ile Gly
1               5                  10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Trp Thr Phe Gly Gly Gly Thr Lys Leu Lys Ser Thr
            100                 105                 110
```

```
<210> SEQ ID NO 138
<211> LENGTH: 9
<212> TYPE: PRT
<213> ORGANISM: Artificial Sequence
<220> FEATURE:
<223> OTHER INFORMATION: Description of Artificial Sequence:anti-Wnt2
      monoclonal antibody 17F7.G7 (subclone B, chain 2)
      light chain kappa CDR3 region

<400> SEQUENCE: 138

Trp Gln Gly Thr His Phe Pro Trp Thr
1               5
```

```
<210> SEQ ID NO 139
<211> LENGTH: 125
<212> TYPE: PRT
<213> ORGANISM: Artificial Sequence
<220> FEATURE:
<223> OTHER INFORMATION: Description of Artificial Sequence:anti-Wnt2
      monoclonal antibody 17F7.G7 (subclone B) heavy
```

-continued chain IgG1 CDR and FR region

<400> SEQUENCE: 139

Gln Val Gln Leu Gln Gln Ser Gly Ala Glu Leu Val Arg Pro Gly Thr
1               5                   10                  15

Ser Val Lys Val Ser Cys Lys Ala Ser Gly Tyr Thr Phe Thr Asp Tyr
            20                  25                  30

Val Leu Ser Trp Val Lys Gln Arg Thr Gly Gln Gly Leu Glu Trp Ile
        35                  40                  45

Gly Glu Ile Tyr Pro Gly Tyr Gly Ser Thr Tyr Tyr Asn Glu Lys Phe
    50                  55                  60

Lys Gly Lys Ala Thr Leu Thr Ala Asp Lys Ser Ser Asn Thr Ala Tyr
65                  70                  75                  80

Met Gln Leu Ser Ser Leu Thr Ser Glu Asp Ser Ala Val Tyr Phe Cys
                85                  90                  95

Ala Arg Trp Gly Asp Ser Phe Ala Tyr Trp Gly Gln Gly Thr Leu Val
            100                 105                 110

Thr Val Ser Ala Ala Lys Thr Thr Pro Pro Ser Val Tyr
        115                 120                 125

<210> SEQ ID NO 140
<211> LENGTH: 25
<212> TYPE: PRT
<213> ORGANISM: Artificial Sequence
<220> FEATURE:
<223> OTHER INFORMATION: Description of Artificial Sequence:anti-Wnt2
      monoclonal antibody 17F7.G7 (subclone B) heavy
      chain IgG1 FR1 region

<400> SEQUENCE: 140

Gln Val Gln Leu Gln Gln Ser Gly Ala Glu Leu Val Arg Pro Gly Thr
1               5                   10                  15

Ser Val Lys Val Ser Cys Lys Ala Ser
            20                  25

<210> SEQ ID NO 141
<211> LENGTH: 336
<212> TYPE: DNA
<213> ORGANISM: Artificial Sequence
<220> FEATURE:
<223> OTHER INFORMATION: Description of Artificial Sequence:anti-Wnt2
      monoclonal antibody 17F7.G7 (subclone B, chain 2)
      light chain kappa CDR and FR region

<400> SEQUENCE: 141
gacattgtga tgacacagac tccactcact ttgtcggtta ccattggaca accagcctcc      60
atctcttgca gtcaagtca gagcctctta gatagtgatg aaagacata tttgaattgg      120 ttgttacaga ggccaggcca gtctccaaag cgcctaatct atctggtgtc taaactggac     180
tctggagtcc ctgacaggtt cactggcagt ggatcaggga cagatttcac actgaaaatc     240
agcagagtgg aggctgagga tttgggagtt tattattgct ggcaaggtac acattttccg     300
tggacgttcg gtggaggcac caagctgaaa tcaacg                               336

<210> SEQ ID NO 142
<211> LENGTH: 51
<212> TYPE: DNA
<213> ORGANISM: Artificial Sequence
<220> FEATURE:
<223> OTHER INFORMATION: Description of Artificial Sequence:anti-Wnt2
      monoclonal antibody 17F7.G7 (subclone B, chain 2)
      light chain kappa FR2 region

```
<400> SEQUENCE: 142
ttgaattggt tgttacagag gccaggccag tctccaaagc gcctaatcta t              51

<210> SEQ ID NO 143
<211> LENGTH: 30
<212> TYPE: DNA
<213> ORGANISM: Artificial Sequence
<220> FEATURE:
<223> OTHER INFORMATION: Description of Artificial Sequence:anti-Wnt2
      monoclonal antibody 17F7.G7 (subclone B, chain 2)
      light chain kappa CDR3 region

<400> SEQUENCE: 143
ttcggtggag gcaccaagct gaaatcaacg                                       30

<210> SEQ ID NO 144
<211> LENGTH: 376
<212> TYPE: DNA
<213> ORGANISM: Artificial Sequence
<220> FEATURE:
<223> OTHER INFORMATION: Description of Artificial Sequence:anti-Wnt2
      monoclonal antibody 17F7.G7 (subclone B) heavy
      chain IgG1 CDR and FR region

<400> SEQUENCE: 144
caggtccagc tgcagcagtc tggagctgag ctggtaaggc ctgggacttc agtgaaggtg     60
tcctgcaagg cttctggata cacattcact gactatgttt taagctgggt gaagcagaga   120
actggacagg gccttgagtg gattggagag atttatcctg gatatggtag tacttactac   180
aatgagaagt tcaagggcaa ggccacactg actgctgaca atcctccaa cacagcctac    240 atgcagctca gcagcctgac atctgaggac tctgcggtct atttctgtgc aagatggggg   300
gattcttttg cttactgggg ccaagggact ctggtcactg tctctgcagc caaaacgaca   360 ccccatctg tctata                                                      376

<210> SEQ ID NO 145
<211> LENGTH: 75
<212> TYPE: DNA
<213> ORGANISM: Artificial Sequence
<220> FEATURE:
<223> OTHER INFORMATION: Description of Artificial Sequence:anti-Wnt2
      monoclonal antibody 17F7.G7 (subclone B) heavy
      chain IgG1 FR1 region

<400> SEQUENCE: 145
caggtccagc tgcagcagtc tggagctgag ctggtaaggc ctgggacttc agtgaaggtg     60
tcctgcaagg cttct                                                      75

<210> SEQ ID NO 146
<211> LENGTH: 21
<212> TYPE: PRT
<213> ORGANISM: Artificial Sequence
<220> FEATURE:
<223> OTHER INFORMATION: Description of Artificial Sequence:anti-Wnt2
      monoclonal antibody MG7 light chain kappa variant
      N-terminal part of FR1 region

<400> SEQUENCE: 146

Asp Val Val Met Thr Gln Thr Pro Leu Thr Leu Ser Val Thr Ile Gly
1               5                   10                  15

Gln Pro Ala Ser Ile
            20

<210> SEQ ID NO 147
```

```
<211> LENGTH: 63
<212> TYPE: DNA
<213> ORGANISM: Artificial Sequence
<220> FEATURE:
<223> OTHER INFORMATION: Description of Artificial Sequence:anti-Wnt2
      monoclonal antibody MG7 light chain kappa variant
      N-terminal part of FR1 region

<400> SEQUENCE: 147
gatgttgtga tgacccagac tccactcact ttgtcggtta ccattggaca accagcctcc    60
atc                                                                  63

<210> SEQ ID NO 148
<211> LENGTH: 339
<212> TYPE: DNA
<213> ORGANISM: Artificial Sequence
<220> FEATURE:
<223> OTHER INFORMATION: Description of Artificial Sequence:anti-Wnt2
      monoclonal antibody MG7 light chain kappa variant

<400> SEQUENCE: 148
gatgttgtga tgacccagac tccactcact ttgtcggtta ccattggaca accagcctcc    60
atctcttgca agtcaagtca gagcctctta gatagtgatg aaagacata tttgaattgg    120 ttgttacaga ggccaggcca gtctccaaag cgcctaatct atctggtgtc taaactggac   180
tctggagtcc ctgacaggtt cactggcagt ggatcaggga cagatttcac actgaaaatc   240
agcagagtgg aggctgagga tttgggagtt tattattgct ggcaaggtac acattttccg   300
tggacgttcg gtggaggcac caagctggaa atcaaacgg                          339

<210> SEQ ID NO 149
<211> LENGTH: 348
<212> TYPE: DNA
<213> ORGANISM: Artificial Sequence
<220> FEATURE:
<223> OTHER INFORMATION: Description of Artificial Sequence:anti-Wnt2
      monoclonal antibody MG7 heavy chain variant

<400> SEQUENCE: 149
caggttcagc tgcagcagtc tggacctgag ctggtgaagc ctggggcttc agtgaagatg    60
tcctgcaagg cttctggata cacattcact gactatgttt taagctgggt gaagcagaga   120
actggacagg gccttgagtg gattggagag atttatcctg gatatggtag tacttactac   180
aatgagaagt tcaagggcaa ggccacactg actgctgaca atcctccaa cacagcctac   240 atgcagctca gcagcctgac atctgaggac tctgcggtct attctgtgc aagatggggg   300 gattcttttg cttactgggg ccaagggact ctggtcactg tctctgca                348

<210> SEQ ID NO 150
<211> LENGTH: 19
<212> TYPE: DNA
<213> ORGANISM: Artificial Sequence
<220> FEATURE:
<223> OTHER INFORMATION: Description of Artificial Sequence:silencing
      small interfering RNA, short interfering RNA (siRNA) for
      human Wnt2

<400> SEQUENCE: 150
gaagatggga agcgccaag                                                 19

<210> SEQ ID NO 151
<211> LENGTH: 21
<212> TYPE: DNA
<213> ORGANISM: Artificial Sequence
<220> FEATURE:
```

```
<223> OTHER INFORMATION: Description of Artificial Sequence:
      non-silencing control small interfering RNA, short interfering
      RNA (siRNA)

<400> SEQUENCE: 151
aattctccga acgtgtcacg t                                              21

<210> SEQ ID NO 152
<211> LENGTH: 2301
<212> TYPE: DNA
<213> ORGANISM: Homo sapiens
<220> FEATURE:
<223> OTHER INFORMATION: human wingless-type MMTV integration site
      family member 2 precursor (WNT2)
<220> FEATURE:
<221> NAME/KEY: CDS
<222> LOCATION: (295)..(1377)
<223> OTHER INFORMATION: human Wnt2 precursor
<220> FEATURE:
<221> NAME/KEY: sig_peptide
<222> LOCATION: (295)..(369)
<220> FEATURE:
<221> NAME/KEY: mat_peptide
<222> LOCATION: (370)..(1374)

<400> SEQUENCE: 152
agcagagcgg acgggcgcgc gggaggcgcg cagagctttc gggctgcagg cgctcgctgc      60
cgctggggaa ttgggctgtg ggcgaggcgg tccgggctgg cctttatcgc tcgctgggcc     120
catcgtttga aactttatca gcgagtcgcc actcgtcgca ggaccgagcg ggggcgggg     180 gcgcggcgag gcggcggccg tgacgaggcg ctcccggagc tgagcgcttc tgctctgggc     240
acgcatggcg cccgcacacg gagtctgacc tgatgcagac gcaaggggt taatatgaac      300 gccctctcg gtggaatctg gctctggctc cctctgctct tgacctggct cacccccgag      360
gtcaactctt catggtggta catgagagct acaggtggct cctccagggt gatgtgcgat      420
aatgtgccag gctggtgag cagccagcgg cagctgtgtc accgacatcc agatgtgatg      480
cgtgccatta gccagggcgt ggccgagtgg acagcagaat gccagcacca gttccgccag     540
caccgctgga attgcaacac cctggacagg atcacagcc tttttggcag ggtcctactc      600
cgaagtagtc gggaatctgc ctttgtttat gccatctcct cagctggagt tgtatttgcc      660
atcaccaggg cctgtagcca aggagaagta aaatcctgtt cctgtgatcc aaagaagatg     720
ggaagcgcca aggacagcaa aggcatttttt gattggggtg gctgcagtga taacattgac     780
tatgggatca aatttgcccg cgcatttgtg gatgcaaagg aaaggaaagg aaaggatgcc     840
agagccctga tgaatcttca caacaacaga gctggcagga aggctgtaaa gcggttcttg     900
aaacaagagt gcaagtgcca cggggtgagc ggctcatgta ctctcaggac atgctggctg     960
gccatggccg acttcaggaa aacgggcgat tatctctgga ggaagtacaa tgggggccatc    1020 caggtggtca tgaaccagga tgcacaggt tcactgtgg ctaacgagag gtttaagaag      1080
ccaacgaaaa atgacctcgt gtattttgag aattctccag actactgtat cagggaccga    1140
gaggcaggct ccctgggtac agcaggccgt gtgtgcaacc tgacttcccg gggcatggac    1200
agctgtgaag tcatgtgctg tgggagaggc tacgacacct cccatgtcac ccggatgacc    1260
aagtgtgggt gtaagttcca ctggtgctgc gccgtgcgct gtcaggactg cctggaagct    1320
ctggatgtgc acacatgcaa ggcccccaag aacgctgact ggacaaccgc tacatgaccc    1380
cagcaggcgt caccatccac cttcccttct acaaggactc cattggatct gcaagaacac    1440
tggacctttg ggttctttct gggggatat ttcctaaggc atgtggcctt tatctcaacg    1500 gaagcccct cttcctccct gggggcccca ggatgggggg ccacacgctg cacctaaagc    1560
```

```
ctaccctatt ctatccatct cctggtgttc tgcagtcatc tcccctcctg gcgagttctc    1620
tttggaaata gcatgacagg ctgttcagcc gggagggtgg tgggcccaga ccactgtctc    1680
cacccacctt gacgtttctt ctttctagag cagttggcca agcagaaaaa aaagtgtctc    1740
aaaggagctt tctcaatgtc ttcccacaaa tggtcccaat taagaaattc catacttctc    1800
tcagatggaa cagtaaagaa agcagaatca actgcccctg acttaacttt aacttttgaa    1860
aagaccaaga cttttgtctg tacaagtggt tttacagcta ccacccttag ggtaattggt    1920
aattacctgg agaagaatgg cttcaatac ccttttaagt ttaaaatgtg tattttccaa     1980
ggcatttatt gccatattaa aatctgatgt aacaaggtgg ggacgtgtgt cctttggtac    2040
tatggtgtgt tgtatctttg taagagcaaa agcctcagaa agggattgct ttgcattact    2100
gtccccttga tataaaaaat ctttagggaa tgagagttcc ttctcactta gaatctgaag    2160
ggaattaaaa agaagatgaa tggtctggca atattctgta actattgggt gaatatggtg    2220
gaaaataatt tagtggatgg aatatcagaa gtatatctgt acagatcaag aaaaaaagga    2280
agaataaaat tcctatatca t                                              2301
```

<210> SEQ ID NO 153
<211> LENGTH: 344
<212> TYPE: DNA
<213> ORGANISM: Artificial Sequence
<220> FEATURE:
<223> OTHER INFORMATION: Description of Artificial Sequence:anti-Wnt2
      monoclonal antibody 17F7.G7 (subclone A) light
      chain kappa CDR and FR region
<220> FEATURE:
<221> NAME/KEY: modified_base
<222> LOCATION: (286)
<223> OTHER INFORMATION: n = g, a, c or t

<400> SEQUENCE: 153

```
gacattgtgc tgacacagtc tcctgcttcc ttagctgtat ctctggggca gagggccacc    60
atctcataca gggccagcaa aagtgtcagt acatctggct atagttatat gcactggaac    120
caacagaaac caggacagcc acccagactc ctcatctatc ttgtatccaa cctagaatct    180
aggaggtcac ctgccaggtt cagtggtcag tggtgtctgg tgtacagact tcaccctcag    240
acatccatgc ctgtcggagg aggaggatgc ctgcaacctg attatntgtg cagcacatta    300
gggagcttac acgttacgga gggggaccaa gctgaaaaaa cgg                      344
```

<210> SEQ ID NO 154
<211> LENGTH: 112
<212> TYPE: PRT
<213> ORGANISM: Artificial Sequence
<220> FEATURE:
<223> OTHER INFORMATION: Description of Artificial Sequence:anti-Wnt2
      monoclonal antibody 17F7.G7 (subclone A) heavy
      chain IgG1 CDR and FR region
<220> FEATURE:
<221> NAME/KEY: MOD_RES
<222> LOCATION: (1)
<223> OTHER INFORMATION: Xaa = Lys, Gln or Glu using codon nag
<220> FEATURE:
<221> NAME/KEY: MOD_RES
<222> LOCATION: (2)
<223> OTHER INFORMATION: Xaa = Ser using codon tcn
<220> FEATURE:
<221> NAME/KEY: MOD_RES
<222> LOCATION: (106)
<223> OTHER INFORMATION: Xaa = any amino acid
<220> FEATURE:
<221> NAME/KEY: MOD_RES
<222> LOCATION: (109)
<223> OTHER INFORMATION: Xaa = any amino acid

<400> SEQUENCE: 154

Xaa Xaa Gly Pro Glu Leu Val Lys Pro Gly Ala Ser Val Lys Met Ser
1               5                   10                  15

Cys Lys Ala Ser Gly Tyr Thr Phe Thr Asp Tyr Val Leu Ser Trp Val
            20                  25                  30

Lys Gln Arg Thr Gly Gln Gly Leu Glu Trp Ile Gly Glu Ile Tyr Pro
        35                  40                  45

Gly Tyr Gly Ser Thr Tyr Tyr Asn Glu Lys Phe Lys Gly Lys Ala Thr
    50                  55                  60

Leu Thr Ala Asp Lys Ser Ser Asn Thr Ala Tyr Met Gln Leu Ser Ser
65                  70                  75                  80

Leu Thr Ser Glu Asp Ser Ala Val Tyr Phe Cys Ala Arg Trp Gly Asp
                85                  90                  95

Cys Phe Cys Leu Ser Gly Ala Lys Gly Xaa Leu Val Xaa Cys Leu Cys
            100                 105                 110

<210> SEQ ID NO 155
<211> LENGTH: 352
<212> TYPE: DNA
<213> ORGANISM: Artificial Sequence
<220> FEATURE:
<223> OTHER INFORMATION: Description of Artificial Sequence:anti-Wnt2
      monoclonal antibody 8B11.D2 light chain kappa CDR
      and FR region

<400> SEQUENCE: 155
gacattgtgc tgacacagtc tcctgcttcc ttagctgtat ctctggggca gagggccacc      60
atctcataca gggccagcaa aagtgtcagt acatctggct atagttatat gcactggaac     120
caacagaaac caggacagcc acccagactc ctcatctatc ttgtatccaa cctagaatct     180
ggggtccctg ccaggttcag tggcagtggg tctgggacag acttcaccct caacatccat     240
cctgtggagg aggaggatgc tgcaacctat tactgtcagc acattaggga gcttacacgt     300
tcggaggggg gaccaagctg gaaataaaac gggctgatgc tgcaccaact ga             352

<210> SEQ ID NO 156
<211> LENGTH: 8
<212> TYPE: PRT
<213> ORGANISM: Artificial Sequence
<220> FEATURE:
<223> OTHER INFORMATION: Description of Artificial Sequence:anti-Wnt2
      monoclonal antibody 8B11.D2 light chain kappa CDR
      and FR region translation peptide

<400> SEQUENCE: 156

Asn Gly Leu Met Leu His Gln Leu
1               5

<210> SEQ ID NO 157
<211> LENGTH: 125
<212> TYPE: PRT
<213> ORGANISM: Artificial Sequence
<220> FEATURE:
<223> OTHER INFORMATION: Description of Artificial Sequence:anti-Wnt2
      monoclonal antibody 17F7.E5 heavy chain IgG1 CDR
      and FR region
<220> FEATURE:
<221> NAME/KEY: MOD_RES
<222> LOCATION: (125)
<223> OTHER INFORMATION: Xaa = Lys, Arg, Thr or Ile

<400> SEQUENCE: 157

Gln Val Gln Leu Gln Gln Ser Gly Ala Glu Leu Gly Thr Trp Gly Phe

```
                1               5                  10                 15
Ser Glu Asp Val Leu Gln Ala Ser Gly Tyr Thr Phe Thr Asp Tyr Val
                    20                  25                  30

Leu Ser Trp Val Lys Gln Arg Thr Gly Gln Gly Leu Glu Trp Ile Gly
            35                  40                  45

Glu Ile Tyr Pro Gly Tyr Gly Ser Thr Tyr Tyr Asn Glu Lys Phe Lys
        50                  55                  60

Gly Lys Ala Thr Leu Thr Ala Asp Lys Ser Ser Asn Thr Ala Tyr Met
65                  70                  75                  80

Gln Leu Ser Ser Leu Thr Ser Glu Asp Ser Ala Val Tyr Phe Cys Ala
                85                  90                  95

Arg Trp Gly Asp Ser Phe Ala Tyr Trp Gly Gln Gly Thr Leu Val Thr
                100                 105                 110

Val Ser Ala Ala Lys Thr Thr Pro Pro Ser Val Tyr Xaa
                115                 120                 125

<210> SEQ ID NO 158
<211> LENGTH: 351
<212> TYPE: DNA
<213> ORGANISM: Artificial Sequence
<220> FEATURE:
<223> OTHER INFORMATION: Description of Artificial Sequence:anti-Wnt2
      monoclonal antibody 8B11.H6 (kappa chain 1) light
      chain kappa CDR and FR region

<400> SEQUENCE: 158
gacattgtgc tgacacagtc tcctgcttcc ttagctgtat ctctggggca gagggccacc      60
atctcataca gggccagcaa aagtgtcagt acatctggct atagttatat gcactggaac     120
caacagaaac caggacagcc acccagactc ctcatctatc ttgtatccaa cctagaatct     180
ggggtccctg ccaggttcag tggcagtggg tctgggacag acttcaccct caacatccat     240
cctgtggagg aggaggatgc tgcaacctat tactgtcagc acattaggga gcttacacgt     300
tcggaggggg gaccaagctg gaaataaaac gggctgatgc tgcaccaact a              351

<210> SEQ ID NO 159
<211> LENGTH: 342
<212> TYPE: DNA
<213> ORGANISM: Artificial Sequence
<220> FEATURE:
<223> OTHER INFORMATION: Description of Artificial Sequence:anti-Wnt2
      monoclonal antibody 17F7.G7 (subclone B, chain 1)
      light chain kappa CDR and FR region

<400> SEQUENCE: 159
gacattgtgc tgacacagtc tcctgcttcc ttagctgtat ctctggggca gagggccacc      60
atctcataca gggccagcaa aagtgtcagt acatctggct atagttatat gcactggaac     120
caacagaaac caggacagcc acccagactc ctcatctatc ttgtatccaa cctagaatct     180
ggggtccctg ccaggttcag tggcagtggg tctgggacag acttcaccct caacatccat     240
cctgtggagg aggaggatgc tgcaacctat tactgtcagc acattaggga gcttacacgt     300
tcggaggggg gaccaagctg gaaataaaac gggctgatgc tg                       342

<210> SEQ ID NO 160
<211> LENGTH: 5
<212> TYPE: PRT
<213> ORGANISM: Artificial Sequence
```

-continued

```
<220> FEATURE:
<223> OTHER INFORMATION: Description of Artificial Sequence:anti-Wnt2
      monoclonal antibody 17F7.G7 (subclone B, chain 1)
      light chain kappa CDR and FR region translation
      peptide

<400> SEQUENCE: 160

Asn Gly Leu Met Leu
1               5
```